(12) United States Patent
Sauer

(10) Patent No.: US 12,390,244 B2
(45) Date of Patent: Aug. 19, 2025

(54) TISSUE MANIPULATION DEVICE

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 244 days.

(21) Appl. No.: 18/209,162

(22) Filed: Jun. 13, 2023

(65) Prior Publication Data

US 2024/0050117 A1  Feb. 15, 2024

Related U.S. Application Data

(63) Continuation-in-part of application No. 17/945,819, filed on Sep. 15, 2022, now Pat. No. 11,857,174.

(60) Provisional application No. 63/424,840, filed on Nov. 11, 2022, provisional application No. 63/352,867, filed on Jun. 16, 2022, provisional application No. 63/335,937, filed on Apr. 28, 2022, provisional application No. 63/245,310, filed on Sep. 17, 2021.

(51) Int. Cl.
A61B 17/32 (2006.01)
A61B 17/00 (2006.01)

(52) U.S. Cl.
CPC .......... A61B 17/32002 (2013.01); A61B 2017/00274 (2013.01)

(58) Field of Classification Search
CPC .............................................. A61B 17/0218
USPC ................................................ 600/201–245
See application file for complete search history.

(56) References Cited

U.S. PATENT DOCUMENTS

| 11,857,174 B2* | 1/2024 | Sauer ................. A61B 17/0218 |
| 2003/0176883 A1 | 9/2003 | Sauer |
| 2007/0239162 A1* | 10/2007 | Bhatnagar .......... A61B 17/8858 606/86 A |
| 2010/0130817 A1 | 5/2010 | Conlon |
| 2011/0251642 A1 | 10/2011 | Ducharme |
| 2012/0071977 A1 | 3/2012 | Oglaza et al. |

FOREIGN PATENT DOCUMENTS

EP  4 292 543  12/2023

OTHER PUBLICATIONS

Extended European Search Report for Application No. 23179808.3, dated Oct. 19, 2023, 8 pages.

* cited by examiner

Primary Examiner — Eduardo C Robert
Assistant Examiner — Tara Rose E Carter
(74) Attorney, Agent, or Firm — Michael E. Coyne

(57) ABSTRACT

A tissue manipulation device includes an end effector assembly disposed at a distal end of a shaft portion, the end effector assembly including a tissue engaging assembly having first and second tissue engaging arms that each include a first arm segment, a second arm segment, and a third arm segment that are coupled by living hinges. When an adjustment member coupled to the end effector assembly is displaced from a first position to a second position, the end effector assembly transition from a first undeployed position, in which the first and second tissue engaging arms are disposed a first configuration adapted for insertion into a patient, to a second deployed position, in which the first and second tissue engaging arms are disposed a second configuration adapted to manipulate a tissue of the patient.

20 Claims, 46 Drawing Sheets

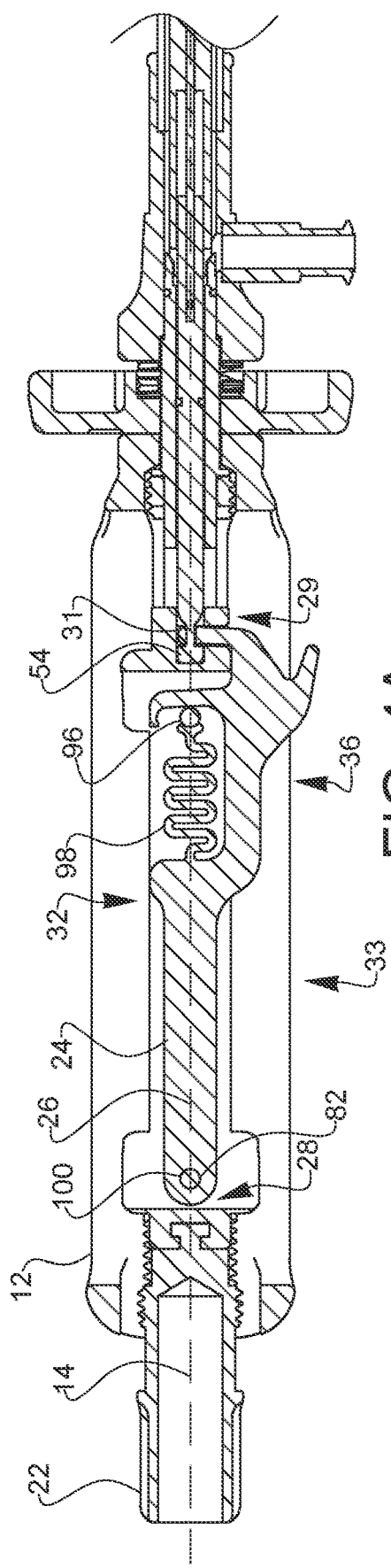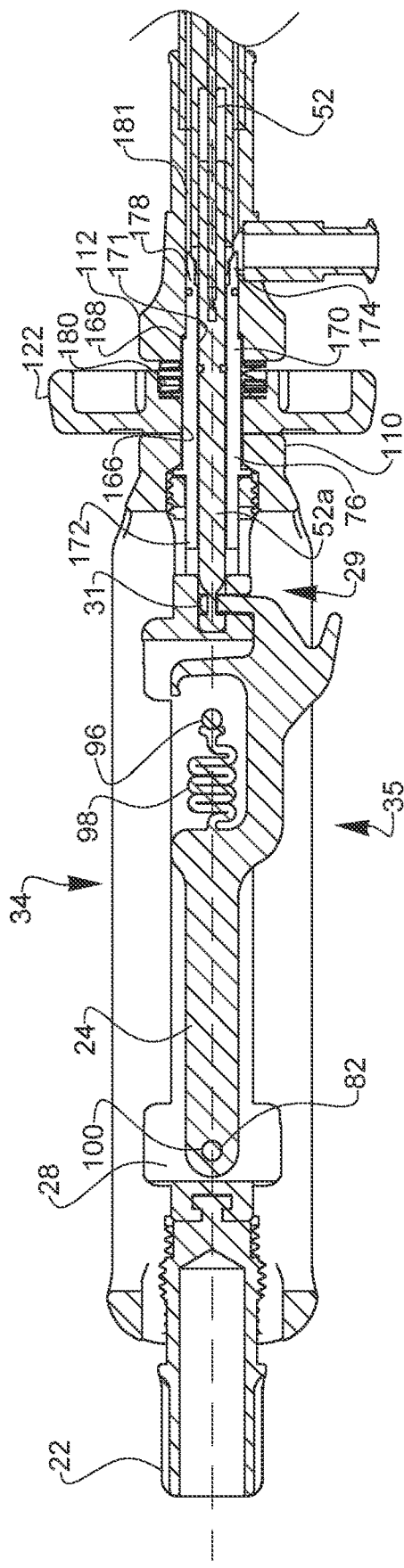

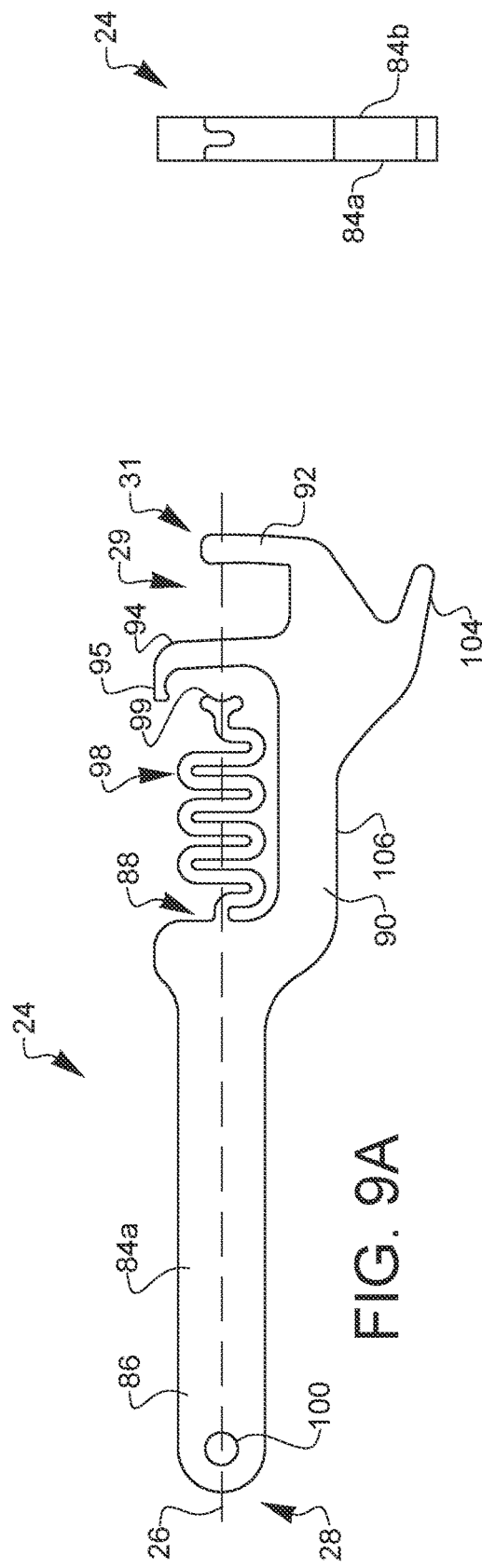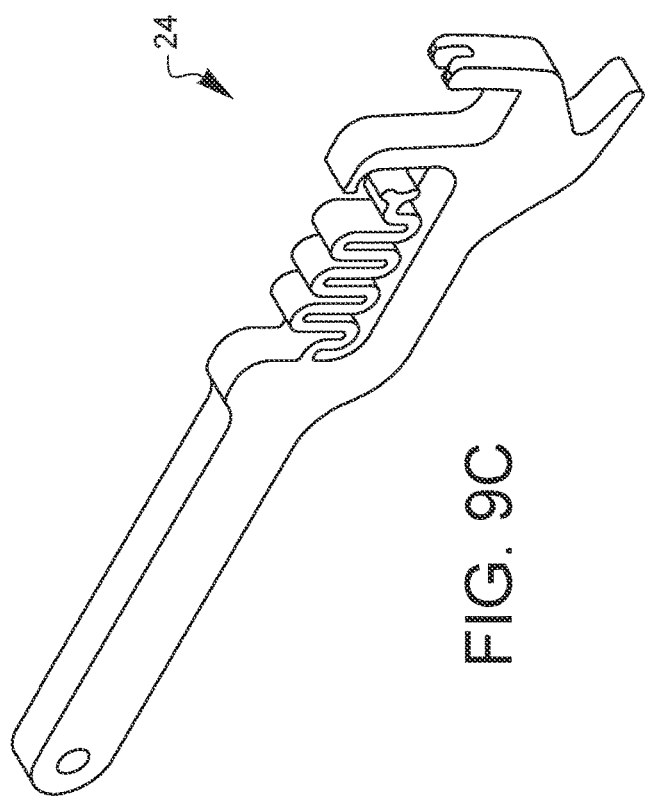

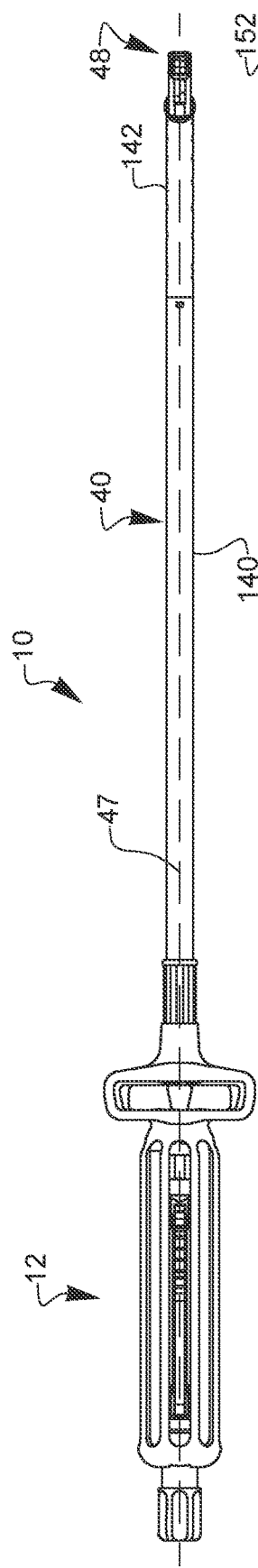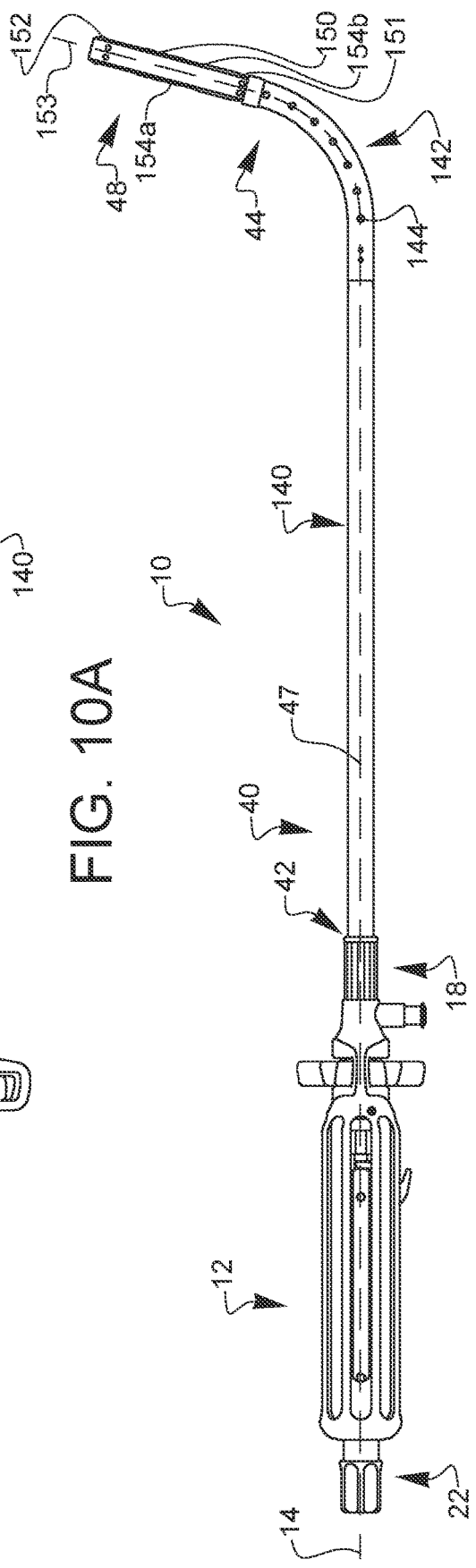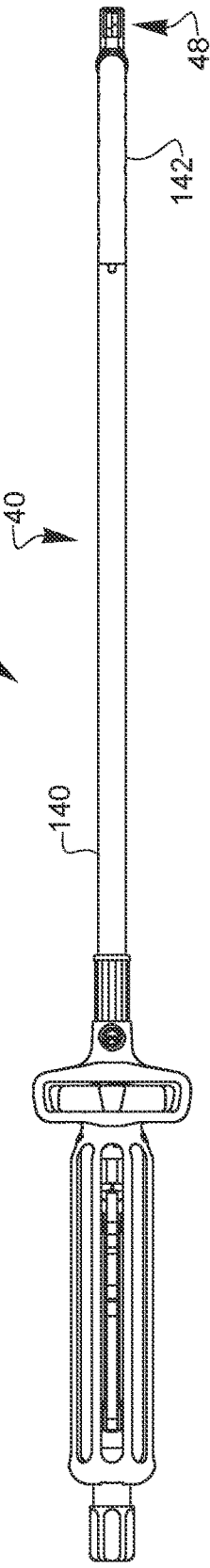
FIG. 10A
FIG. 10B
FIG. 10C

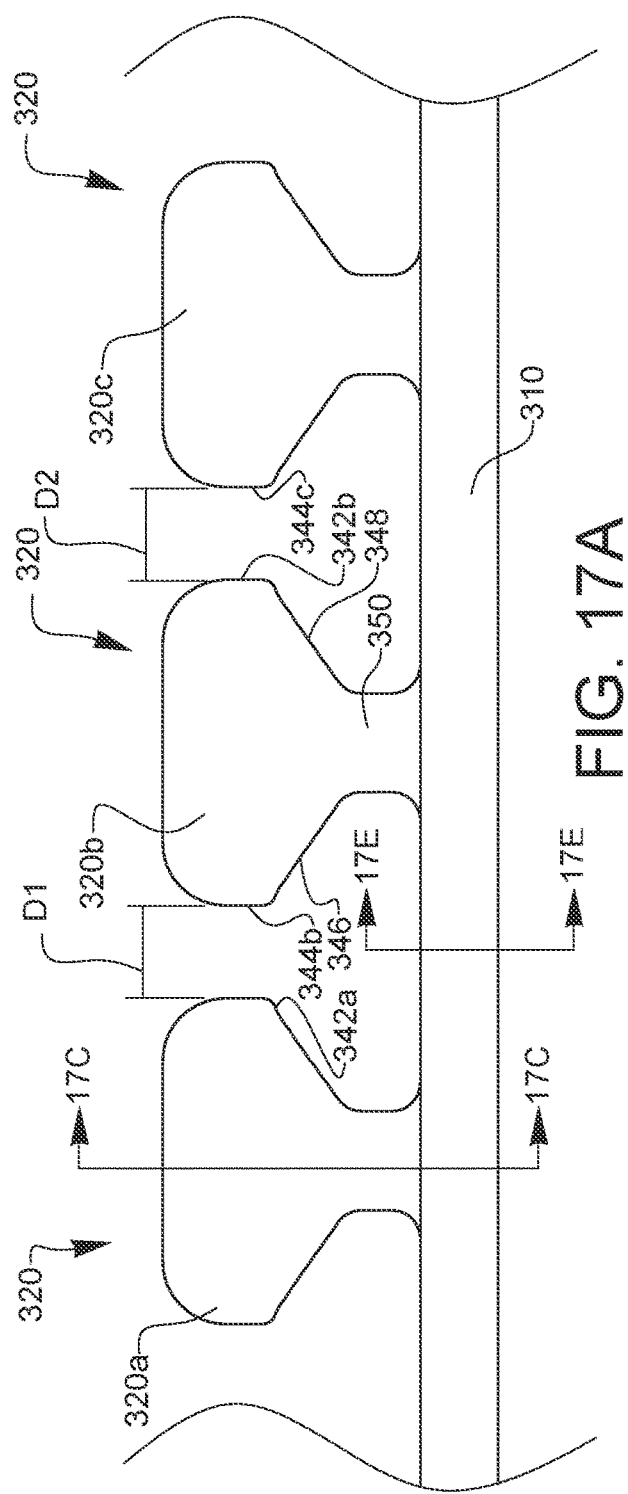
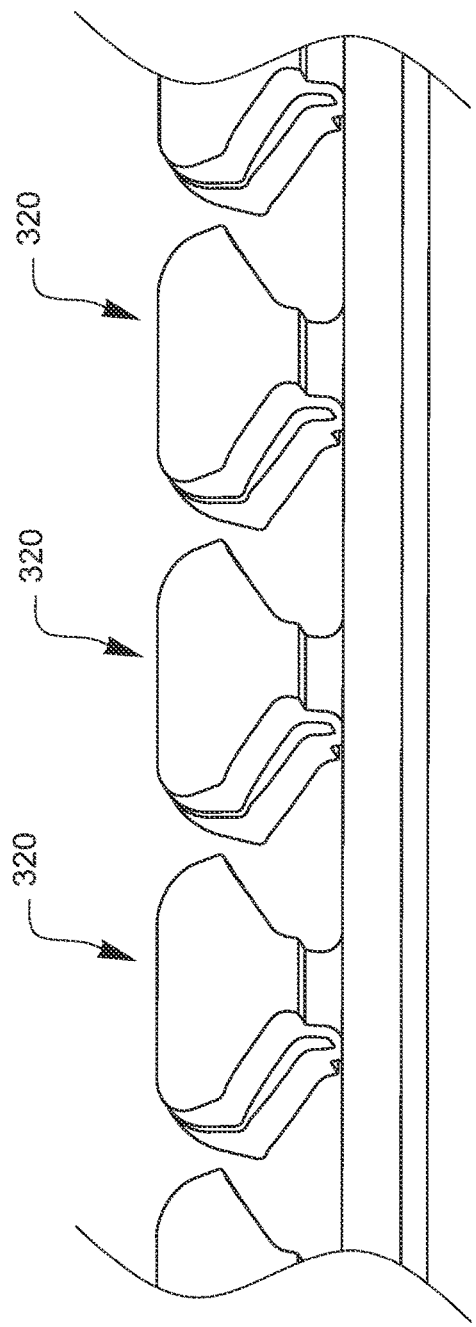

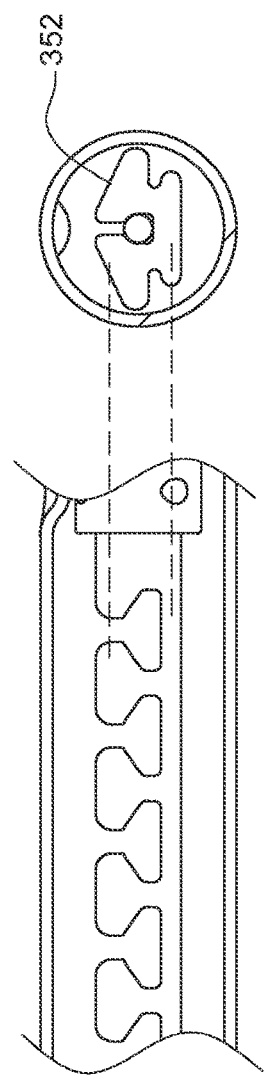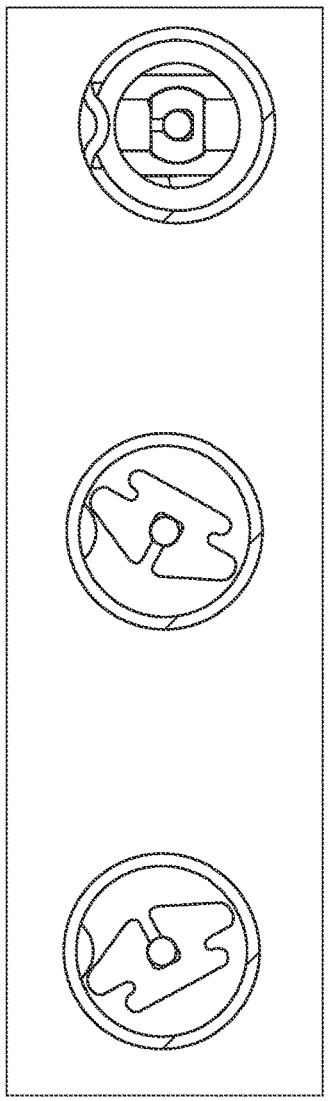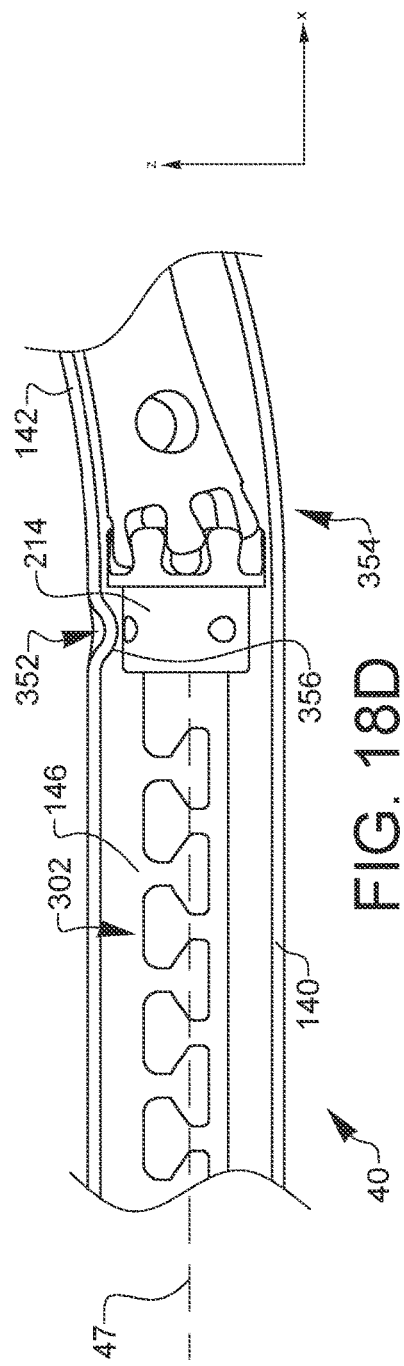

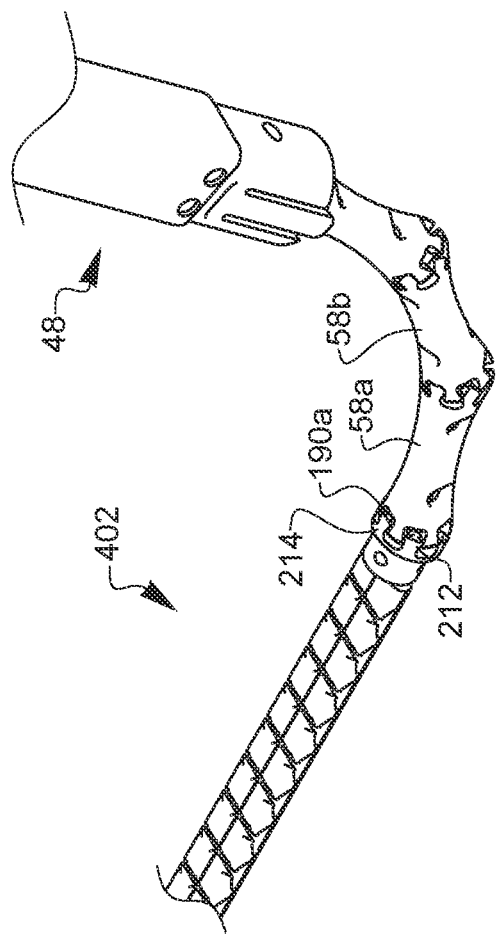
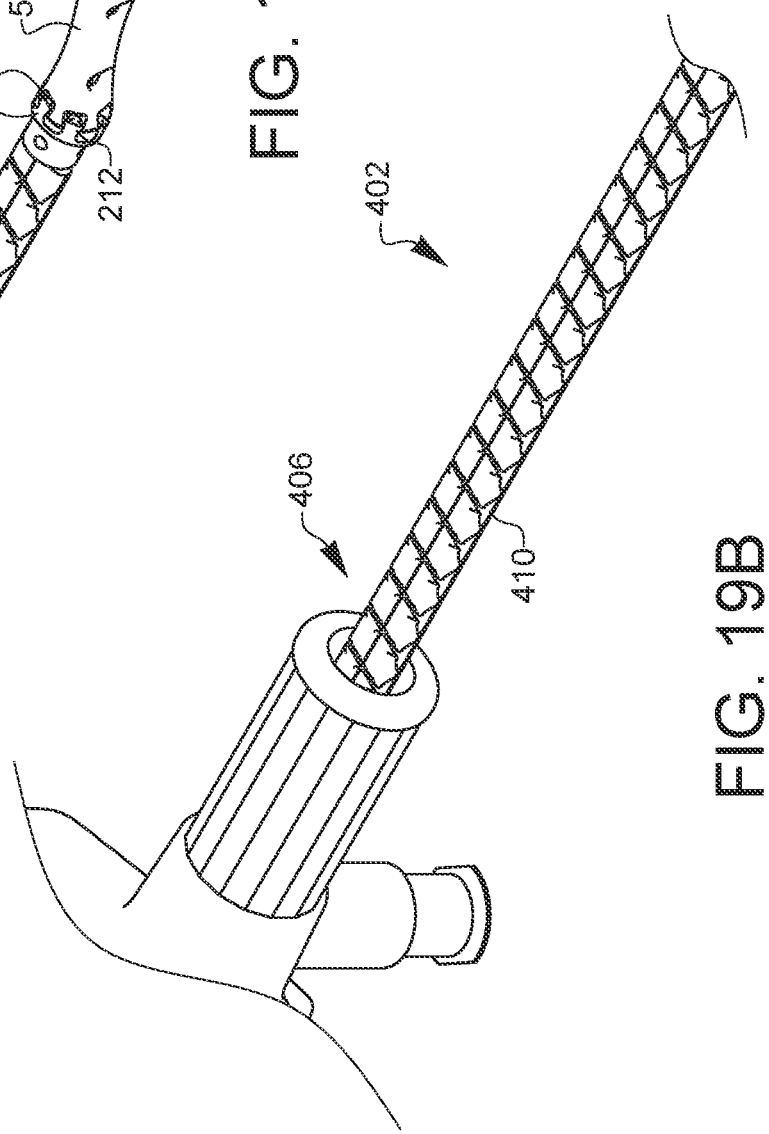

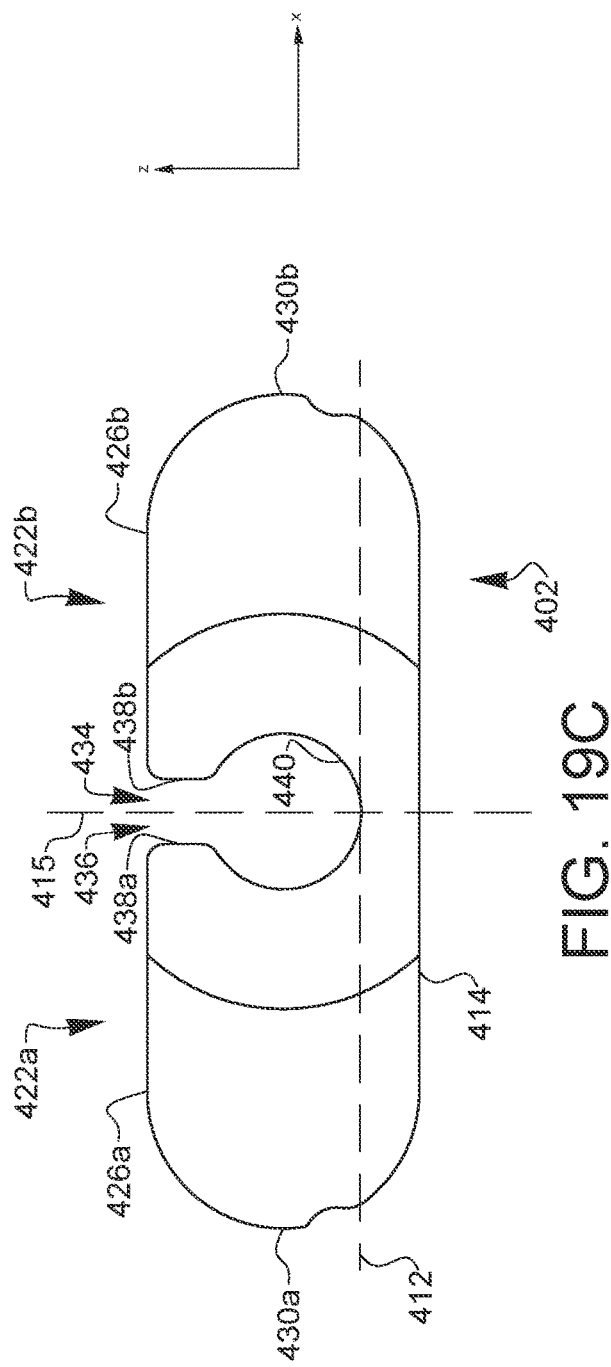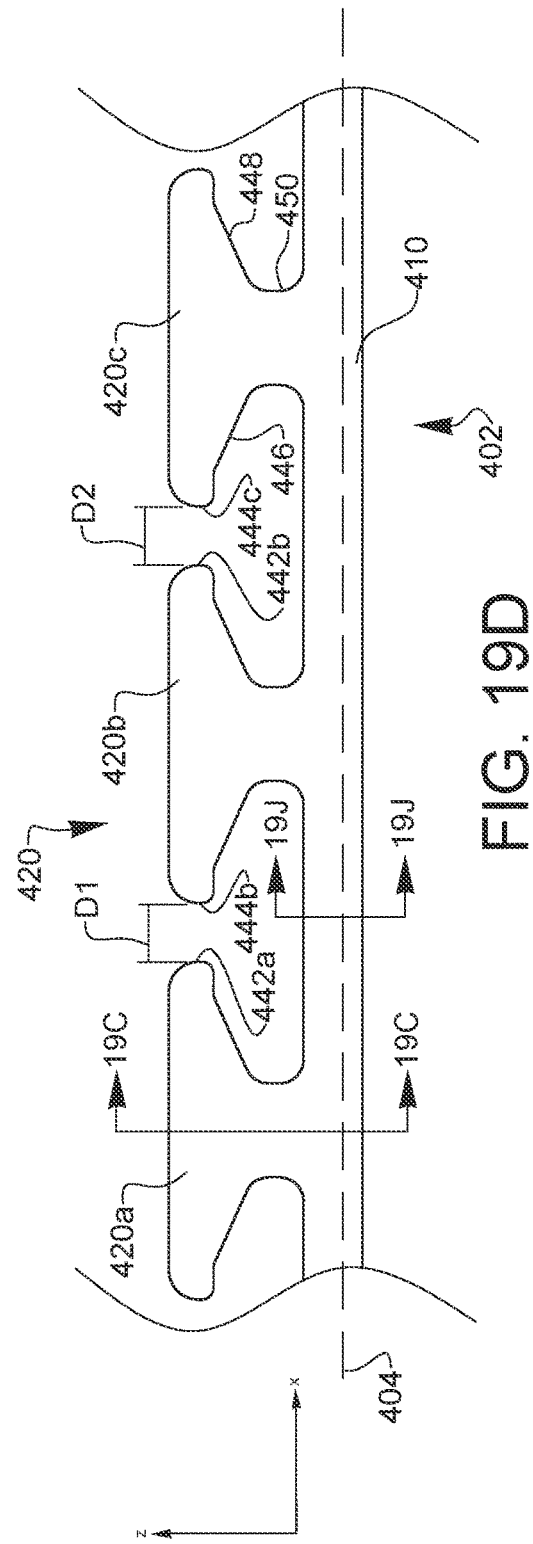
FIG. 19C
FIG. 19D

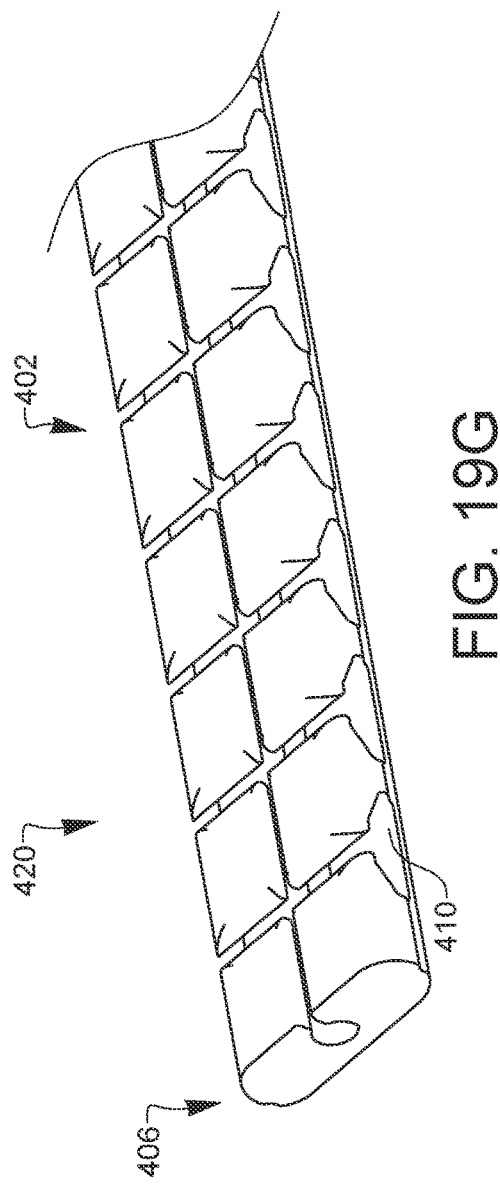
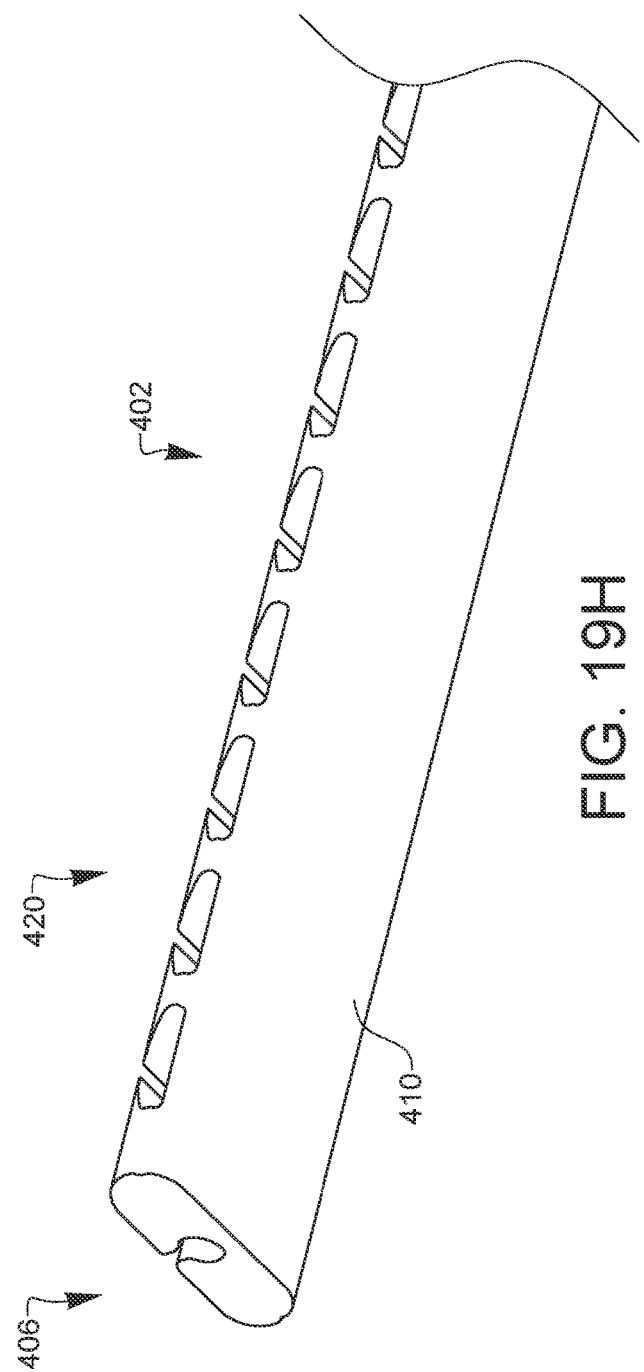
FIG. 19G
FIG. 19H

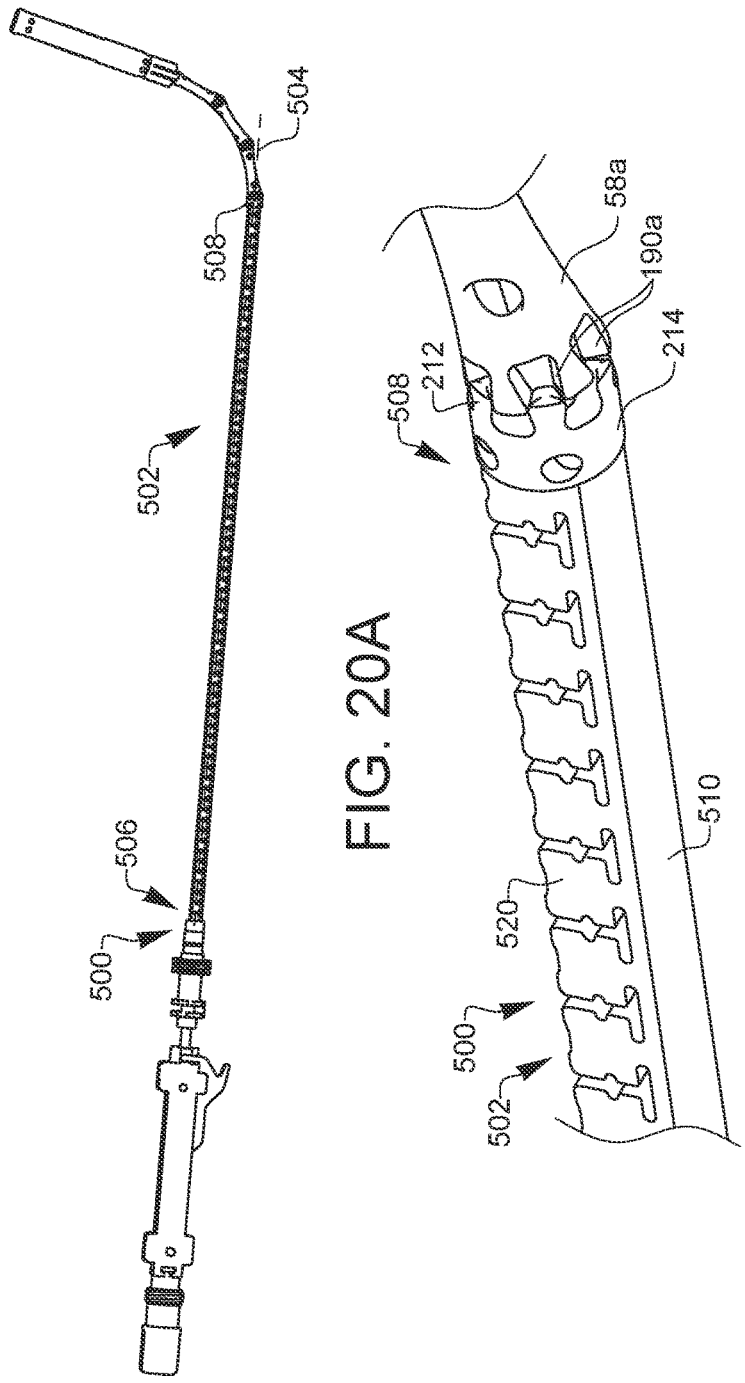
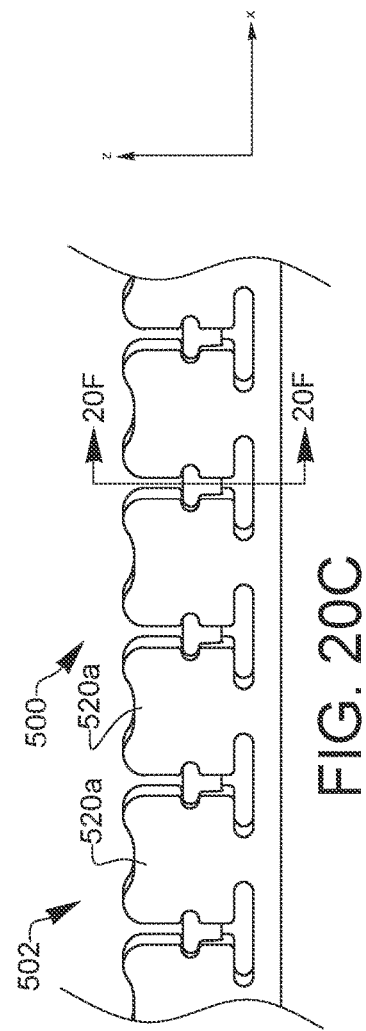
FIG. 20A
FIG. 20B
FIG. 20C

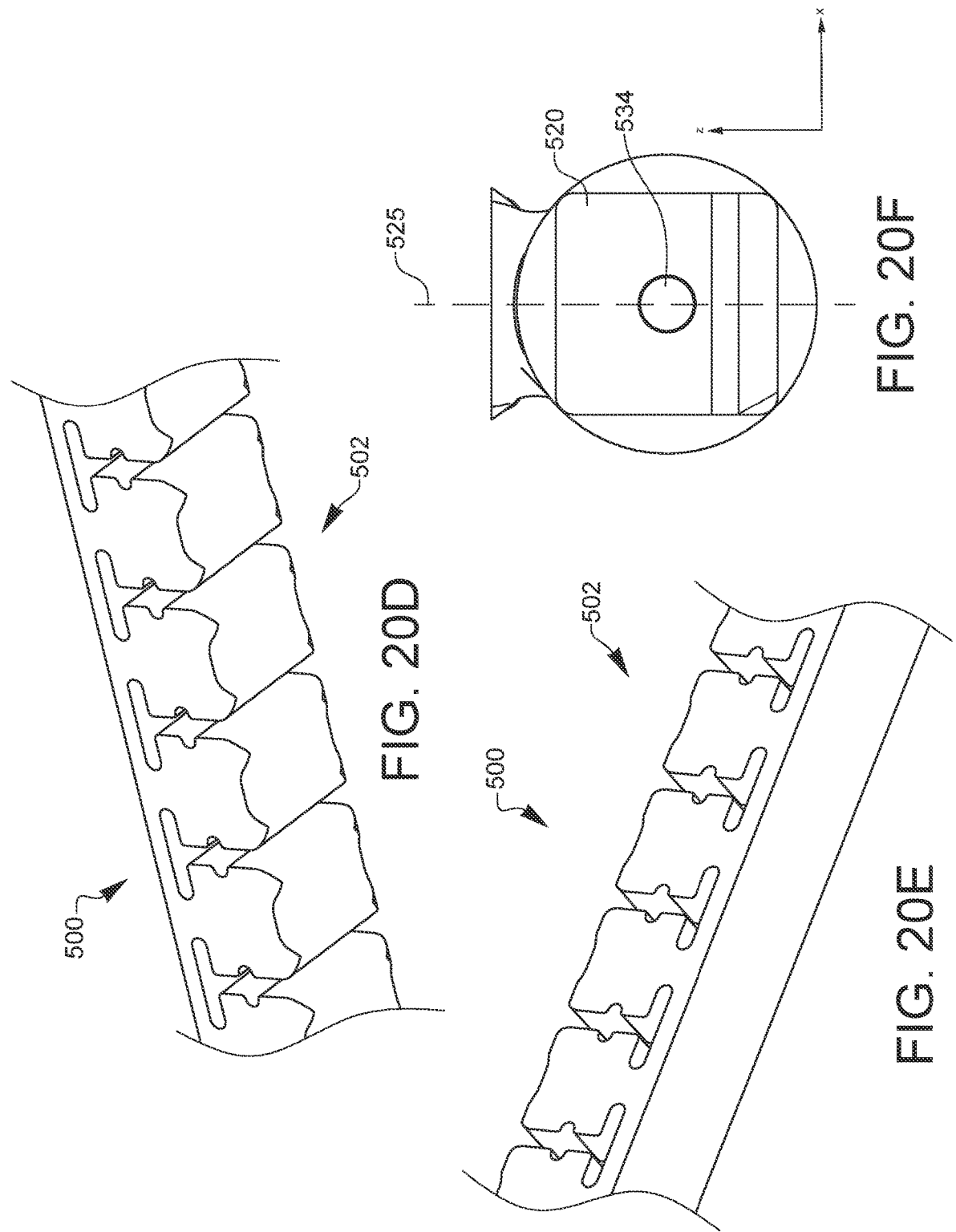

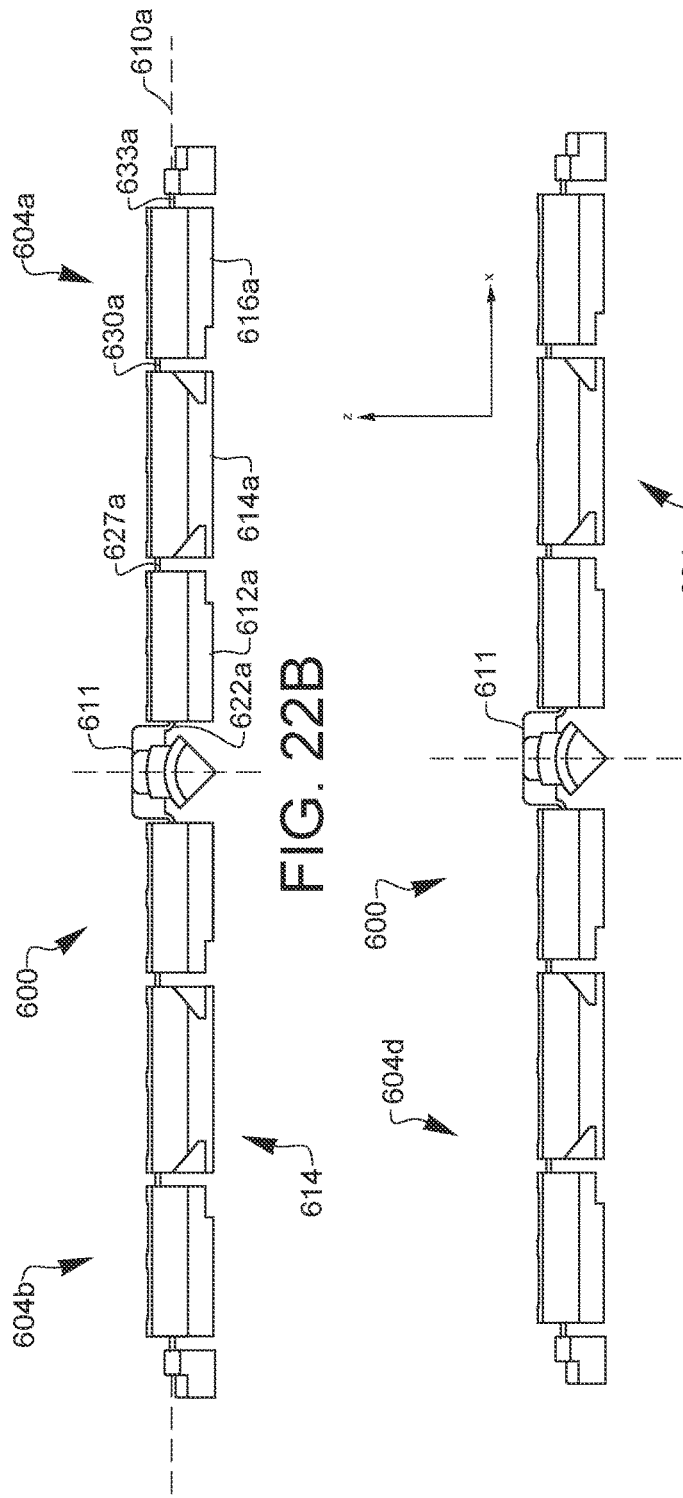
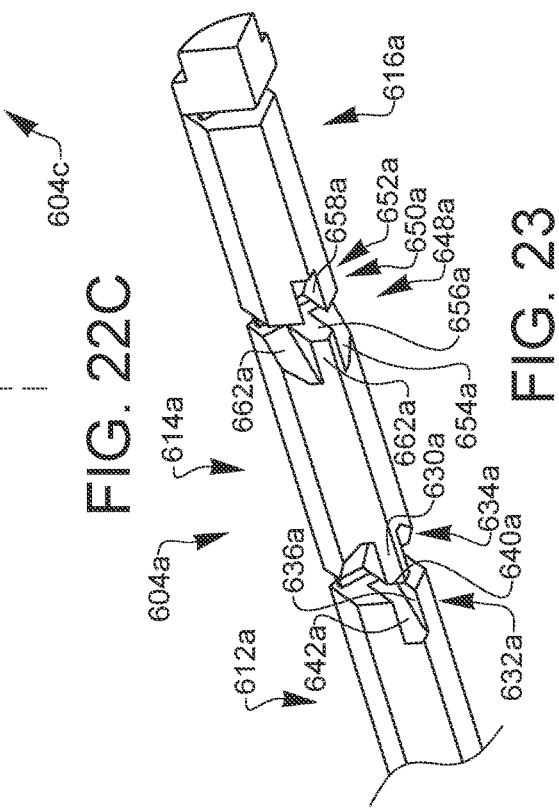
FIG. 22B
FIG. 22C
FIG. 23

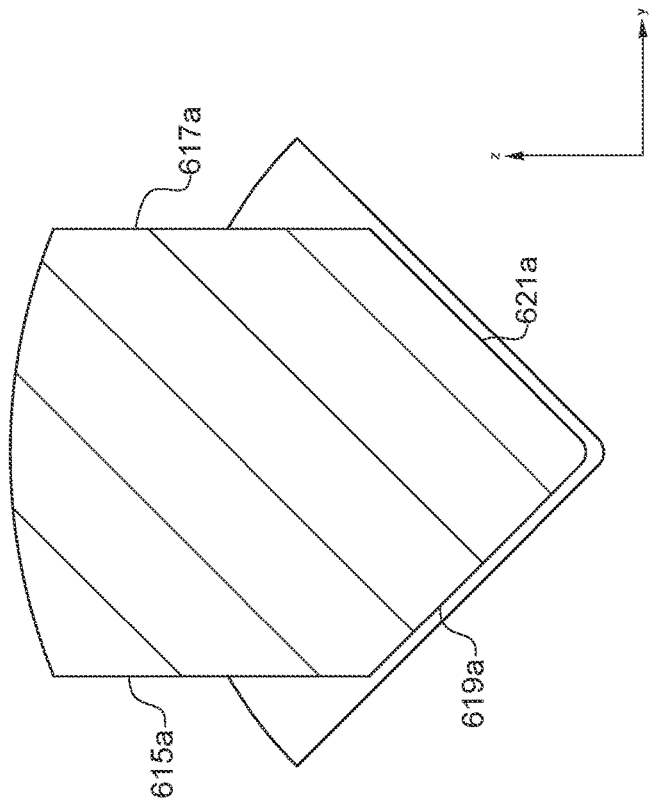
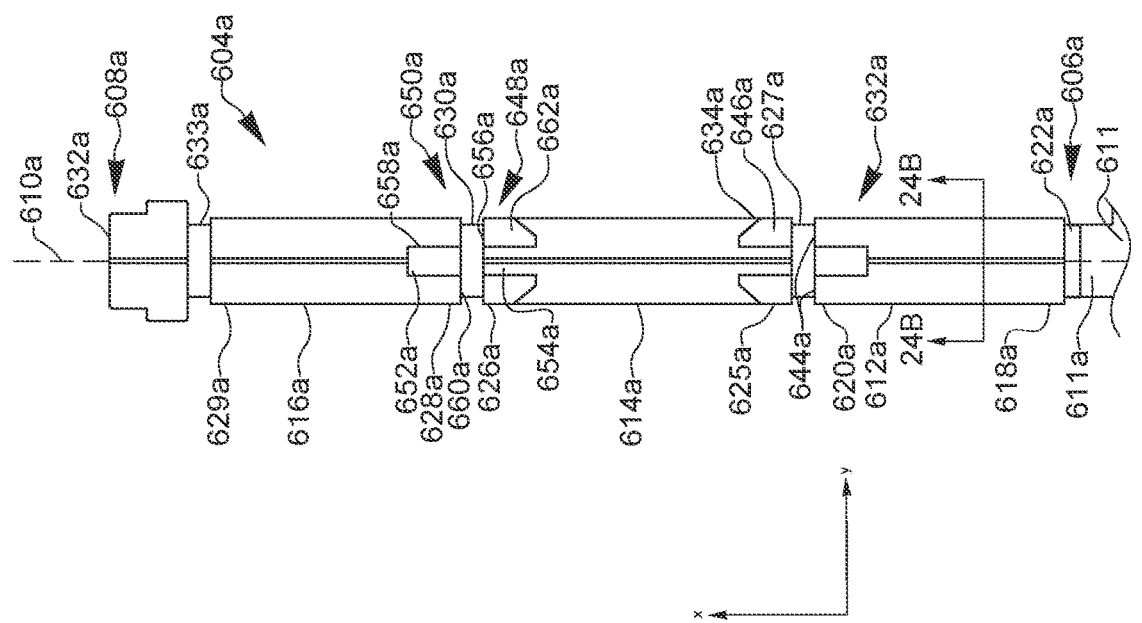
FIG. 24A
FIG. 24B

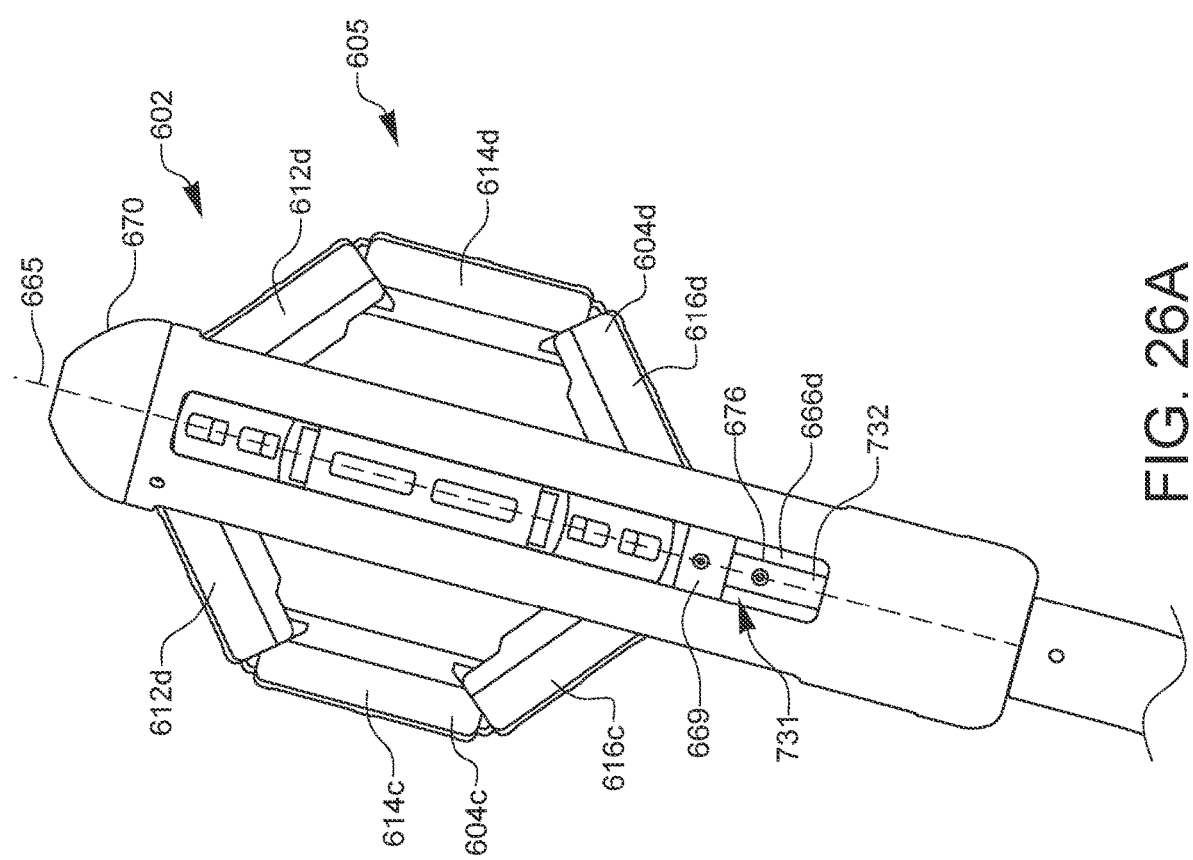

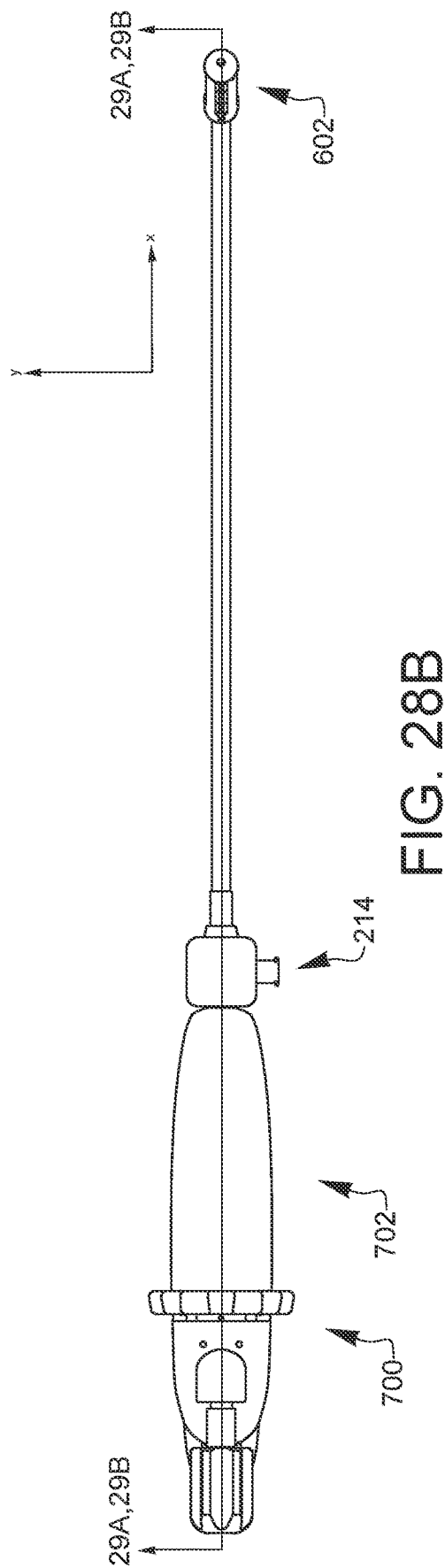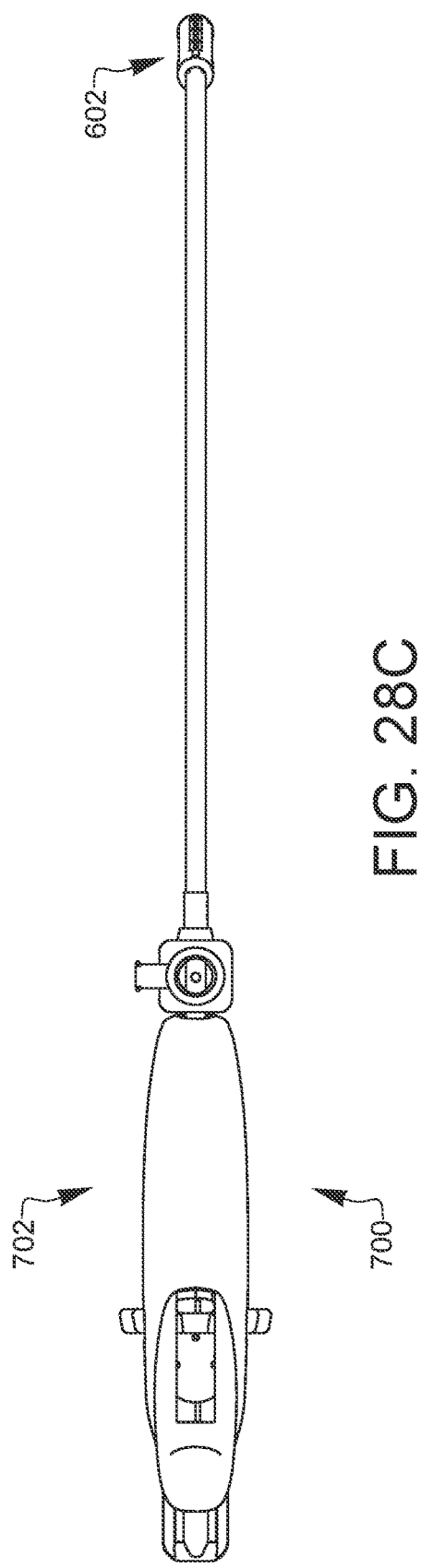
FIG. 28B
FIG. 28C

TISSUE MANIPULATION DEVICE

CROSS-REFERENCE TO RELATED APPLICATIONS

This application is a continuation-in-part of U.S. patent application Ser. No. 17/945,819, filed on Sep. 15, 2022, which claims the benefit of U.S. Provisional Patent Application No. 63/245,310, filed Sep. 17, 2021, and U.S. Provisional Patent Application No. 63/335,937, filed Apr. 28, 2022, each of which is incorporated by reference herein in its entirety. This application also claims the benefit of U.S. Provisional Patent Application No. 63/352,867, filed Jun. 16, 2022, and U.S. Provisional Patent Application No. 63/424,840, filed Nov. 11, 2022, each of which is incorporated by reference herein in its entirety.

FIELD

The claimed invention relates to surgical devices, and more specifically to a tissue manipulation device.

BACKGROUND

A prostatectomy is a medical procedure to surgically remove the prostate gland of a male patient. The procedure is often performed due to disease of the prostate, such as cancer. The procedure may be performed by open surgery or laparoscopically by the use of endoscopic instruments through small incisions in the patient. In brief, the prostate is located along the urethra leading to the bladder, and removal of the prostate is performed by exposing the prostate, dissecting the tissue surrounding the prostate, removing the prostate, and then suturing the urethra to the bladder. One problem often encountered during a prostatectomy is that the prostate is difficult to position and maneuver by the surgeon to expose the tissue and place the tissue under tension during dissection to extract the gland. This is especially a problem with a laparoscopic prostatectomy. Another problem is that the neurovascular bundles adjacent to the prostate can be damaged during the prostatectomy negatively affecting normal penile functionality. Precise dissection is important to minimize damage to surrounding tissue and especially the neurovascular bundles. Therefore, it would be desirable to provide an instrument which can be inserted through the urethra to engage the prostate and then enable the prostate's position to be precisely manipulated during a prostatectomy. It would also be desirable to provide a device that may be simple to disassemble for post-procedure cleaning and sterilization.

BRIEF DESCRIPTION OF THE DRAWINGS

FIG. 4A is a cross-sectional view of the embodiment of the tissue manipulation device of FIG. 1 with the securing member in an engaged position and in a first securing member position;

FIG. 4B is a cross-sectional view of the embodiment of the tissue manipulation device of FIG. 1 with the securing member in an engaged position and in a second securing member position;

FIG. 9A is a front view of an embodiment of the securing member;

FIG. 9B is a front view of the embodiment of the securing member of FIG. 9A;

FIG. 9C is a perspective view of the embodiment of the securing member of FIG. 9A;

FIG. 10A is a top view of the embodiment of the tissue manipulation device of FIG. 1;

FIG. 10B is a side view of the embodiment of the tissue manipulation device of FIG. 10A;

FIG. 10C is a bottom view of the embodiment of the tissue manipulation device of FIG. 10A;

FIG. 17A is a side view of a portion of the torque member of the removable portion of the embodiment of the tissue manipulation device of FIG. 16;

FIG. 17B is a partial perspective view of the torque member of the removable portion of the embodiment of the tissue manipulation device of FIG. 20A;

FIG. 18A is a cross-sectional view of a portion of the shaft portion of an embodiment of the tissue manipulation device, and the cross-sectional view is taken along the shaft axis;

FIG. 18B is a cross-sectional view of a portion of the shaft portion of an embodiment of the tissue manipulation device, and the cross-sectional view is taken normal to the shaft axis adjacent to a distal end of a linear portion of the shaft portion;

FIG. 18C includes various cross-sectional views of a portion of the shaft portion of an embodiment of the tissue manipulation device, and the cross-sectional view is taken normal to the shaft axis adjacent to a distal end of a linear portion of the shaft portion;

FIG. 18D is a cross-sectional view of a portion of the shaft portion of an embodiment of the tissue manipulation device, and the cross-sectional view is taken along the shaft axis;

FIG. 19A is a partial perspective view of an embodiment of a torque member of a removable portion of an embodiment of the tissue manipulation with the shaft portion removed for clarity;

FIG. 19B is a further partial perspective view of the embodiment of the torque member of the removable portion of FIG. 19A with the shaft portion removed for clarity;

FIG. 19C is a cross-sectional view of the embodiment of the torque member taken along section line 19C-19C in FIG. 19D;

FIG. 19D is side view of a portion of the torque member of the removable portion of the embodiment of the tissue manipulation device of FIG. 19A;

FIGS. 19F to 19H are various partial perspective views of the torque member of the removable portion of the embodiment of the tissue manipulation device of FIG. 19A;

FIG. 20A is a perspective view of an embodiment of the tissue manipulation device with the shaft portion removed for clarity;

FIG. 20B is a perspective view of a portion of the embodiment of the tissue manipulation device of FIG. 20A with the shaft portion removed for clarity;

FIG. 20C is side view of the torque member of the removable portion of the embodiment of the tissue manipulation device of FIG. 20A;

FIGS. 20D and 20E are various perspective views of the torque member of the removable portion of the embodiment of the tissue manipulation device of FIG. 20A;

FIG. 20F is a cross-sectional view of the embodiment of the torque member taken along section line 20F-20F in FIG. 20C;

FIGS. 22A to 22C are a top view, a first side view, and a second side view, respectively, of the embodiment of the tissue engaging assembly of FIGS. 21A and 21B;

FIG. 23 is a partial perspective view of a first tissue engaging arm of the embodiment of the tissue engaging assembly of FIGS. 22A to 22C;

FIG. 24A is a bottom view of the first tissue engaging arm of FIG. 23;

FIG. 24B is a cross-sectional view of the first tissue engaging arm taken along section line 24B-24B in FIG. 24A;

FIGS. 26A to 26C are a side view, a top view, and a perspective view, respectively, of the embodiment of the end effector assembly of FIG. 25 in a second deployed position;

FIGS. 28A to 28G are various views of an embodiment of a tissue manipulation device that includes the embodiment of the end effector assembly of FIG. 25 in the first undeployed position;

DETAILED DESCRIPTION

Figure 1:
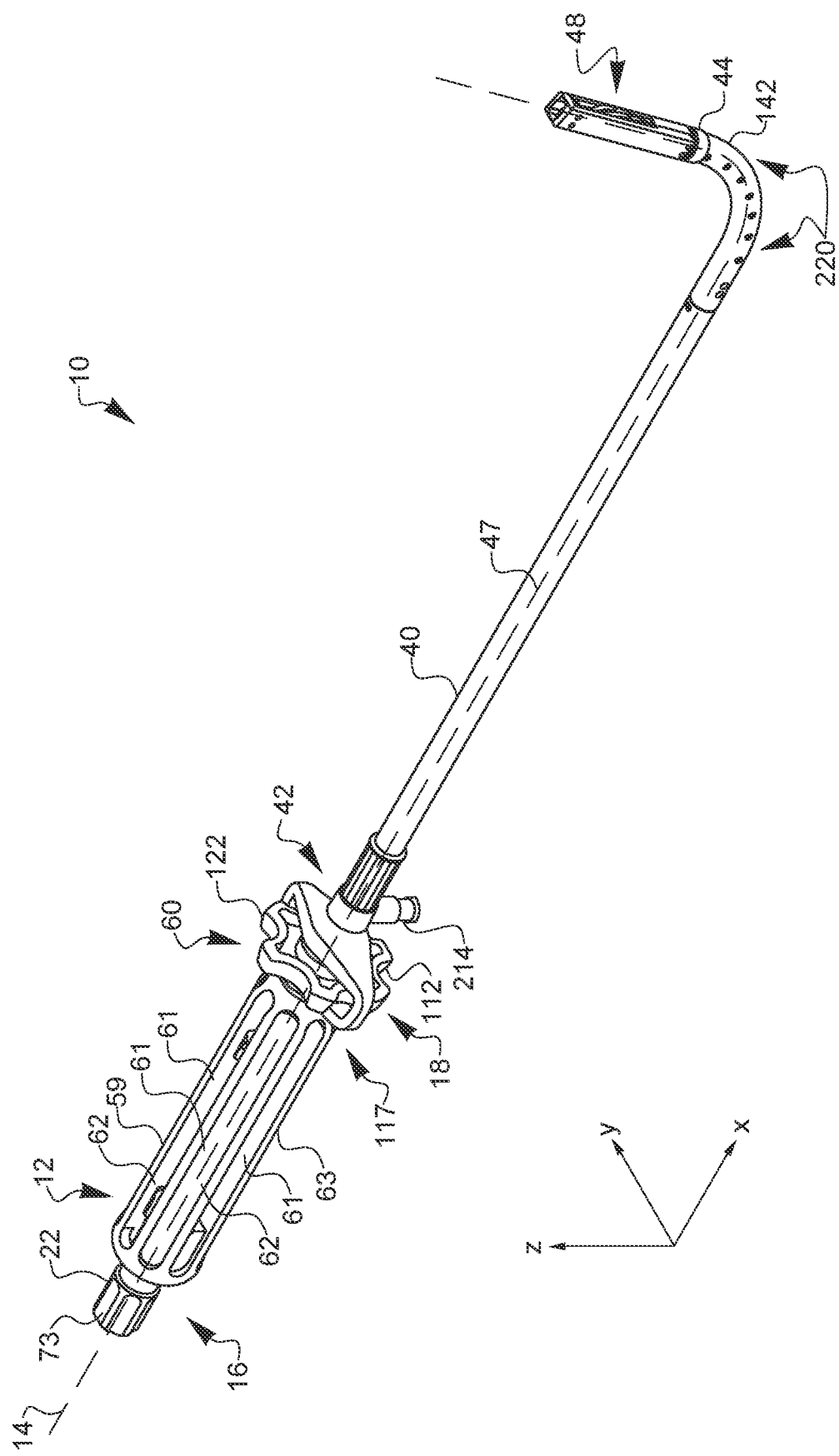
FIG. 1 is a perspective view of an embodiment of the tissue manipulation device.

Referring to FIG. 1, a tissue manipulation device 10 includes a handle portion 12 extending along a longitudinal axis 14 from a proximal end 16 to a distal end 18, and an adjustment member 22 is displaceably coupled to the proximal end 16 of the handle portion 12. As illustrated in the cross-sectional view of FIG. 3, a securing member 24 is coupled to the handle portion 12 and the securing member 24 extends along a member axis 26 from a proximal end 28 to a distal end 29. The securing member 24 includes an engagement portion 31 disposed at or adjacent to the distal end 29 of the securing member 24, and the proximal end 28 of the securing member 24 is coupled to a portion of the adjustment member 22 such that the securing member 24 is displaceable along the member axis 26 between a first securing member position 133 (illustrated in FIG. 4A) and a second securing member position (illustrated in FIG. 4B). In addition, the securing member 24 is pivotably coupled to the handle portion 12 and is pivotably displaceable from between an engaged position 36 (illustrated in FIG. 4A) and a disengaged position 39 (illustrated in FIG. 5). In the engaged position 36, the member axis 26 is parallel to or coaxially aligned with the longitudinal axis 14, and in the disengaged position 39, the member axis 26 is not parallel to or coaxially aligned with the longitudinal axis 14.

Referring again to FIG. 1, the tissue manipulation device 10 also includes a shaft portion 40 extending from a proximal end 42 to a distal end 44 along a shaft axis 47 (illustrated in FIG. 10A), and the proximal end 42 of the shaft portion 40 is coupled to the distal end of the handle portion 12. The tissue manipulation device 10 further includes an end effector 48 removably coupled to the distal end 44 of the shaft portion 40, and the end effector is operable between a first undeployed position 49 (illustrated in FIGS. 1 and 6) and a second deployed position 51 (illustrated in FIG. 8).

Figure 3:
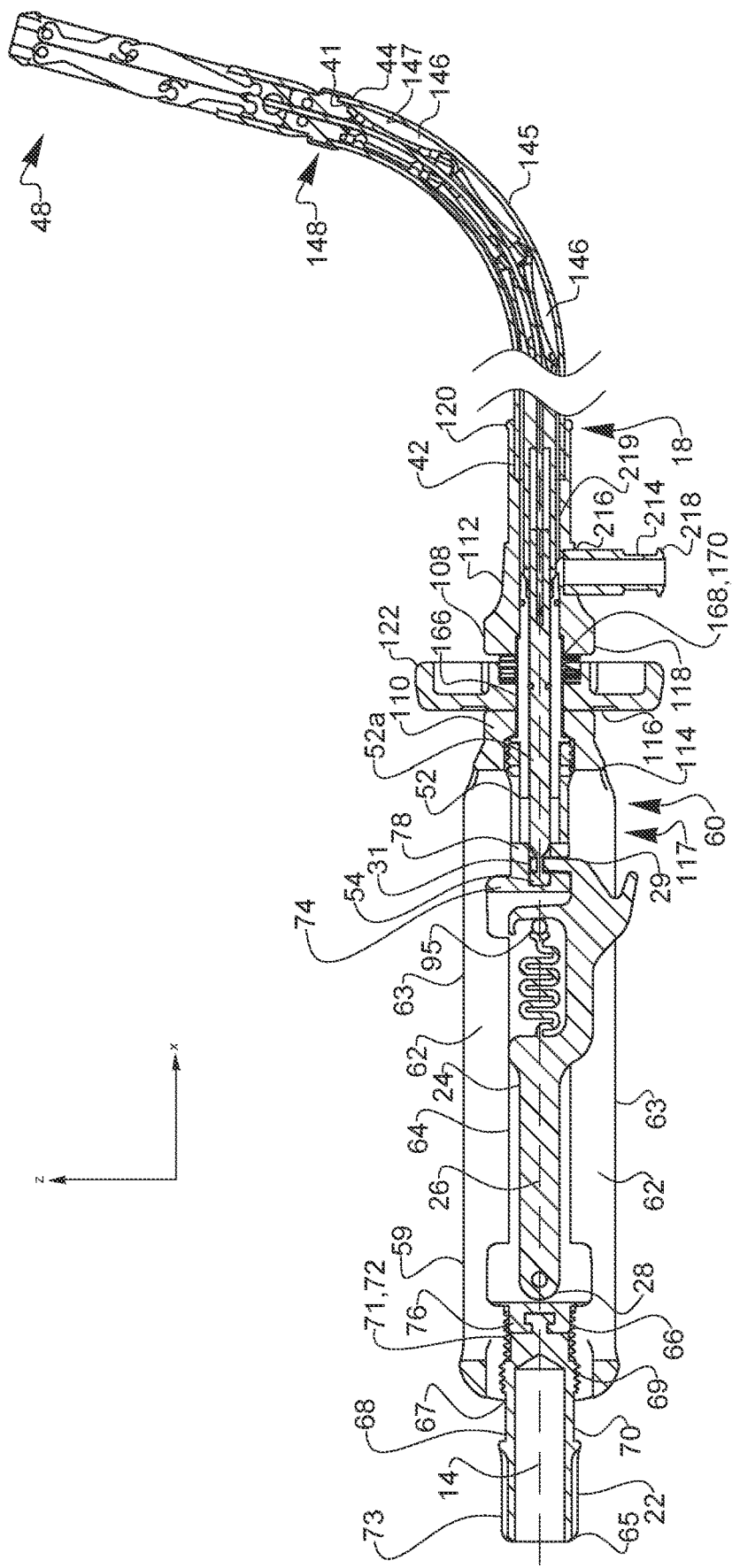
FIG. 3 is a cross-sectional view of the embodiment of the tissue manipulation device of FIG. 1 with a securing member in an engaged position.

With reference to FIG. 3, the tissue manipulation device 10 additionally includes a wire 52 (e.g., a flexible wire 52) extending from a proximal end 54 to a distal end 56 (illustrated in FIG. 8), and the distal end 56 of the wire 52 is coupled to the end effector 48. The proximal end 54 of the wire 52 is removably coupled to the engagement portion 31 of the securing member 24 when the securing member 24 is in the engaged position 36 (illustrated in FIG. 4A) and the proximal end 54 of the wire is disengaged from the engagement portion 31 of the securing member 24 when the securing member 24 is in the disengaged position 39 (illustrated in FIG. 5). In addition, when the securing member 24 is in the engaged position 36 (illustrated in FIG. 4A), the wire 52 couples the securing member 24 and the end effector 48 such that (a) when the securing member 24 is displaced from the first securing member position 133 (illustrated in FIG. 4A) to the second securing member position 35 (illustrated in FIG. 4B), the end effector 48 is displaced from the first undeployed position 49 (illustrated in FIGS. 1 and 6) to the second deployed position 51 (illustrated in FIG. 8) and (b) when the securing member 24 is displaced from the second securing member position 35 (illustrated in FIG. 4B) to the first securing member position (illustrated in FIG. 4A), the end effector 48 is displaced from the second deployed position 51 (illustrated in FIG. 8) to the first undeployed position 49 (illustrated in FIGS. 1 and 6).

So configured, when the securing member 24 is in the disengaged position 39, the end effector 48 may be decoupled from the distal end 44 of the shaft portion 40 and the wire 52 is configured to be removed from the shaft portion 40 through an aperture 41 (illustrated in FIG. 3) defined at the distal end 44 of the shaft portion 40. Accordingly, the wire 52 and attached end effector 48 may at least partially define a removable portion 57 (illustrated in FIG. 7) that may be separated and removed from the handle portion 12 and shaft portion 40 to allow the for separate processing (e.g., washing and sterilization) of the handle portion 12 and shaft portion 40. The removable portion 57 may also be processed separately from, or instead of, the handle portion 12 and shaft portion 40. In some embodiments, the removable portion 57 may further include one or more components may be coupled to the wire 52 and/or the end effector 58, such as one or more torque links 58 illustrated in FIG. 7.

Figure 2:
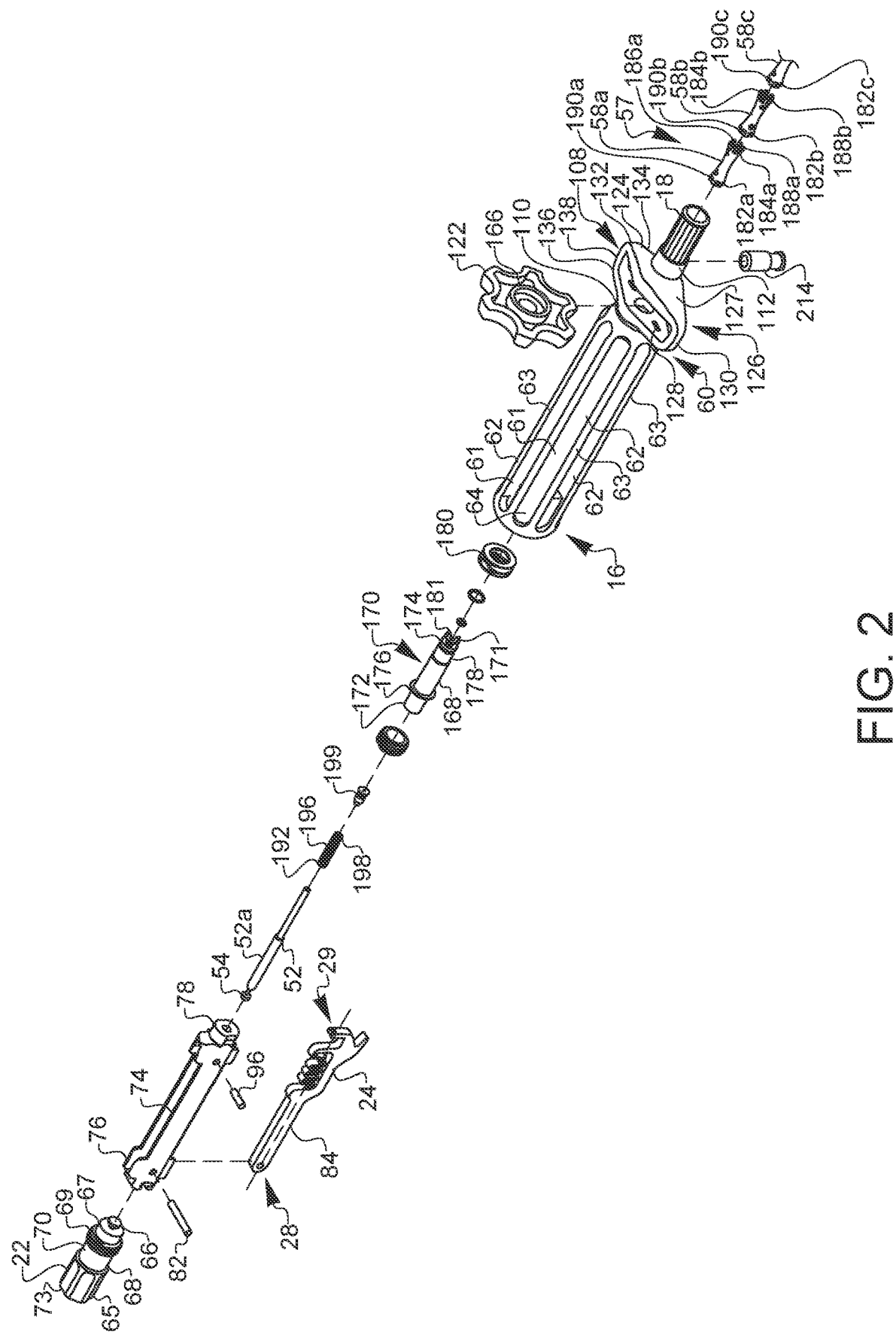
FIG. 2 is an exploded view of a portion of the embodiment of the tissue manipulation device of FIG. 1.

Turning to the tissue manipulation device 10 in more detail, and with reference to FIGS. 1, 2, and 3, the handle portion 12 may extend along the longitudinal axis 14 from the proximal end 16 to the distal end 18 and may include a grip portion 59 that may extend along the longitudinal axis 14 from the proximal end 16 of the handle portion 12 to a distal end 117 of the grip portion 59 at a first intermediary point 60 of the handle portion 12 that is proximal to the distal end 18 of the handle portion 12. The grip portion 59 may be shaped and dimensioned to be grasped by the hand of a user during a procedure. The grip portion 59 may include a plurality of slots 61 that each extends parallel to the longitudinal axis 14 from a point at or distal to the proximal end 16 of the handle portion 12 to a point at or proximal to the first intermediary point 60 of the handle portion 12. The plurality of slots 61 may be radially arrayed about the longitudinal axis 14, and the plurality of slots 61 may cooperate to define a plurality of ridges 62. Correspondingly, the plurality of ridges 62 may be radially arrayed about the longitudinal axis 14, and each of the plurality of ridges 62 may extend parallel to the longitudinal axis 14 from a point at or distal to the proximal end 16 of the handle portion 12 to a point at or proximal to the first intermediary point 60 of the handle portion 12. An outer end surface 63 of each of the plurality of ridges 62 may be contoured or textured to comfortably and securely be grasped by the hand of a user during a procedure.

Referring to FIGS. 2 and 3, the handle portion 12 may further include a central bore 64 that may extend along the longitudinal axis 14 from the proximal end 16 of the handle portion 12 to the first intermediary point 60 of the handle portion 12 or to a point distal to the first intermediary point 60 of the handle portion 12. The central bore 64 may include an end portion 71 and a portion of the end portion 71 may include a threaded portion 72.

Referring to FIGS. 1 to 3, the tissue manipulation device 10 may further include the adjustment member 22 which is displaceably coupled to the proximal end 16 of the handle portion 12. With reference to FIGS. 2 and 3, the adjustment member 22 may extend along the longitudinal axis 14 from a proximal end 65 to a distal end 66, and an insertion portion 67 may extend from the distal end 66 to an intermediary point 68. An input portion 73 may extend proximally from the insertion portion 67, and the input portion 73 may extend from the intermediary point 68 to the proximal end 65 of the adjustment member 22. The insertion portion 67 may be at least partially received in the end portion 65 of the central bore 64 of the handle portion 12, and a threaded portion 69 of an outer surface 70 of the insertion portion 67 may threadedly engage the threaded portion 72 of the end portion 65 of the central bore 64 of the handle portion 12. Accordingly, when a user rotates the input portion 73 (relative to the handle portion 12) about the longitudinal axis 14 in a first rotational direction, the adjustment member 22 displaces distally along the longitudinal axis 14. Correspondingly, when the user rotates the input portion 73 (relative to the handle portion 12) about the longitudinal axis 14 in a second rotational direction, the adjustment member 22 displaces proximally along the longitudinal axis 14.

As illustrated in the exploded view of FIG. 2, the tissue manipulation device 10 may include the securing member carrier 74 that may extend from a proximal end 76 to a distal end 78 along an axis that may be along or parallel to the longitudinal axis 14. The securing member carrier 74 may include a pair of opposing side walls 80a, 80b that may have corresponding inner surfaces that are planar or substantially planar. A pivot post 82 may extend between, and may be fixed relative to, the pair of inner surfaces of the pair of opposing side walls 80a, 80b, and the pivot post 82 may extend in a direction that is transverse to the longitudinal axis 14. The pivot post 82 may be disposed at any suitable location on the securing member carrier 74, such as at or adjacent to the proximal end 76 of the securing member carrier 74, for example.

The securing member carrier 74 may be displaceably disposed in any suitable portion of the central bore 64 of the handle portion 12. For example, as illustrated in the cross-sectional view of FIG. 3, the proximal end 76 of the securing member carrier 74 may be distal to the to the proximal end 16 of the handle portion 12 and the distal end 78 of the securing member carrier 74 may be proximal to the to the distal end 18 of the handle portion 12. In some embodiments, a portion of the proximal end 76 of the securing member carrier 74 may be coupled to or in contact with a portion of the adjustment member 22 that is at or adjacent to the distal end 66 of the adjustment member 22 such that a displacement of the adjustment member 22 along the longitudinal axis 14 for a first distance in a distal direction will result in a corresponding displacement of the securing member carrier 74 along the longitudinal axis 14 for the first distance in the distal direction. Similarly, a displacement of the adjustment member 22 along the longitudinal axis 14 for a second distance in a proximal direction will result in a corresponding displacement of the securing member carrier 74 along the longitudinal axis 14 for the second distance in the proximal direction.

As illustrated in FIGS. 2, 3, and 9A, the tissue manipulation device 10 may include the securing member 24 that may extend along the member axis 26 from the proximal end 28 to the distal end 29. Referring to FIGS. 9A and 9B, the securing member 24 may be planar or substantially planar, and may be at least partially defined by a first side surface 84a and a second side surface 84b opposite to the first side surface 84a. The first side surface 84a and the second side surface 84b may be separated by a constant width, and the width may be less than the distance separating the pair of inner surfaces of the pair of opposing side walls 80a, 80b of the securing member carrier 74 (illustrated in FIG. 2) such that all or a portion of the securing member 24 may be disposed between the pair of inner surfaces of the pair of opposing side walls 80a, 80b of the securing member carrier 74 when the securing member 24 is in the engaged position 36 (illustrated in FIG. 4A).

Still referring to FIG. 9A, the securing member 24 may include a shaft portion 86 that may extend along the member axis 26 from the proximal end 28 of the securing member 24 to an intermediate point 88. A lateral portion 90 may extend distally from the shaft portion 86, and may extend along an axis that is parallel to and offset from the member axis 26 from a point aligned with the intermediate point 88 to a point at or adjacent to the distal end 29 of the securing member 24. A support arm 92 may extend from a distal portion of the lateral portion 90 that is at or adjacent to the distal end 29 of the securing member 24. In particular, the support arm 92 may extend inwardly (i.e., towards the member axis 26) from a portion of an inner lateral edge 102 of the lateral portion 90 that is proximal to the distal end 29 of the securing member 24. The support arm 92 may extend along an axis that is transverse (or substantially transverse) to the member axis 26. The engagement portion 31 that is adapted to couple to the proximal end 54 of the wire 52 (as illustrated in FIG. 3) may be disposed on a portion of the support arm 92, such as a portion at or adjacent to an end portion of the support arm 92. The engagement portion 31 may be any feature that may removably coupled to the proximal end 54 of the wire 52, such as a slot or a yoke feature. In other embodiments, such as embodiments not having a support arm 92, the engagement portion 31 may be disposed at any suitable portion of the securing member 24, such as a portion of the securing member 24 that is at or adjacent to the distal end 29 of the securing member 24.

The securing member 24 may also include a stop arm 94 that may extend from a portion of the lateral portion 90 that is proximal to the distal end 29 of the securing member 24. In particular, the stop arm 94 may extend inwardly extend from a portion of the inner lateral edge 102 of the lateral portion 90 that is proximal to the distal end 29 of the securing member 24. The stop arm 94 may extend along an axis that is transverse (or substantially transverse) to the member axis 26, and this axis may be parallel or substantially parallel to the axis of the support arm 92 such that the stop arm 94 is proximally offset from the axis of the support arm 92 (e.g., offset in direction extending along the member axis 26 towards the proximal end 28 of the securing member 24). The stop arm 94 may be positioned on the securing member 24 such that a portion of a lower surface of the stop arm 94 may contact a portion of a stop post 96 (illustrated in FIG. 3) when the securing member 24 is in the first securing member position (illustrated in FIG. 4A) to prevent further proximal displacement of the securing member 24. The stop post 96 may extend in a direction that is transverse to the longitudinal axis 14 (and parallel to the pivot post 82), and the stop post may be fixedly coupled to a portion of the handle portion 12 in any suitable location to allow for the contact between the portion of the lower surface of the stop arm 94 and the portion of the stop post 96 when the securing member 24 is in the first securing member position (illustrated in FIG. 4A) The stop arm may have a curved end 95 that may be configured to contact the stop post 96 to prevent further pivoting of the securing member 24 relative to the handle member 12.

The securing member 24 may additionally include a resilient member 98 that may be coupled to or integrally formed with the securing member 24. For example, the resilient member 98 may be spring that extends along (or parallel to) the member axis 26 and may expand and retract along (or parallel to) the member axis 26. The resilient member 98 may include a plurality of parallel portions disposed transverse to the member axis 26, and ends of the parallel portions are coupled by alternating curved portions. A first end portion 99 of the resilient member 98 may be configured to be in contact with the stop post 96 when the securing member 24 is in the engaged position 36 (illustrated in FIG. 4A) and the first end portion 99 of the resilient member 98 may be configured to not contact the stop post 96 when the securing member 24 is pivoted to the disengaged position 39 (illustrated in FIG. 5). While the resilient member 98 has been described as integrally formed with the securing member 24, in some embodiments, the resilient member 98 may be coupled to any suitable portion of the securing member 24.

The securing member 24 may be pivotably or rotatably coupled to the securing member carrier 74 in any suitable manner. For example, a pivot aperture 100 may be disposed in a portion of the securing member 24 at or adjacent to the proximal end 28 of the securing member 24, such as a portion of the shaft portion 86 that is at or adjacent to the proximal end 28 of the securing member 24. The pivot post 82 of the securing member carrier 74 may be disposed through the pivot aperture 100 such that the securing member 24 is pivotably displaceable about the pivot post 82 between the engaged position 36 (illustrated in FIG. 4A) and the disengaged position 39 (illustrated in FIG. 5). The securing member 24 may be pivoted (for example, about the pivot post 82) to any suitable degree such that the engagement portion 31 of the securing member 24 may be disengaged or decoupled from the proximal end 54 of the wire 52. As such, when in the disengaged position 39, the member axis 26 of the securing member 24 may form an angle between 1° degree and 180° with the longitudinal axis 14 to allow the engagement portion 31 of the securing member 24 to disengage or decouple from the proximal end 54 of the wire 52.

Because the securing member 24 is fixedly coupled to the securing member carrier 74 by the pivot post 82 in the engaged position 36, the securing member 24 may translate with the securing member carrier 74 along the longitudinal axis 14 when the securing member carrier 74 is longitudinally displaced by the adjustment member 22, as previously described. In addition, because the first end portion 99 of the resilient member 98 of the securing member 24 is in contact with the stop post 96 coupled to the handle portion 12, the proximal end 76 of the securing member carrier 74 is biased into engagement with the distal end 66 of the adjustment member 22. The resilient member 98 also biases the engagement portion 31 of the securing member 24 (which is coupled to the proximal end 54 of the wire 52) toward the proximal end 16 of the handle portion 12, which maintains tension in the wire 52.

The securing member 24 may also include a grip tab 104 that may facilitate the grasping of the securing member 24 by a user to pivot the securing member 24 from the engaged position 36 the disengaged position 39, and vice versa. The grip tab 104 may extend from a portion of the lateral portion 90 that is proximal to the distal end 29 of the securing member 24, and the grip tab 104 may extend outwardly from a portion of an outer lateral edge 106 of the lateral portion 90 that is proximal to the distal end 29 of the securing member 24.

Turning again to the handle portion 12 of the tissue manipulation device 10, FIG. 1 illustrates an embodiment in which the handle portion 12 includes a wheel housing portion 108 that is distal to the distal end 117 of the grip portion 59 and coupled to or integrally formed with the distal end 117 of the grip portion 59. With reference to FIG. 3, the wheel housing portion 108 may include a proximal support portion 110 and a distal support portion 112. The proximal support portion 110 may be cylindrical or substantially cylindrical and may extend along the longitudinal axis 14 from a proximal end 114 to a distal end 116. The proximal end 114 may be coupled to or integrally formed with the distal end 117 of the grip portion 59, and one or more interior surfaces of the proximal support portion 110 may cooperate to form a portion of the central bore 64 of the handle portion 12.

The distal support portion 112 may be distal to and longitudinally offset from the proximal support portion 110. The distal support portion 112 may be cylindrical or substantially cylindrical and may extend along the longitudinal axis 14 from a proximal end 118 to a distal end 120. In embodiments including the wheel housing portion 108, the distal end 120 of the distal support portion 112 may be disposed at or correspond to the distal end of the handle portion 12. One or more interior surfaces of the distal support portion 112 may cooperate to form a portion of the central bore 64 of the handle portion 12. An adjustment wheel 122 may be disposed in the space between the proximal end 118 of the distal support portion 112 and the distal end 116 of the proximal support portion 110, and the adjustment wheel 122 will be discussed in more detail below.

As illustrated in FIG. 2, a guard portion 124 may couple the proximal support portion 110 and the distal support portion 112. In particular, the guard portion 124 may include a first arm 126 having a first distal portion 127 extending from a portion of the distal support portion 112 along an axis that is substantially transverse to the longitudinal axis 14. The first arm 126 may also include a first proximal portion 128 extending from a portion of the proximal support portion 110 along an axis that is substantially transverse to the longitudinal axis. A first lateral portion 130 may extend between an end portion of the first distal portion 127 and an end portion of the first proximal portion 128.

The guard portion 124 may further include a second arm 132 having a second distal portion 134 extending from a portion of the distal support portion 112 along an axis that is substantially transverse to the longitudinal axis 14. The second arm 132 may also include a second proximal portion 136 extending from a portion of the proximal support portion 110 along an axis that is substantially transverse to the longitudinal axis 14. A second lateral portion 138 may extend between an end portion of the second distal portion 134 and an end portion of the second proximal portion 136. The second arm 132 may be symmetrical to the first arm 126 about a plane extending along the longitudinal axis 14. So configured, with the adjustment wheel 122 disposed in the space between the proximal end 118 of the distal support portion 112 and the distal end 116 of the proximal support portion 110, the first arm 126 and the second arm 132 of the guard portion 124 surround the adjustment wheel 122 to protect against unwanted rotation due to inadvertent contact with the adjustment wheel 122.

Referring now to FIG. 10A, the tissue manipulation device 10 also includes the shaft portion 40 extending from the proximal end 42 to the distal end 44 along the shaft axis 47. The proximal end 42 of the shaft portion 40 may be coupled to the distal end 18 of the handle portion 12. In embodiments including the wheel housing portion 108, the proximal end 42 of the shaft portion 40 may be coupled to the distal end 120 of the distal support portion 112 (illustrated in FIG. 3). However, the proximal end 42 of the shaft portion 40 may be coupled to any suitable portion of the shaft portion 40, such as the distal end 117 of the grip portion 59 (illustrated in FIG. 1) in embodiments that do not include the wheel housing portion 108. The distal end 44 of the shaft portion 40 may be removably coupled to a portion of the end effector 48.

The shaft portion 40 may have any suitable shape or combination of shapes. For example, the shaft portion 40 may include a linear portion 140 and a curved portion 142. The linear portion 140 may extend from the proximal end 42 of the shaft portion to an intermediate point 144 of the shaft portion 40. The portion of the shaft axis 47 that extends along the linear portion 140 may be aligned with the longitudinal axis 14 or may be parallel to the longitudinal axis 14. In some embodiments, the portion of the shaft axis 47 that extends along the linear portion 140 may form an angle (i.e., an acute angle) with the longitudinal axis 14. The curved portion 142 of the shaft portion 40 may extend from the intermediate point 144 of the shaft portion 40 to the distal end 44 of the shaft portion 40. In some embodiments, the curved portion 142 may be linear and the portion of the shaft axis 47 that extends along the curved portion 142 may form an angle (i.e., an acute angle) with the longitudinal axis 14 and/or with the portion of the shaft axis 47 that extends along the linear portion 140. In other embodiments, the shaft portion 40 may not have a curved portion 142 and the linear portion 140 may extend from the proximal end 42 of the shaft portion 40 to the distal end 44 of the shaft portion 40. In still further embodiments, the shaft portion 40 may not have a linear portion 140 and the curved portion 142 may extend from the proximal end 42 of the shaft portion 40 to the distal end 44 of the shaft portion 40.

As illustrated in FIG. 3, the shaft portion 40 may have one or more exterior surfaces 145 and may have one or more interior surfaces 147 that define a shaft interior portion 146. The shaft interior portion 146 may open into, be in communication, and/or be aligned with the central bore 64 of the handle portion 12. The one or more exterior surfaces 145 and one or more interior surfaces 147 may have any suitable cross-sectional shape of combination of shapes. For example, the one or more exterior surfaces 145 and/or the one or more interior surfaces 147 may have a circular (or polygonal) cross-sectional shape. The cross-sectional shape of any of the one or more exterior surfaces 145 and/or the one or more interior surfaces 147 may be uniform along the entire shaft portion 40 or along one or more segments of the shaft portion 40 (e.g., the linear portion 140).

With reference to FIG. 3, the tissue manipulation device 10 additionally includes the wire 52 that extends from the proximal end 54 to the distal end 56 (illustrated in FIG. 8), and the distal end 56 of the wire 52 may be coupled to a portion of the end effector 48, such as a proximal portion 148 of the end effector 48. All or a portion of the wire 52 may be flexible to allow the wire 52 to extend through the curved portion 142 of the shaft portion 40. The wire 52 may be a single unitary part or may be an assembly of two or more segments and/or components. For example, as illustrated in FIG. 3, the wire 52 may include a coupling portion 52a disposed at or adjacent to the proximal end 54 of the wire 52. As illustrated in FIG. 3, the proximal end 54 of the wire 52 may be removably coupled to the engagement portion 31 of the securing member 24 when the securing member 24 is in the engaged position 36 (illustrated in FIG. 4A), and the proximal end 54 of the wire 52 may be shaped or dimensioned to be removably engaged by the engagement portion 31 of the securing member 24.

Figure 8:
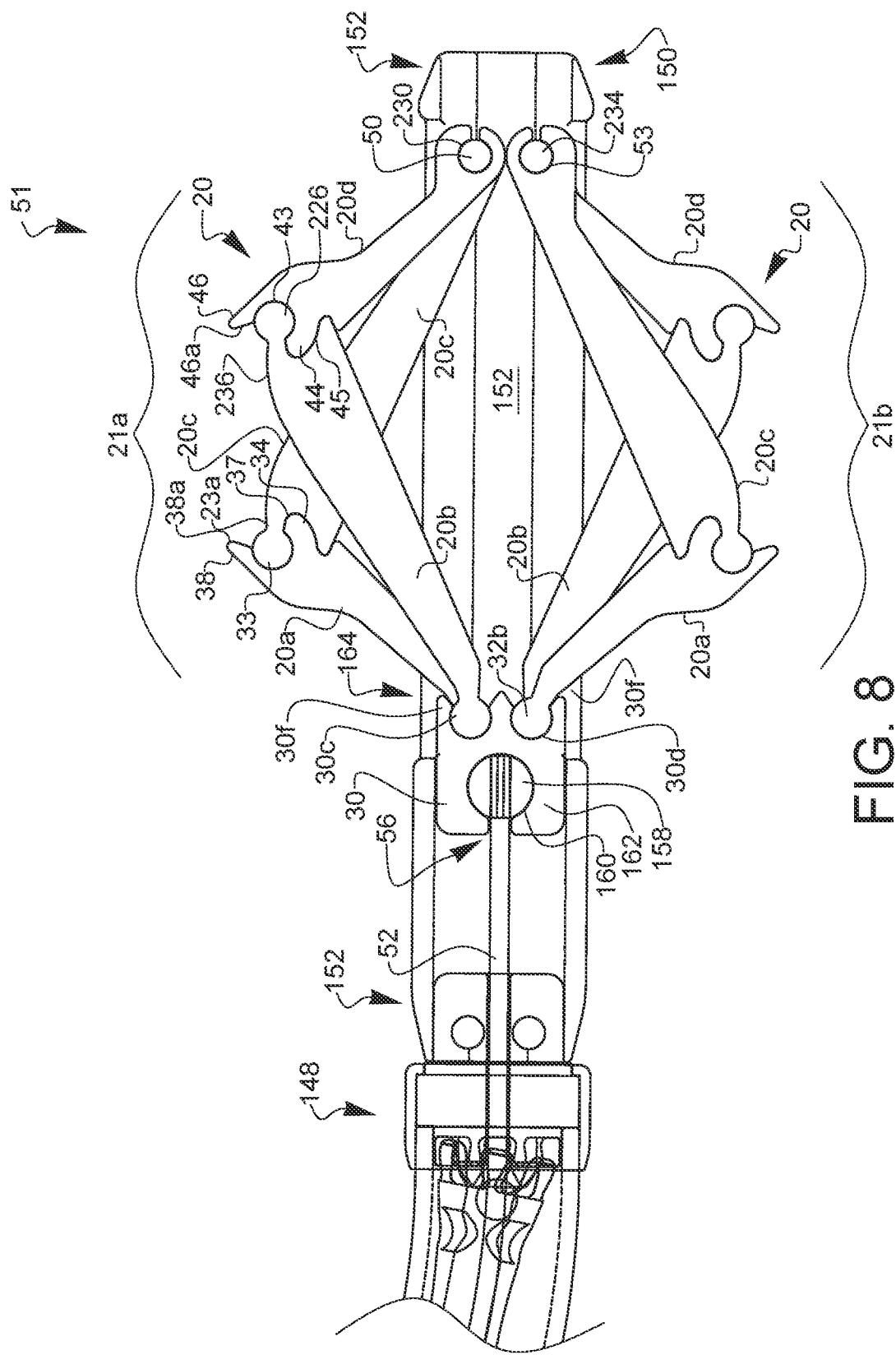
FIG. 8 is a cross-sectional view of the distal end of the shaft portion of the embodiment of the tissue manipulation device of FIG. 1 with the end effector in a second deployed position.

As illustrated in FIGS. 1, the tissue manipulation device 10 additionally includes the end effector 48 removably and rotatably coupled to the distal end 44 of the shaft portion 40, and the end effector is operable between a first undeployed position 49 (illustrated in FIGS. 1 and 6) and a second deployed position 51 (illustrated in FIG. 8). The distal end 56 of the wire 52 may be coupled to the proximal portion 148 of the end effector 48 such that when the securing member 24 is displaced (e.g., displaced distally in a direction along the member axis 26) from the first securing member position (illustrated in FIG. 4A) to the second securing member position 35 (illustrated in FIG. 4B), the end effector 48 is transitioned (e.g., expanded or deployed) from the first undeployed position 49 (illustrated in FIGS. 1 and 6) to the second deployed position 51 (illustrated in FIG. 8). Correspondingly, when the securing member 24 is displaced (e.g., displaced proximally in a direction along the member axis 26) from the second securing member position 35 (illustrated in FIG. 4B) to the first securing member position 133 (illustrated in FIG. 4A), the end effector 48 is transitioned (or contracted) from the second deployed position 51 (illustrated in FIG. 8) to the first undeployed position 49 (illustrated in FIGS. 1 and 6).

Turning to the end effector 48 in more detail, FIG. 10A illustrates an embodiment of the end effector 48 having a housing 150 that extends from a proximal end 151 to a distal end 152 along an end effector axis 153, and two windows 154a, 154b are formed on opposing lateral ends of the housing 150. As shown in the cross-sectional view of FIG. 8, the housing 150 includes a plurality of interior surfaces that cooperate to define a cavity 156 within the housing 150. In the cavity 152, disposed for extension through each of the windows 154a, 154b, is one of two sets 21a and 21b of two tissue engaging members 20. The tissue engaging members 20 are extendible from the first undeployed position 49 (illustrated in FIGS. 1 and 6) to the second deployed position 51 (illustrated in FIG. 8). In each of sets 21a and 21b, the first of the two tissue engaging members 20 is formed by a proximal member 20a and a distal member 20c, and the second of the two tissue engaging members 20 is formed by a proximal member 20b and a distal member 20d.

Each tissue engaging member 20 represents a hinged wing which is extendible radially through their respective windows 154a, 154b of the distal end. Turning to the first set 21a, proximal member 20a has a socket 33 which receives a curved member or shaft extending from the distal member 20c to form a hinge similar to a ball and socket joint. One side of the socket 33 extends to form a finger 34 which may be received in an opening 37 of distal member 20c shaped to receive finger 34. Proximal member 20a has a barb 38 which extends from the other side of the socket 33. Similarly, the proximal member 20b has a curved member or shaft 226 which is received in socket 43 of distal member 20d to form a hinge also similar to a ball and socket joint. One side of the socket 43 extends to form a finger 228 which may be received in an opening 45 of proximal member 20b shaped to receive finger 228. Proximal member 20d has a barb 46 which extends from the other side of socket 43. Proximal member 20a and distal member 20d may be of the same first length, and proximal member 20b and distal member 20c may be of the same second length, where the first length is less than the second length. The second set 21b is a mirror image of the first set 21a, and operates identically to the first set 21a.

In the first set 21a, a hole 230 is provided at the end 230 of distal member 20c through which extends a pin 50 through two openings in the sides of housing 150 near the distal end 152, and a hole is also provided at end of distal member 20d through which the pin 50 also extends. In the second set 21b, a pin 53 similarly extends through holes 233 through two openings in the sides of housing 150 near the distal end 152. Each of pins 50 and 53 are adjacent the one of windows 154a, 154b through which their respective tissue engaging member sets 21a and 21b are extendible and retractable.

As illustrated in FIG. 8, the end effector 48 also includes a plunger 30 disposed at least partially in the housing 150 at or adjacent to the distal end 152 of the housing 150, and the plunger 30 is longitudinally displaceable relative to the housing 150. In particular, a proximal end 158 of the plunger 30, which may correspond to (or be at or adjacent to) the proximal portion 148 of the end effector 48, may be coupled to the distal end 56 of the wire 52. The proximal end 158 of the plunger 30 may be coupled to the distal end 56 of the wire 52 in any suitable manner. For example, the distal end 56 of the wire 52 may include an enlarged portion 160 (such as a ball end) that is disposed within a cavity 162 formed in a portion of the plunger 30. Thus, a distal displacement of the distal end 56 of the wire 52 results in a distal displacement of the plunger 30 with respect to the housing 150, and a proximal displacement of the distal end 56 of the wire 52 results in a proximal displacement of the plunger 30 with respect to the housing 150. In addition, the enlarged portion 160 and the cavity 162 are shaped and dimensioned configured to allow the plunger 30 (and the entire housing 150) to rotate relative to the distal end 56 of the wire 52.

The plunger 30 additionally includes two plunger sockets 30c, 30d formed in a distal end 164 of the plunger 30. At end 49a opposite socket 33 of proximal member 20a forms a curved member or shaft 32a, and at end 49b opposite pin 42 of proximal member 20b forms a curved member or shaft 32b. For tissue engaging member set 21a, curved members 32a and 32b of proximal members 20a and 20b, respectively, are received beside each other in the plunger socket 30c and are rotatable therein. For tissue engaging member set 21b, curved members 32a and 32b of proximal members 20a and 20b, respectively, are received beside each other in the plunger socket 30d and are rotatable therein. The walls 30f forming the plunger sockets 30c and 30d extend upwards to form fingers with tapered ends. This facilitates insertion of curved members 32a and 32b in one of the plunger sockets 30c and 30d for respective tissue engaging member sets 21a and 21b, such that the curved members 32a and 32b may inserted or removed from these sockets only at an angle not achievable when the distal end is fully assembled, thereby preventing the curved members 32a and 32b from falling out of their respective sockets during normal operation.

Figure 6:
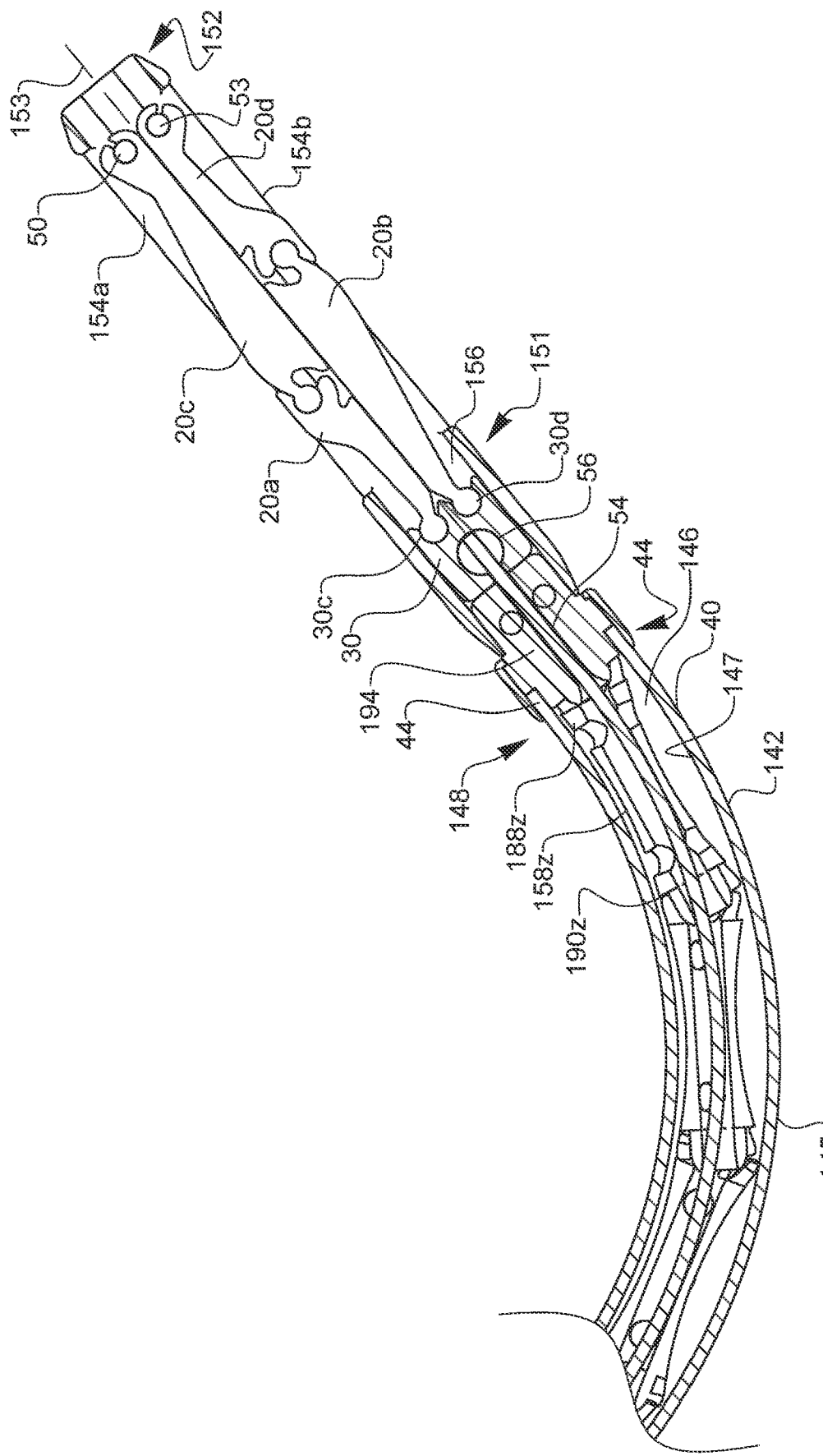
FIG. 6 is a cross-sectional view of a distal end of a shaft portion of the embodiment of the tissue manipulation device of FIG. 1 with the end effector in a first undeployed position.

As the plunger 30 moves distally in the housing 150 towards the distal end 152, the curved members 32a and 32b rotate in plunger socket 30c (for tissue engaging member set 21a) or 30d (for tissue engaging member set 21b), rotating curved members 36 and 42 of distal and proximal members 20c and 20b, respectively, in sockets 33 and 43 of proximal and distal members 20a and 20d, respectively, as distal members 20c and 20d rotate about pin 51 (for tissue engaging member set 21a) or 54 (for tissue engaging member set 21b), thereby extending outwards from the distal end 16 simultaneously both sets 21a and 21b of tissue engaging members 20. The degree of extension being controlled by the length of travel of the longitudinal drive mechanism and limited by fingers 34 and 44 of proximal and distal members 20a and 20d, respectively, being stopped by their full insertion into openings 37 and 45 of distal and proximal members 20c and 20b, respectively. As the plunger 30 moves towards the proximal end 151 of the housing 150, the above-described outward rotation of member 20a-d occurs in the opposite direction, thereby retracting the tissue engaging members 20. The degree of retracting may be controlled by the length of travel of the plunger 30 and limited by the surface 38a of barb 38 of proximal member 20a abutting the surface 23b of distal member 20c, and the surface 46a of barb 46 of distal member 20d abutting the surface 25 of proximal member 20b. When fully retracted, the tissue engaging members 20 are substantially contained in the housing 150, and may extend slightly beyond the outer perimeter of the housing 150, as shown in FIG. 6.

Accordingly, when a user rotates the adjustment member 22 relative to the handle portion 12 such that the adjustment member 22 translates distally, the securing member carrier 74 also moves distally, thereby translating the securing member 24 from the first securing member position 133 (illustrated in FIG. 4A) to the second securing member position 35 (illustrated in FIG. 4B). As the securing member 24 displaces from the first securing member position 133 to the second securing member position 35, the distal end 56 of the wire 52 is displaced distally, thereby moving the plunger 30 distally within the housing 150 of the end effector 48, and the end effector 48 is displaced from the first undeployed position 49 (illustrated in FIGS. 1 and 6) to the second deployed position 51 (illustrated in FIG. 8).

Conversely, when a user rotates the adjustment member 22 relative to the handle portion 12 such that the adjustment member 22 translates proximally, the securing member carrier 74 also moves proximally (as illustrated in FIG. 4B, due to the bias caused by the first end portion 99 of the resilient member 98 of the securing member 24 that is in contact with the stop post 96), thereby translating the securing member 24 from the second securing member position 35 (illustrated in FIG. 4B) to the first securing member position 133 (illustrated in FIG. 4A). As the securing member 24 displaces from the second securing member position 35 to the first securing member position 133, the distal end 56 of the wire 52 is displaced proximally, thereby moving the plunger 30 proximally within the housing 150 of the end effector 48, and the end effector 48 is displaced from the second deployed position 51 (illustrated in FIG. 8) to the first undeployed position 49.

While the embodiment of the end effector 48 has been described as having two sets 21a, 21b of two tissue engaging members 20 that are extendible from the first undeployed position 49 to the second deployed position 51, other embodiments of the end effector are contemplated. In some of the other embodiments, the end effector 48 may be configured to extend, retract, or change position from a first position to a second position (and, optionally, further positions). In other embodiments, the end effector 48 may have a fixed configuration and not transition from a first position to a second position, In some embodiments, the end effector 48 may be rotatable relative to the shaft portion 40 during a procedure, providing the user with an advantageous additional rotational degree of freedom. In such embodiments, the adjustment wheel 122, which may be disposed in the space between the proximal end 118 of the distal support portion 112 and the distal end 116 of the proximal support portion 110, may be coupled to the end effector 48 to rotate the end effector 48 relative to the shaft portion 140.

In particular, as illustrated in FIG. 2, the adjustment wheel 122 may have a central aperture 166 that may be adapted to be disposed around an outer surface 168 of a wheel hub 170. The central aperture 166 may have a non-circular shape that may correspond to a non-circular shape of the outer surface 168 of the wheel hub 170 such that when the adjustment wheel 122 is rotated, the wheel hub 170 correspondingly rotates relative to the handle portion 12 (and the shaft portion 40). The wheel hub 170 may be elongated and may extend along a hub axis from a proximal end 172 to a distal end 174, and the hub axis may be aligned with the longitudinal axis 14. So configured, and as illustrated in FIG. 4B, all or a portion of a proximal portion 176 of the wheel hub 170 may be disposed through (and may be rotatable within) the proximal support portion 110 of the wheel housing portion 108 of the handle portion 12, and all or a portion of a distal portion 178 of the wheel hub 170 may be disposed through (and may be rotatable within) the distal support portion 112 of the wheel housing portion 108 of the handle portion 12. The wheel hub 170 may be maintained in proper longitudinal alignment by a plurality of Belleville springs 180 that are disposed between a proximal surface of the distal support portion 112 and a surface of the adjustment wheel 122, which is fixed to the wheel hub 170.

Still referring to FIG. 4B, the wheel hub 170 may have a central aperture 171 that extends through the wheel hub 170 from the proximal end 172 to the distal end 174 along the hub axis, and the central aperture 171 is in communication with the central bore 64 of the handle portion 12 As such, a portion of the wire 52 may be disposed through, and may displace longitudinally within, the central aperture 171 of the wheel hub 170. A plurality of gear teeth 182 may be disposed about a circumferential surface at the distal end 174 of the wheel hub 170 surrounding the central aperture 171, and the plurality of gear teeth 182 rotate about the longitudinal axis 14 as the adjustment wheel 122 is rotated.

Figure 7:
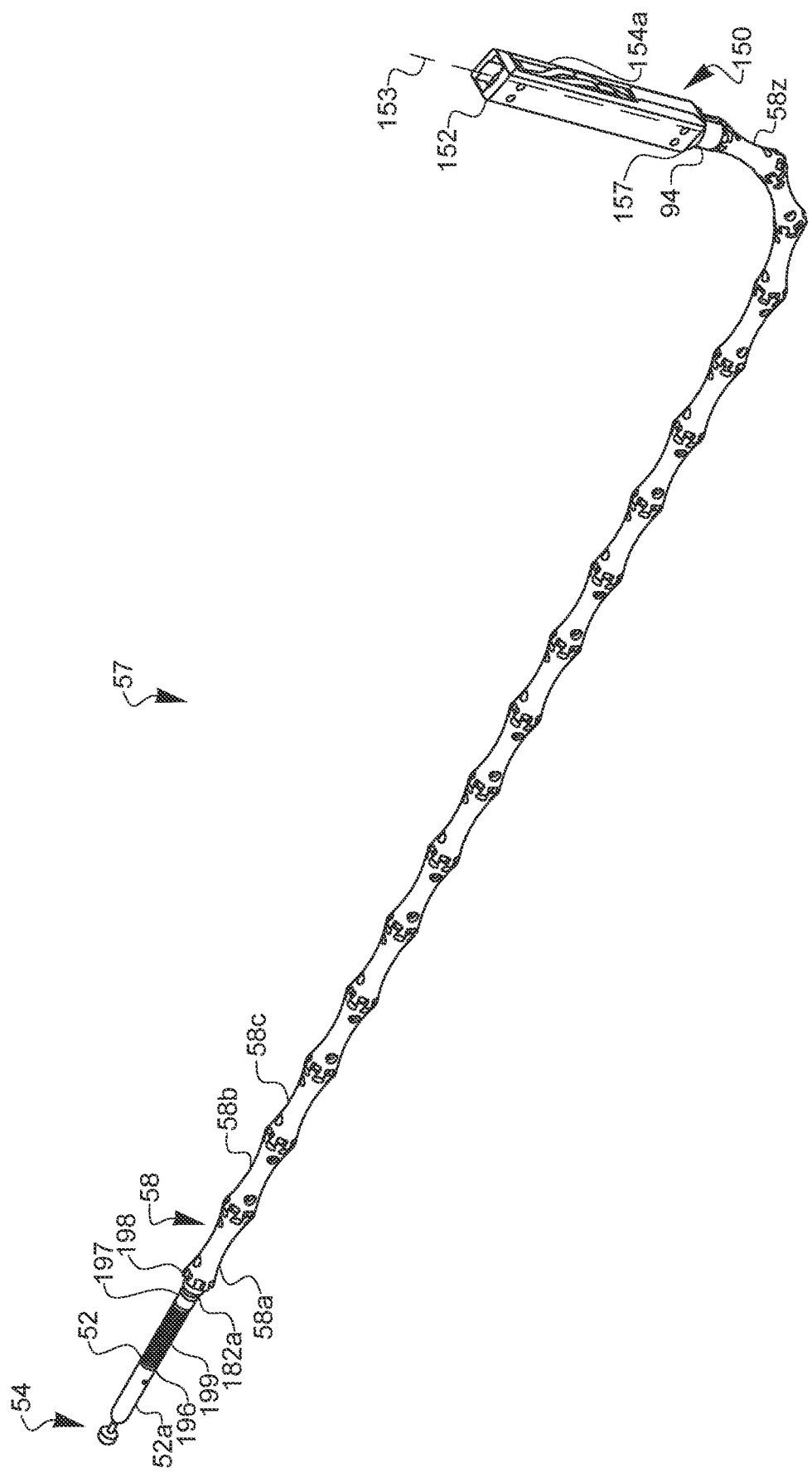
FIG. 7 is a perspective of an embodiment of a removable assembly of the tissue manipulation device of FIG. 1.

Referring now to FIG. 7, the removable portion 57 of the tissue manipulation device 10 may include two or more torque links 58 that cooperate to rotatably couple the adjustment wheel 122 and the end effector 48. The two or more torque links 58 may include a first torque link 58a that may be rotatably coupled to the wheel hub 170. In particular, as illustrated in FIG. 2, the first torque link 58a may be elongated and may extend along an axis from a proximal end 182a to a distal end 184a, and a link bore 186a may extend through the first torque link 58a from the proximal end 182a to the distal end 184a. As such, a portion of the wire 52 may be disposed through, and may displace longitudinally within, the link bore 186a. A plurality of gear teeth 188a may be disposed about a circumferential surface at the distal end 184a of the first torque link 58a surrounding the link bore 186a. In addition, a plurality of receiving notches 190a may be disposed about a circumferential surface at the proximal end 182a of the first torque link 58a surrounding the link bore 186a. When the removable portion 57 is secured to the handle portion 12 and the shaft portion 40 of the tissue manipulation device 10, and when the securing member 24 is in the engaged position 36 (illustrated in FIG. 4A), each of the plurality of receiving notches 190a of the first torque link 58a may engage a corresponding one of the plurality of gear teeth 182 of the wheel hub 170 such that a rotation of the wheel hub 170 causes a corresponding rotation of the first torque link 58a.

Each of the two or more torque links 58 of the removable portion 57 may be identical. For example, the two or more torque links 58 may also include a second torque link 58b that may be identical to the first torque link 58a. That is, the second torque link 58b may be elongated and may extend along an axis from a proximal end 182b to a distal end 184b, and a link bore 186b may extend through the second torque link 58b from the proximal end 182b to the distal end 184b. As such, a portion of the wire 52 may be disposed through, and may displace longitudinally within, the link bore 186b. A plurality of gear teeth 188b may be disposed about a circumferential surface at the distal end 184b of the second torque link 58b surrounding the link bore 186b. In addition, a plurality of receiving notches 190b may be disposed about a circumferential surface at the proximal end 182b of the second torque link 58b surrounding the link bore 186b. When the removable portion 57 is secured to the handle portion 12 and the shaft portion 40 of the tissue manipulation device 10, and when the securing member 24 is in the engaged position 36 (illustrated in FIG. 4A), the second torque link 58b may be disposed distal to the first torque link 58a such that each of the plurality of gear teeth 188a of the first torque link 58a may engage a corresponding one of the plurality of receiving notches 190b of the second torque link 58b such that a rotation of the first torque link 58a causes a corresponding rotation of the second torque link 58b.

In some embodiments, the removable portion 57 may include any number of additional torque links 58, which may include the most distal torque link 58z. Distal torque link 58z may be identical to the first and second torque links 58a, 58b, and all other included torque links 58. As such, when the first torque link 58a is rotated by a corresponding rotation of the adjustment wheel 122, the second torque link 58b is also rotated as previously described, and the chain reaction of rotation would also rotate the distal torque link 58z. When the distal torque link 58z rotates, the gear teeth 188z of the distal torque link 58z also rotate, as would be understood by one having ordinary skill in the art. The gear teeth 188z of the distal torque link 58z engage corresponding receiving notches 192 on a proximal end of a connector portion 194 of the end effector 48. The connector portion 194 is fixedly coupled to the housing 150 of the end effector 48, and when the distal torque link 58z rotates from rotation of the adjustment wheel 122 as previously described, the end effector 40 also rotates relative to the shaft portion 40 about the end effector axis 153.

In some embodiments, the two or more torque links 58 include only two torque links, so the second torque link 58b corresponds to the distal torque link 58z. In other embodiments, the orientation of the on the gear teeth 188a and the receiving notches 190a previously described may be reversed. For example, the proximal end 182 of the first torque link 58a may have the gear teeth 188a and the distal end 184a of the first torque link 58a may include the receiving notches 190a, and all other torque links 58 and associated components may also be reversed. In other embodiments, the gear teeth 188a and the receiving notches 190a may be identical features such that the orientation of the torque links 58 along the wire 52 of the removable portion 57 does not matter.

As illustrated in FIG. 7, the removable portion 57 may include the two or more torque links 58 (for example, sixteen torque links 58), and a portion of the wire 52 may extend through the link bore 186 of each of the two or more torque links 58. In some embodiments, the removable portion 57 may also include a spring 196 that may surround a portion of the wire 52, and the spring may extend from a proximal end 197 to a distal end 198 along an axis aligned with the portion of the wire 52. The proximal end 197 of the spring 196 may be coupled to a portion of the wire 52 adjacent to the proximal end 54 of the wire 52, such as a distal end of the coupling portion 52a disposed at or adjacent to the proximal end 54 of the wire 52.

The distal end 198 of the spring 196 may be directly or indirectly coupled to the proximal end 182a of the first torque link 58a. In some embodiments, the distal end 198 of the spring 196 may be coupled to a proximal end of a cylindrical member 199, and the distal end of the cylindrical member 199 may be in contact with a portion of the proximal end 182a of the first torque link 58a. So positioned, the spring 195 operates to bias the first torque link 58a towards the distal end 56 of the wire 52, which biases the distal end 184a of the first torque link 58a into engagement with the proximal end 182b of the second torque link 58b, which similarly biases each of the remaining torque links 58 distally such that the gear teeth 188z at the distal end 184z of the distal torque link 58z is biased into engagement with the corresponding receiving notches 192 on the proximal end of the connector portion 194 of the end effector 48.

Accordingly, when the securing member 24 is pivoted from the engaged position 36 (illustrated in FIG. 4A) to the disengaged position 39 (illustrated in FIG. 5), the removable portion 57 may be removed from the shaft portion 40 and handle portion 12. In some embodiment, a locking mechanism (not shown), such as a pin extending through an aperture, may couple the end effector 48 to the distal end 44 of the shaft portion 40, and this locking mechanism should be disabled (e.g., by removing the pin) prior to removing the removable portion 57. Once the end effector 48 is no longer secured to the distal end 44 of the shaft portion 40, the end effector 48 may be grasped by a user and displaced along the end effector axis 153 away from the distal end 44 of the shaft portion 40 until a proximal end 200 of the removable portion 57, which may be the proximal end 54 of the wire 52, extends past the distal end 44 of the shaft portion 40. One having ordinary skill in the art would recognize that the removable portion 57 would be bendable between any two adjacent torque links 58, and this ability to bend allows the chain of torque links 58 allows the removable portion 57 to be passed through the curved portion 142 of the shaft portion 40 when inserting or removing the removable portion 57 for disassembly or reassembly.

Once the removable portion 57 has been removed from the handle portion 12 and shaft portion 40, the handle portion 12 and shaft portion 40 may undergo a process (e.g., washing and sterilization). Alternatively, the removable portion 57 may also be processed separately from, or instead of, the handle portion 12 and shaft portion 40. To reattach the removable portion 57, or to attach a new removable portion 57, the described steps are reversed.

Figure 11:
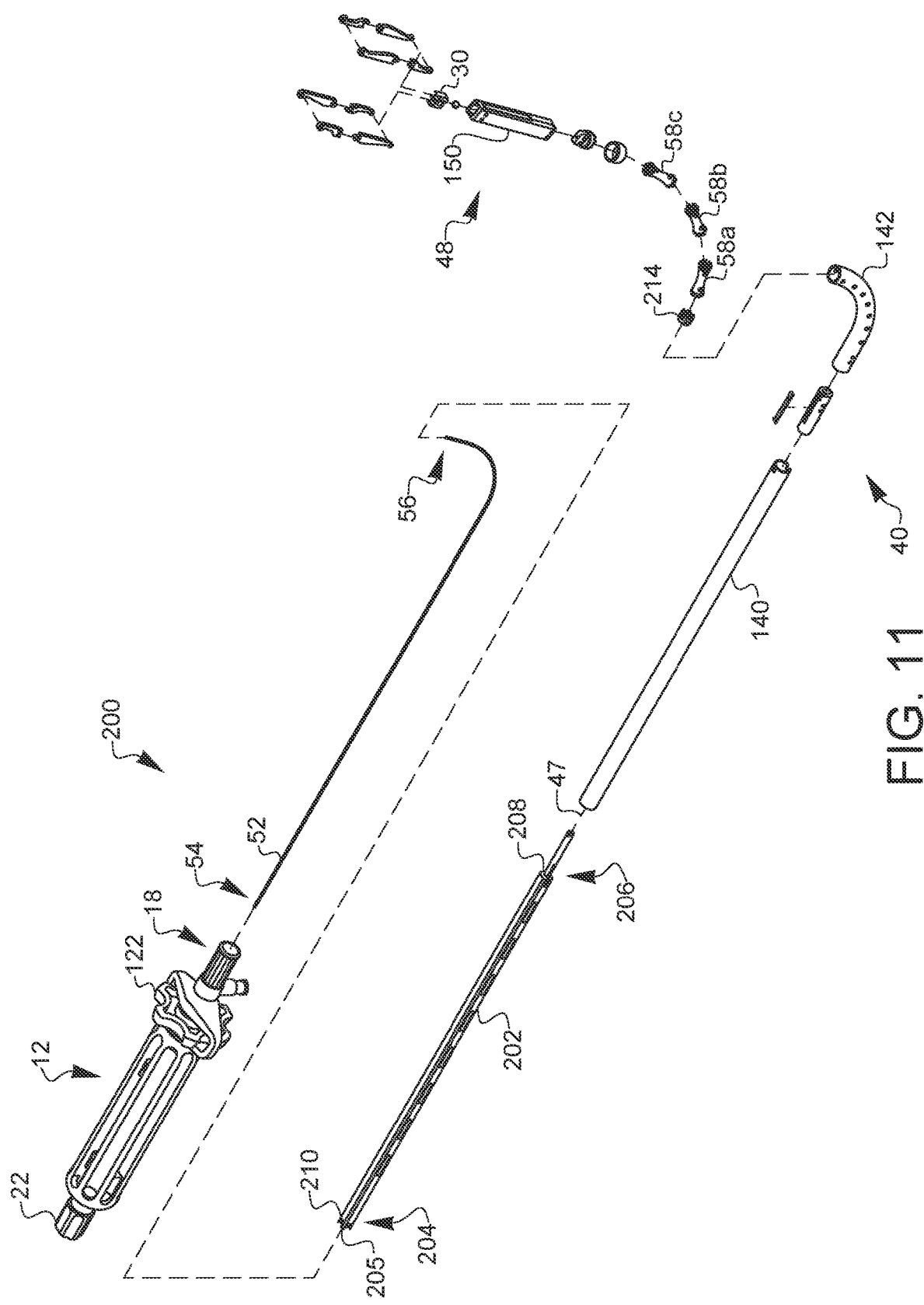
FIG. 11 is an exploded view of a portion of a further embodiment of the tissue manipulation device.
Figure 12:
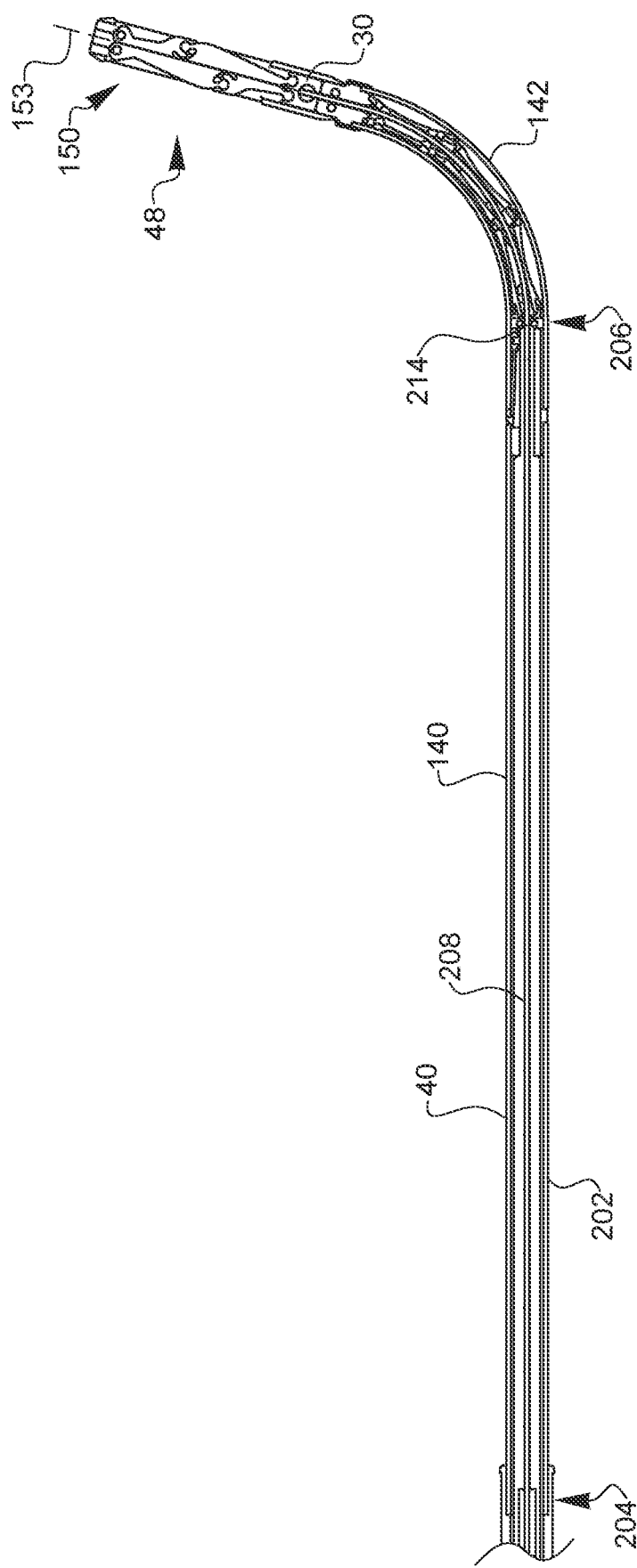
FIG. 12 is a cross-sectional view of a shaft portion of the embodiment of the tissue manipulation device of FIG. 11.
Figure 13:
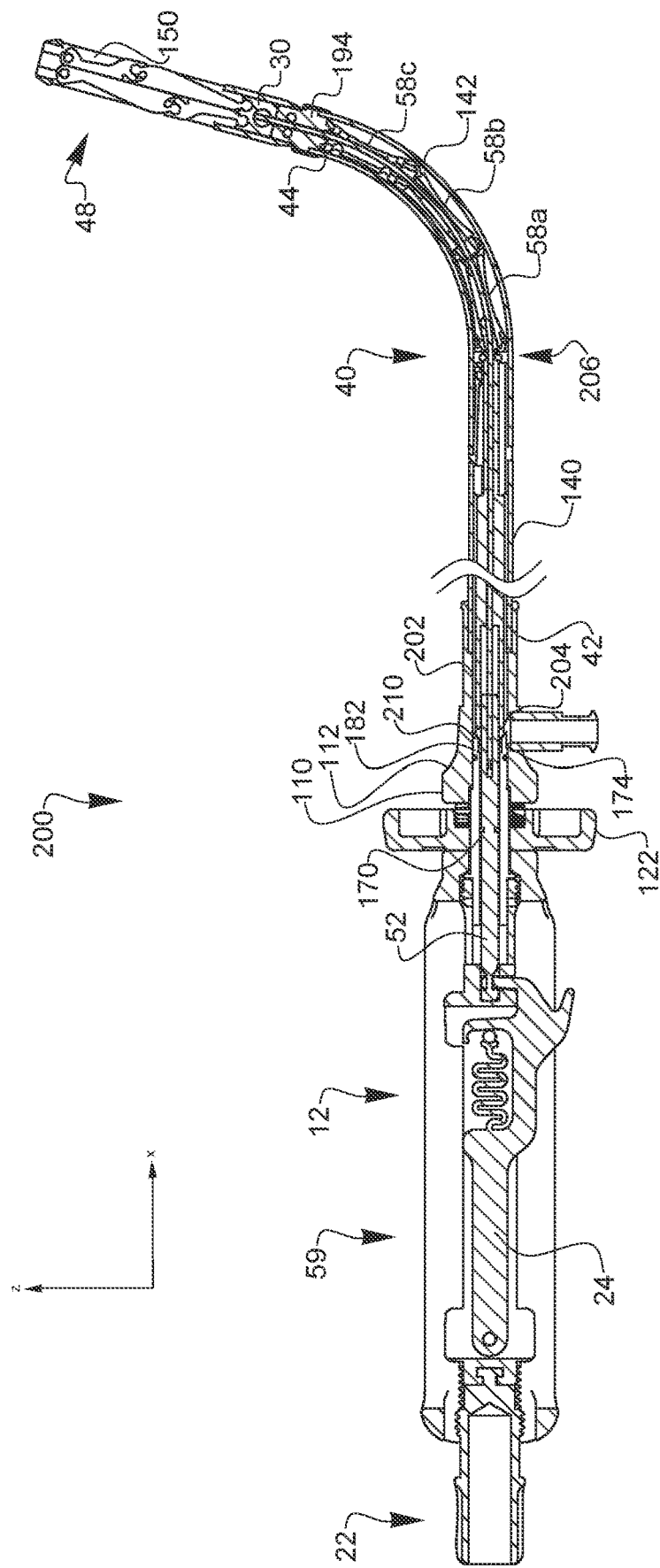
FIG. 13 is a cross-sectional view of the embodiment of the tissue manipulation device of FIG. 11.

Turning to a further embodiment illustrated in FIGS. 11 to 13, the tissue manipulation device 200 may be substantially identical to the tissue manipulation device 10 previously described, with the exception that a rigid torque member 202 may replace one or more of the torque links 58. In particular, the torque member 202 may extend along an axis 205 from a proximal end 204 to a distal end 206, and the axis 205 may be aligned with the portion of the shaft axis 47 that extends along the linear portion 140 of the shaft portion 40. The torque member 202 may include a central bore 208 that extends through the torque member 202 from the proximal end 204 to the distal end 206 along the axis 205. The torque member may have any suitable cross-sectional shape or combination of shapes to allow the torque member 202 to transmit torque and to fit in the linear portion 140 of the shaft portion 40.

The torque member 202 may be a single, unitary part or may be an assembly of two or more components that cooperate to form the torque member 202. In operation, a portion of the wire 52 may be disposed through, and be longitudinally displaceable within, the central bore 208 of the torque member 202. In some embodiments, a guide sheath (not shown) may surround all or a portion of the portion of the wire 52 that extends through the central bore 208 of the torque member 202.

A plurality of receiving notches 210 may be disposed about a circumferential surface at the proximal end 204 of the torque member 202 surrounding the central bore 208. When the securing member 24 is in the engaged position 36 (illustrated in FIG. 13), each of the plurality of receiving notches 210 of the torque member 202 may engage a corresponding one of the plurality of gear teeth 182 of the wheel hub 170 such that a rotation of the wheel hub 170 causes a corresponding rotation of the torque member 202 about the axis 205.

The torque member 202 may extend distally such that the distal end 206 of the torque member 202 is disposed at or adjacent to the intermediate point 144 of the shaft portion 140, which is at a distal end of the distal end of the linear portion 140 of the shaft portion 40 and at a proximal end of the of the curved portion 142 of the shaft portion 40. A plurality of gear teeth 212 may be disposed about a circumferential surface at the distal end 204 of the torque member 202 surrounding the central bore 208. The plurality of gear teeth 212 may be disposed on a removable end portion 214 that forms the distal end 206 of the torque member 202. The plurality of gear teeth 212 may engage a first of two or more torque links 58 that may be identical to those previously described, and the two or more torque links 58 may be disposed in the curved portion 142 of the shaft portion 140. As such, each of the plurality of gear teeth 212 at the distal end 204 of the torque member 202 may engage a corresponding one of the plurality of receiving notches 190a of the first torque link 58a such that a rotation of the torque member 202 causes a corresponding rotation of the first torque link 58a. The rotation of the first torque link 58a causes a corresponding rotation of the second torque line 58b (and any additional torque links 58) to rotate the end effector 48 relative to the distal end 44 of the shaft portion 40.

Advantageously, the torque member 202 efficiently transmits a torque applied to the proximal end 204 of the torque member 202 to the distal end 206 of the torque member 202 without rotational lag, allowing for precise rotational control and more immediate response when a user rotates the adjustment wheel 122.

Figure 5:
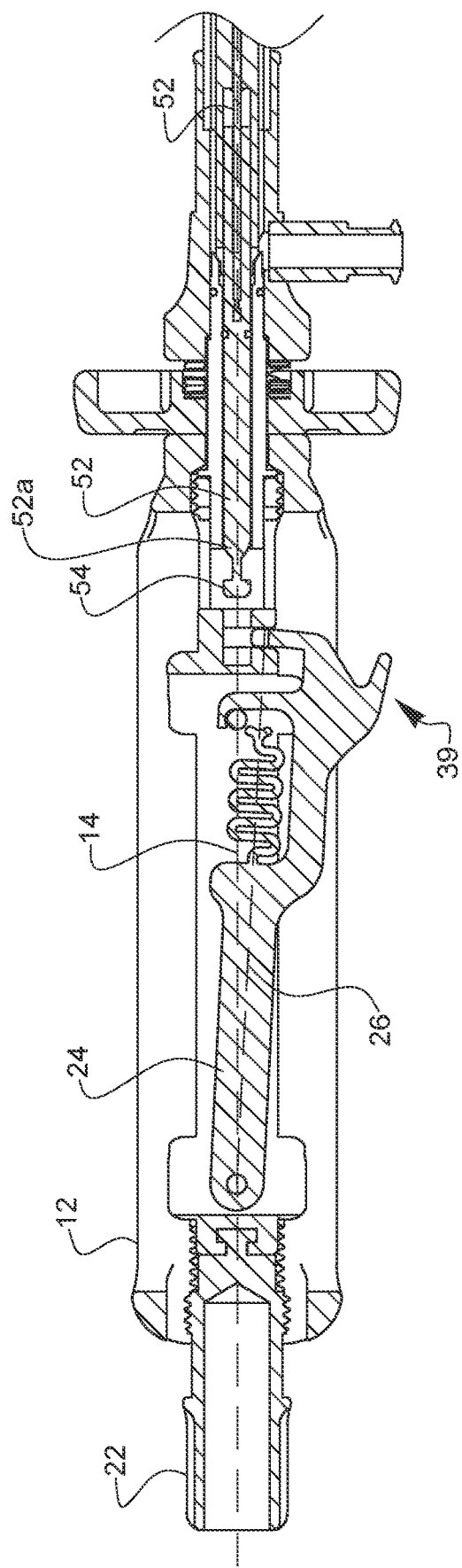
FIG. 5 is a cross-sectional view of the embodiment of the tissue manipulation device of FIG. 1 with the securing member in a disengaged position.

In some embodiments, the torque member 202 may not be a portion of the removable portion 57 that may be removed through the distal end 44 of the shaft portion 40 as a unit when the securing member 24 is pivoted from the engaged position 36 (illustrated in FIG. 4A) to the disengaged position 39 (illustrated in FIG. 5). However, in other embodiments, the torque member 202 may be a portion of the removable portion 57, and the proximal end 204 of the torque member 202 may be disposed adjacent to the proximal end 54 of the wire 52 or adjacent to a portion of the coupling portion 52a, In such an embodiment, a feature (not shown) coupled to or formed on the wire 52 (or coupling portion 52a) may prevent the proximal end 204 of the torque member 202 from displacing beyond the proximal end 54 of the wire 52 when the removable portion 57 is removed through the distal end 44 of the shaft portion 40.

For example, FIGS. 16 to 18D illustrate an embodiment of a removable portion 300 that may include an embodiment of a torque member 302. In this embodiment, the torque member 302 may extend along an axis 304 from a proximal end 306 to a distal end 308, and the axis 304 may be aligned with the portion of the shaft axis 47 that extends along the linear portion 140 of the shaft portion 40 (see FIG. 10A). The axis 304 may also be parallel to or aligned with (in an unbent or linear configuration) with the X-axis of the reference coordinate system of FIGS. 16 and 17A. The torque member 302 may be configured to transmit torque that is input at the proximal end 306 to the output end 308 when the torque member 302 is rotated about the axis 304. The torque member 302 may also be configured to allow for bending of the torque member 302 about an axis that is normal to the axis 304 such that the torque member 302 may bend only in a first bending plane, thereby allowing the torque member 302 to efficiently transmit torque without lag or loss from slop, while allowing one or more portions of the torque member 302 to selectively bend when the removable portion 300 to be passed through the curved portion 142 of the shaft portion 40 when inserting or removing the removable portion 300 for disassembly or reassembly.

Figure 16:
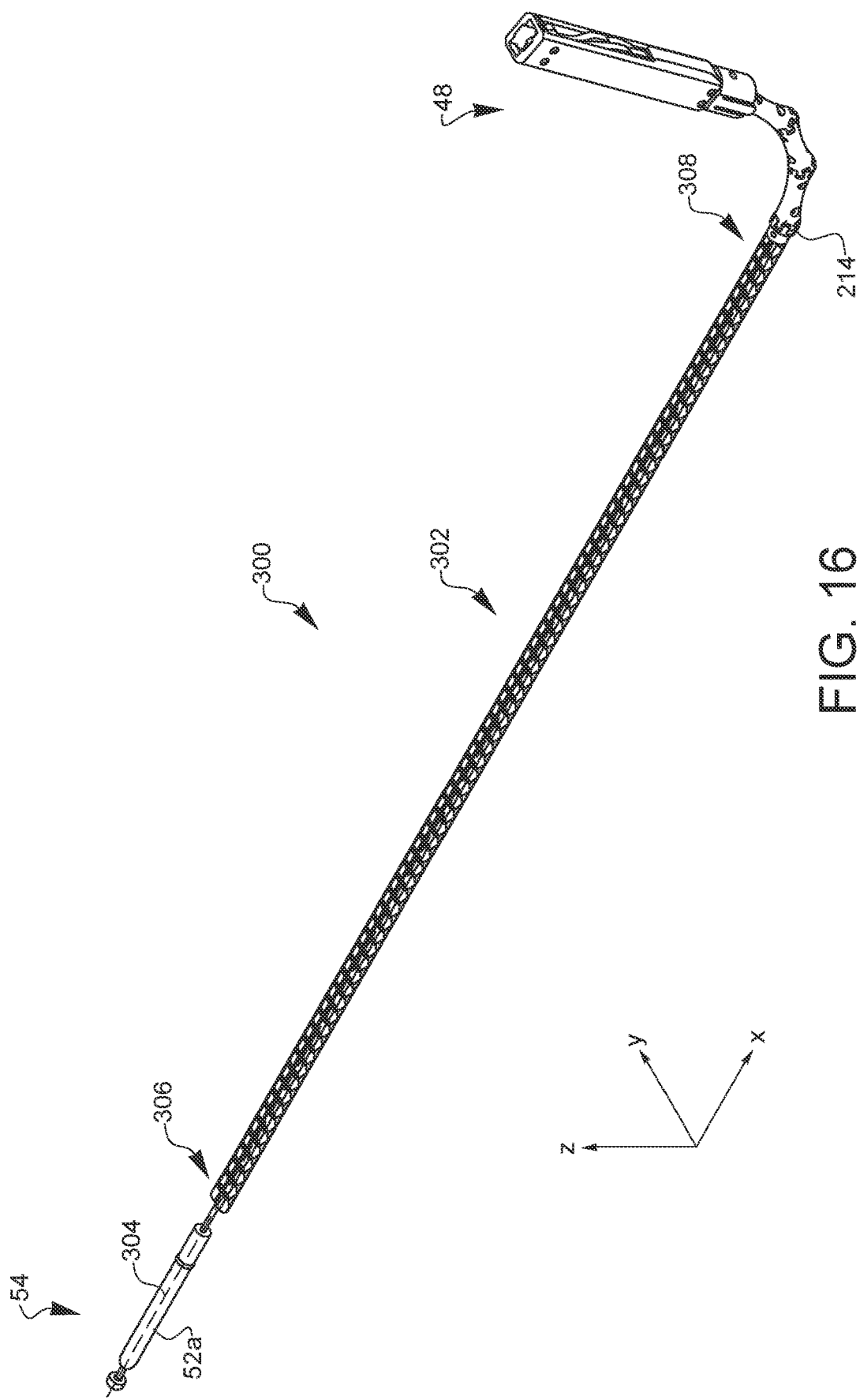
FIG. 16 is a perspective view of an embodiment of the removable portion of an embodiment of the tissue manipulation device.
Figure 17C:
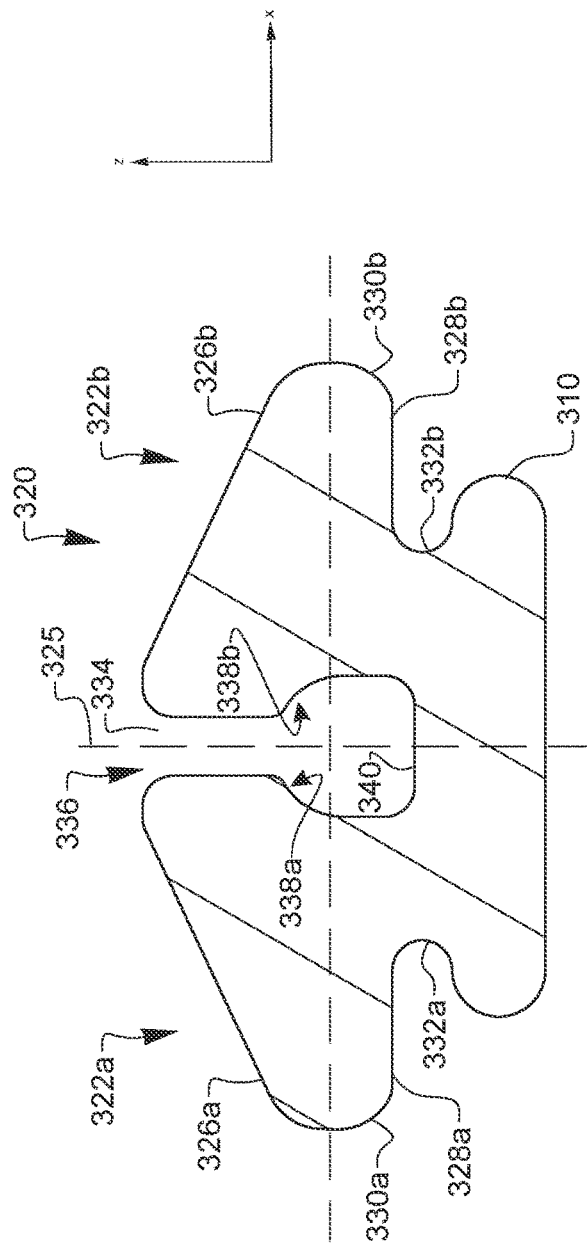
FIG. 17C is a cross-sectional view of the embodiment of the torque member taken along section line 17C-17C in FIG. 17A.
Figure 17E:
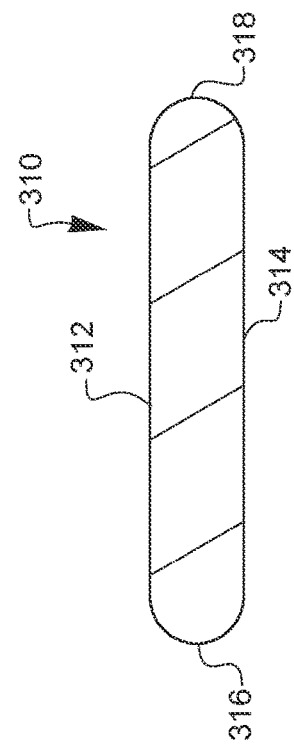
FIG. 17E is a cross-sectional view of the embodiment of the torque member taken along section line 17E-17E in FIG. 17A.
Figure 17D:
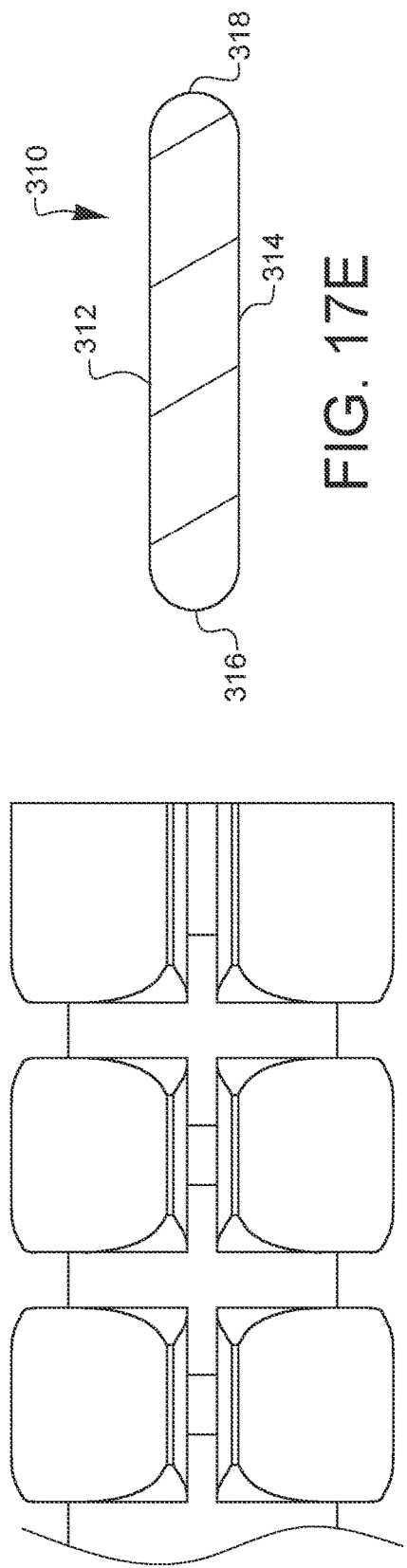
FIG. 17D is top view of a portion of the torque member of the removable portion of the embodiment of the tissue manipulation device of FIG. 16.

Turning to FIG. 17A, the torque member 302 may include a base 310 that extends from the proximal end 306 to the distal end 308. The base 310 may have a constant cross-sectional shape along the length of the torque member 302. As illustrated in FIG. 17E, the cross-sectional shape of the base 310 (when viewed along the axis 304) may be defined by an upper edge 312 and a lower edge 314 that is parallel to and offset from the upper edge 312. Each of the upper edge 312 and a lower edge 314 may be parallel to the Y-axis of the reference coordinate system of FIGS. 16 and 17C. The cross-sectional shape of the base 310 may be further defined by a first lateral edge 316 and a second lateral edge 318. The first lateral edge 316 may extend along or substantially along the Z-axis of the reference coordinate system of FIGS. 16 and 17C from a first end of the upper edge 312 to a first end of the lower edge 314. The second lateral edge 318 may extend along or substantially along the Z-axis of the reference coordinate system of FIGS. 16 and 17C from a second end of the upper edge 312 to a second end of the lower edge 314. Each of the first lateral edge 316 and the second lateral edge 318 may be curved to partially curved to form a segment of a circle, for example.

A plurality of projections 320 may extend from the base 310, and each of the plurality of projections 320 may be spaced along the X-axis of the reference coordinate system of FIGS. 16 and 17C from an adjacent other of the plurality of projections 320. The plurality of projections 320 may extend along the entire length of the base 310 from the proximal end 306 to the distal end 308 of the torque member 302. In other embodiments, the plurality of projections 320 may extend along one or more portions of the length of the base 310. When viewed in cross-section (along the axis 304), as illustrated in FIG. 17C, each of the plurality of projections 320 may be include a first projection portion 322*a* and a second projection portion 322*b*, and the first projection portion 322*a* and the second projection portion 322*b* may be symmetrically formed about a plane 325, which is parallel to the X-Z plane of the reference coordinate system of FIGS. 16 and 17C, and the plane 325 may extend along the axis 304. The first projection portion 322*a* may be defined by an upper projection edge 326*a* and a lower projection edge 328*a*. The lower projection edge 238*a* may extend along or generally along the Y-axis of the reference coordinate system of FIGS. 16 and 17C, and the upper projection edge 326*a* may be obliquely disposed (or downwardly sloped) towards the lower projection edge 328*a* as the upper projection edge 326*a* extends away from the plane 325. A lateral edge 330*a* may extend between a first end of the upper projection edge 326*a* and a first end of the lower projection edge 328*a*, and the lateral edge 330*a* may be at least partially curved or rounded. As such, the upper projection edge 326*a*, the lower projection edge 328*a*, and the lateral edge 330*a* may cooperate to generally form shape of a wedge. A second lateral edge 332*a* may extend from a second end of the lower projection edge 328*a* to a first portion of the upper edge 312 of the base 310, and the second lateral edge 332*a* may be least partially curved or rounded.

The second projection portion 322*b* may be a mirror image of the first projection portion 322*a* and may be symmetrical to the first projection portion 322*a* about the plane 325. In particular, the second projection portion 322*b* may be defined by an upper projection edge 326*b* and a lower projection edge 328*b*. The lower projection edge 238*b* may extend along or generally along the Y-axis of the reference coordinate system of FIGS. 16 and 17C, and the upper projection edge 326*b* may be obliquely disposed (or downwardly sloped) towards the lower projection edge 328*b* as the upper projection edge 326*b* extends away from the plane 325. A lateral edge 330*b* may extend between a first end of the upper projection edge 326*b* and a first end of the lower projection edge 328*b*, and the lateral edge 330*b* may be curved or rounded. As such, the upper projection edge 326*b*, the lower projection edge 328*b*, and the lateral edge 330*b* may cooperate to generally form shape of a wedge. A second lateral edge 332*b* may extend from a second end of the lower projection edge 328*b* to a second portion of the upper edge 312 of the base 310, and the second lateral edge 332*a* may be least partially curved or rounded.

Each of the plurality of projections 320 may also include a wire bore 334 from a proximal end of each of the plurality of projections 320 to a distal end of each of the plurality of projections 320. Each of the wire bores 334 in each of the plurality of projections 320 may be aligned or generally aligned with the other plurality of projections 320 over the length of the axis 304 such that, in operation, a corresponding portion of the wire 52 may be disposed through, and be longitudinally displaceable within, the wire bore 334 of each of the plurality of projections 320. The wire bore 334 may have any suitable shape to receive the corresponding portion of the wire 52. For example, the wire bore 334 may be a substantially U-shaped notch 336 formed between the first projection portion 322*a* and the second projection portion 322*b*, and the notch may extend through and along the plane 325. The notch may have a first lateral portion 338*a* that extends downwardly from a second end of the upper projection edge 326*a* of the first projection portion 322*a* and a second lateral portion 338*b* that extends downwardly from a second end of the upper projection edge 326*b* of the second projection portion 322*b*. A notch end edge 340 may extend (e.g., extend parallel to or generally parallel to the Y-axis of the reference coordinate system of FIGS. 16 and 17C) between an end of the first lateral portion 338*a* and an end of the second lateral portion 338*b*.

With reference to FIG. 17A, each of the plurality of projections 320 may be spaced along the X-axis of the reference coordinate system of FIGS. 16 and 17C from an adjacent other of the plurality of projections 320. For example, a first 320*a* of the plurality or projections 320 may have a distal lateral edge 342*a* that may be disposed a first distance D1 along the X-axis from a proximal lateral edge 344*b* of a second 320*b* of the plurality or projections 320. The second 320*a* of the plurality or projections 320 may have a distal lateral edge 342*b* that may be disposed a second distance D2 along the X-axis from a proximal lateral edge 344*c* of a third 320*c* of the plurality or projections 320. In some embodiments, the first distance D1 may be equal to the second distance D2. In some embodiments, the distance along the X-axis between a distal lateral edge 342*x* of any of the plurality of projections 320 from a proximal lateral edge 344*x* of an adjacent one of the plurality or projections 320 may be the first distance D1.

As illustrated in FIG. 17A, when viewed along the Y-axis of the reference coordinate system, a first neck edge 346 and a second neck edge 348 extends obliquely towards the base 310 to form a narrowed neck portion 350 that upwardly extends from the base 310. The spacing between the first and second adjacent plurality of projections 320, as well as the combination of cross-sectional shapes of each of the plurality of projections 320, allow the torque member 302 to bend along an axis that is parallel to the Y-axis of the reference coordinate system of FIGS. 16 and 17A, that this axis may be normal to the plane 325. Thus, any portion of the torque member 302 may bend clockwise or counterclockwise about the axis when viewed along the Y-axis, as shown in FIG. 17A. Thus, rotation is allowed in a single bending plane (plane 325), but not along any other planes or along any axis that is not parallel to the Y-axis of the reference coordinate system of FIGS. 16 and 17A. This ensure sufficient rigidity of the torque member 302 when the torque member 302 is rotated about the X-axis of the reference coordinate system of FIGS. 16 and 17A while allowing the torque member 302 to bend within a single plane to allow for insertion or extraction of the removable portion 300 through the curved portion 142 of the shaft portion 40.

As illustrated in FIGS. 18A to 18D, the torque member 302 may also include one or more alignment features 352 that ensures that the removable portion 300 is oriented correctly when inserted into the distal end 44 of the shaft portion 40 during the assembly (or reassembly) of the tissue manipulating device 10. The one or more alignment features 352 may include a protrusion 356 formed at or adjacent to the distal end 354 of the linear portion 140 of the shaft portion 40 or at or adjacent to the proximal end of the curved portion 142 of the shaft portion 40. The protrusion 356 may be formed as a depression (e.g., a dome-shaped depression) in the shaft portion 40 and the depression may extend into the shaft interior portion 146. In some embodiments, the depression may be a dome-shaped depression that may be symmetrically formed or disposed about a plane that extends through the shaft axis 47 and is parallel to the X-Z of the reference coordinate system of FIGS. 1 and 18D, and the depression may be formed on an upper surface of the shaft portion 40, wherein the direction "upper" corresponds to the direction along the Z-axis in which the curved portion 142 of the shaft portion 40 extends.

The alignment feature 352, such as the depression, may be positioned to not contact a portion of the upper projection edges 326a, 326b of the first projection portion 322a or the second projection portion 322b of the torque member 302 when the removable portion 300 is positioned correctly for insertion. However, when the removable portion 300 is positioned incorrectly upon insertion into the shaft portion 40, the alignment feature 352 may contact a portion of the sloped upper projection edges 326a, 326b of the first projection portion 322a or the second projection portion 322b to rotate the torque member 302, and the entire removable portion 300, into correct alignment to allow for the curving of the torque member 302 upon insertion into the shaft portion 40. FIG. 18C illustrates various orientations of the torque member 302 relative to the alignment feature 352 within the shaft portion 40.

Figure 19E:
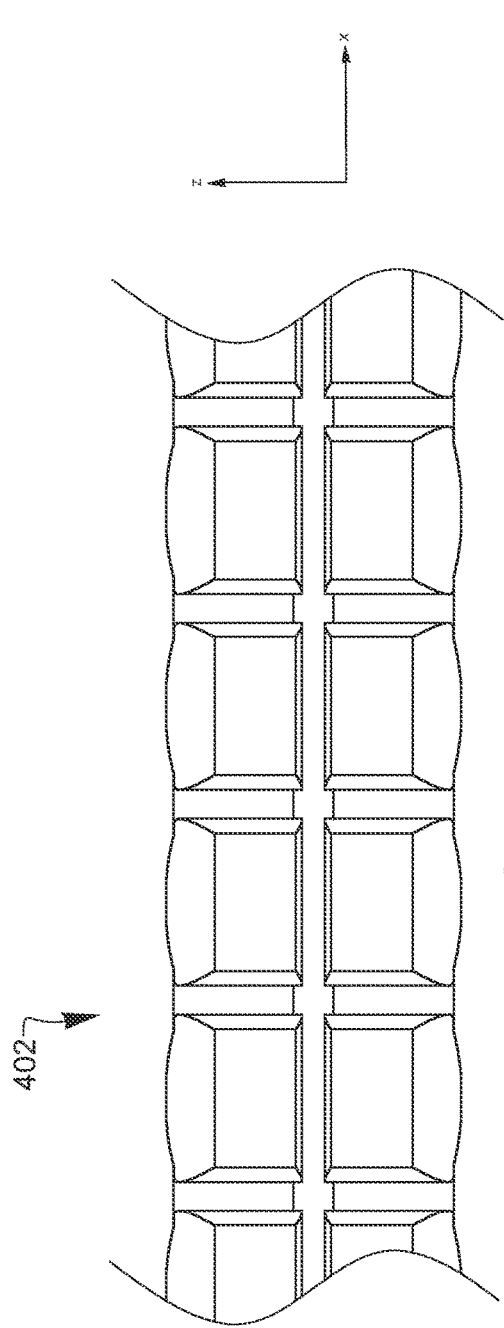
FIG. 19E is top view of a portion of the torque member of the removable portion of the embodiment of the tissue manipulation device of FIG. 19A.
Figure 19F:
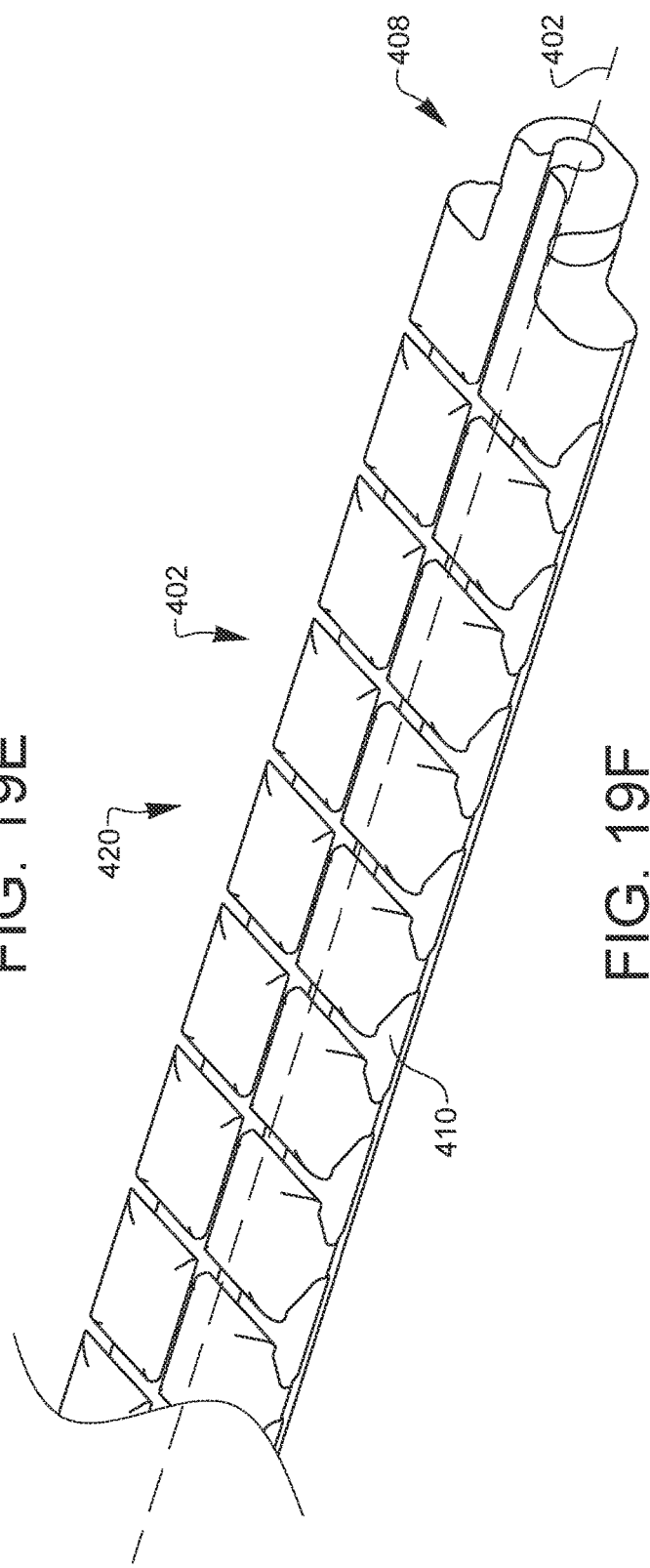
Figure 19I:
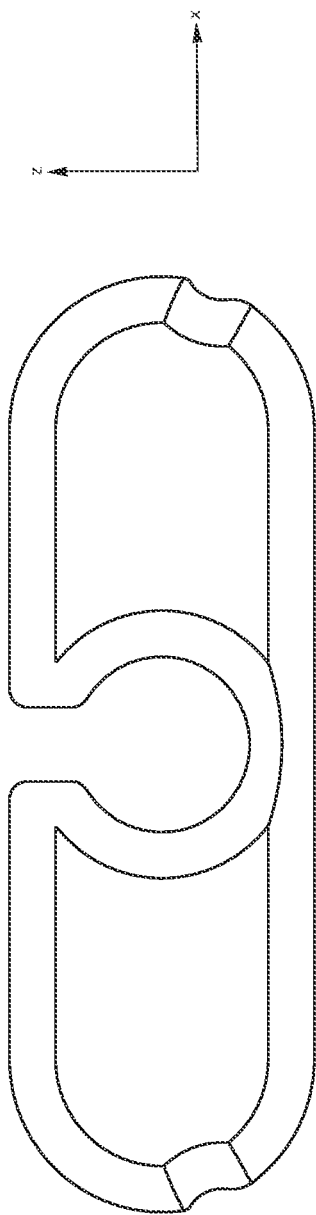
FIG. 19I is a front view of the torque member of the removable portion of the embodiment of the tissue manipulation device of FIG. 19A.
Figure 19J:
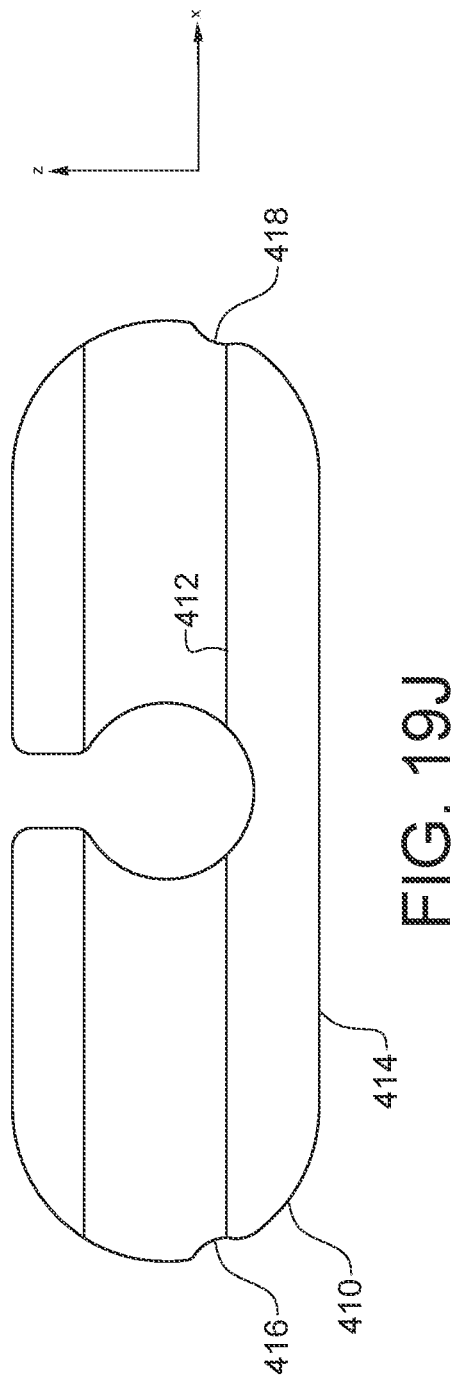
FIG. 19J is a cross-sectional view of the embodiment of the torque member taken along section line 19J-17J in FIG. 17K.
Figure 19K:
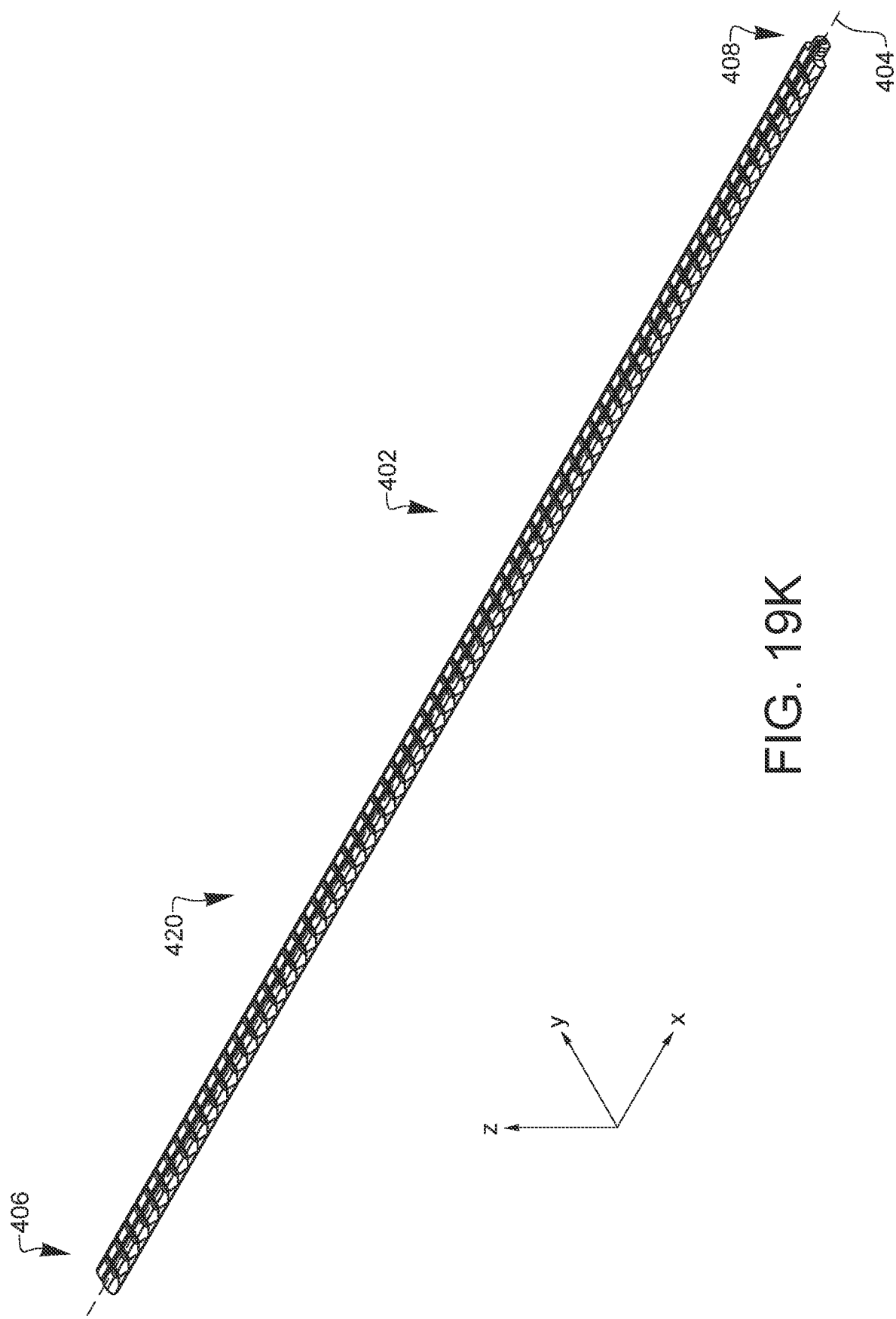
FIG. 19K is a perspective view of the embodiment of the torque member of the removable portion of FIG. 19A.

FIGS. 19A to 19K illustrate a further embodiment of a removable portion 400 that may include an embodiment of a torque member 402 that may be similar to, but have a slightly different cross-sectional shape from, the torque member 302 illustrated in FIGS. 16 to 18D. As illustrated in FIG. 19K, the torque member 402 may extend along an axis 404 from a proximal end 406 to a distal end 408, and the torque member 402 may include a base 410 that extends from the proximal end 406 to the distal end 408. The base 410 may have a constant cross-sectional shape along the length of the torque member 402. As illustrated in FIG. 19J, the cross-sectional shape of the base 410 (when viewed along the axis 404) may be defined by an upper edge 412 and a lower edge 314 that is parallel to and offset from the upper edge 412. Each of the upper edge 412 and a lower edge 414 may be parallel to the Y-axis of the reference coordinate system of FIG. 19J. The cross-sectional shape of the base 410 may be further defined by a first lateral edge 416 and a second lateral edge 418. The first lateral edge 416 may extend along or substantially along the Z-axis of the reference coordinate system of FIG. 19J from a first end of the upper edge 412 to a first end of the lower edge 414. The second lateral edge 418 may extend along or substantially along the Z-axis of the reference coordinate system of FIG. 19J from a second end of the upper edge 412 to a second end of the lower edge 414. Each of the first lateral edge 416 and the second lateral edge 418 may be curved, contoured, or partially curved.

A plurality of projections 420 may extend from the base 410, and each of the plurality of projections 420 may be spaced along the X-axis of the reference coordinate system of FIG. 19D from an adjacent other of the plurality of projections 420. The plurality of projections 420 may extend along the entire length of the base 410 or may extend along one or more portions of the length of the base 410. When viewed in cross-section (along the axis 404), as illustrated in FIG. 19C, each of the plurality of projections 420 may be include a first projection portion 422a and a second projection portion 422b, and the first projection portion 422a and the second projection portion 422b may be symmetrically formed about a plane 425, which is parallel to the X-Z plane of the reference coordinate system of FIGS. 19C and 19D, and the plane 425 may extend along the axis 404. The first projection portion 422a may be defined by an upper projection edge 426a which may extend along or generally along the Y-axis of the reference coordinate system of FIG. 19C, and a lateral edge 430a may extend between a first end of the upper projection edge 326a and a first end of the base 410 (e.g., a first end of the upper edge 412 of the base 410), and the lateral edge 430a may be at least partially curved or rounded. The second projection portion 422b may be a mirror image of the first projection portion 422a and may be symmetrical to the first projection portion 422a about the plane 425. In particular, the second projection portion 422b may be defined by an upper projection edge 426b which may extend along or generally along the Y-axis of the reference coordinate system of FIG. 19C, and a lateral edge 430b may extend between a first end of the upper projection edge 426b and a second end of the base 410 (e.g., a second end of the upper edge 412 of the base 410), and the lateral edge 430b may be at least partially curved or rounded.

Each of the plurality of projections 420 may also include a wire bore 434 that from a proximal end of each of the plurality of projections 420 to a distal end of each of the plurality of projections 420. Each of the wire bores 434 in each of the plurality of projections 420 may be aligned or generally aligned with the other plurality of projections 420 over the length of the axis 404 such that, in operation, a corresponding portion of the wire 52 may be disposed through, and be longitudinally displaceable within, the wire bore 434 of each of the plurality of projections 420. The wire bore 434 may have any suitable shape to receive the corresponding portion of the wire 52. For example, the wire bore 434 may be a substantially U-shaped notch 436 formed between the first projection portion 422a and the second projection portion 422b, and the notch 436 may extend through and along the plane 425. The notch 436 may have a first lateral portion 438a that extends downwardly from a second end of the upper projection edge 426a of the first projection portion 422a and a second lateral portion 438b that extends downwardly from a second end of the upper projection edge 426b of the second projection portion 422b. A notch bottom edge 440 may extend between an end of the first lateral portion 438a and an end of the second lateral portion 438b, and the notch bottom edge 440 may have the shape of a segment of a circle.

With reference to FIG. 19D, each of the plurality of projections 420 may be spaced along the X-axis of the reference coordinate system of FIGS. 19D and 19K from an adjacent other of the plurality of projections 420. For example, a first 420a of the plurality or projections 420 may have a distal lateral edge 442a that may be disposed a first distance D1 along the X-axis from a proximal lateral edge 444b of a second 420b of the plurality or projections 420. The second 420a of the plurality or projections 420 may have a distal lateral edge 442b that may be disposed a second distance D2 along the X-axis from a proximal lateral edge 444c of a third 420c of the plurality or projections 420. In some embodiments, the first distance D1 may be equal to the second distance D2. In some embodiments, the distance along the X-axis between a distal lateral edge 442x of any of the plurality of projections 420 from a proximal lateral edge 444x of an adjacent one of the plurality or projections 420 may be the first distance D1.

As illustrated in FIG. 19D, when viewed along the Y-axis of the reference coordinate system, a first neck edge 446 and a second neck edge 448 extends obliquely towards the base 410 to form a narrowed neck portion 450 that extends upward from the base 410. The spacing between the first and second adjacent plurality of projections 420, as well as the combination of cross-sectional shapes of each of the plurality of projections 420, allow the torque member 402 to bend along an axis that is parallel to the Y-axis of the reference coordinate system of FIGS. 19C and 19D, that this axis may be normal to the plane 425. Thus, any portion of the torque member 402 may bend clockwise or counterclockwise about the axis when viewed along the Y-axis, as shown in FIG. 19D. Thus, rotation is allowed in a single bending plane (plane 425), but not along any other planes or along any axis that is not parallel to the Y-axis of the reference coordinate system of FIG. 19D. This ensures sufficient rigidity of the torque member 402 when the torque member 402 is rotated about the X-axis of the reference coordinate system of FIGS. 19D and 19K while allowing the torque member 402 to bend within a single plane to allow for insertion or extraction of the removable portion 400 through the curved portion 142 of the shaft portion 40.

FIGS. 20A to 20F illustrate a further embodiment of a removable portion 500 that may include an embodiment of a torque member 502 that may be similar to, but have a different cross-sectional shape from, the torque member 302 illustrated in FIGS. 16 to 18D and the torque member 402 illustrated in FIGS. 19A to 19K. As illustrated in FIG. 19A, the torque member 502 may extends along an axis 504 from a proximal end 506 to a distal end 508, and the torque member 502 may include a base 510 that extends from the proximal end 506 to the distal end 508, and the base 510 may be similar to the base 410 of base 310 previously described.

A plurality of projections 520 may extend from the base 510, and each of the plurality of projections 520 may be spaced along the X-axis of the reference coordinate system of FIG. 20A from an adjacent other of the plurality of projections 420, in a manner similar or identical to the plurality of projections 420 or the plurality of projections 320 previously described. Each of the plurality of projections may have a rectangular of square (or substantially rectangular or square) cross-sectional shape, as illustrated in FIG. 20F. Each of the plurality of projections 520 may also include a wire bore 534 that extends from a proximal end of each of the plurality of projections 520 to a distal end of each of the plurality of projections 520. Each of the wire bores 534 in each of the plurality of projections 520 may be aligned or generally aligned with the other plurality of projections 520 over the length of the axis 504 such that, in operation, a corresponding portion of the wire 52 may be disposed through, and be longitudinally displaceable within, the wire bore 534 of each of the plurality of projections 520. The wire bore 534 may have any suitable shape to receive the corresponding portion of the wire 52. For example, the wire bore 534 may be cylindrical and may have an axis that extends parallel to the X-axis of the reference coordinate system of FIG. 20C. In cross-section, the wire bore 534 may have a circular edge 540 that may be symmetrically disposed about a plane 525 that is parallel to the X-Z plane of the reference coordinate system of FIG. 20A, and the plane 525 may extend along the axis 504.

With reference to FIG. 20C, each of the plurality of projections 520 may be spaced along the X-axis of the reference coordinate system of FIG. 20C from an adjacent other of the plurality of projections 520 in a manner identical to that of the plurality of projections 420 or the plurality of projections 320 previously described. The spacing between the first and second adjacent plurality of projections 520, as well as the combination of cross-sectional shapes of each of the plurality of projections 520, allow the torque member 502 to bend along an axis that is parallel to the Y-axis of the reference coordinate system of FIG. 20A, that this axis may be normal to the plane 525. Thus, any portion of the torque member 502 may bend clockwise or counterclockwise about the axis when viewed along the Y-axis, as shown in FIG. 20C. Thus, rotation is allowed in a single bending plane (plane 525), but not along any other planes or along any axis that is not parallel to the Y-axis of the reference coordinate system of FIG. 20A. As previously explained, this ensures sufficient rigidity of the torque member 502 when the torque member 502 is rotated about the X-axis of the reference coordinate system of FIG. 20A while allowing the torque member 502 to bend within a single plane to allow for insertion or extraction of the removable portion 500 through the curved portion 142 of the shaft portion 40.

The torque member 202 may be comprised of any suitable material or combination of materials, such as plastic or stainless steel.

Turning now to the embodiment illustrated in FIGS. 21A to 24B, a tissue engaging assembly 600 may be used instead of the tissue engaging members 20 of the end effector 48 illustrated in FIGS. 8, 11, and 12. In particular, the tissue engaging assembly 600 may be used in an embodiment of an end effector assembly 602 illustrated in FIGS. 25 to 26C, and the embodiment of the end effector assembly 602 will be described in more detail below. The embodiment of the end effector assembly 602 may be used in the embodiment of the tissue manipulation device 10 previously described or in any other embodiment of a tissue manipulation device, and the end effector assembly 602 may rotate or otherwise displace relative to the distal end 44 of the shaft portion 40 as previously described.

The tissue engaging assembly 600 may be a single, unitary part that may allow for two or more tissue engaging arms 604 that may be deployable to secure and/or displace a patient's prostate during a procedure. This single part may be manufactured or produced in any suitable manner, such as by injection molding the part using a plastic material. Similar to the end effector 48, the end effector assembly 602 may be displaced from a first undeployed position 603 (illustrated in FIG. 25) to a second deployed position 605 (illustrated in FIGS. 26A to 26C). For example, the end effector assembly 602 may be in the first undeployed position 603 to be inserted into the urethra of a patient, then the end effector assembly 602 may be transitioned to the second deployed position 605 when positioned within a portion of the patent's prostate, allowing the surgeon to physically manipulate or position the prostate as desired. When it is desired to remove the end effector assembly 602, the end effector assembly 602 may be transitioned back to the first undeployed position 603 and removed from the urethra.

Figure 25:
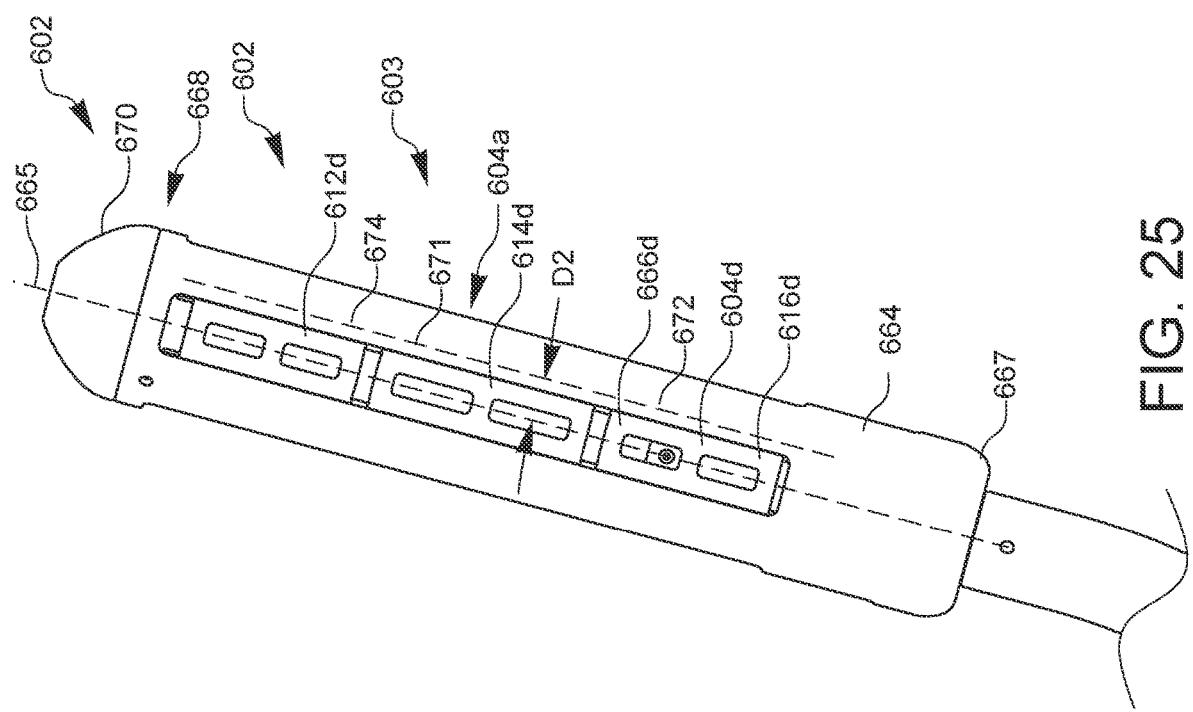
FIG. 25 is a side view of an embodiment of an end effector assembly that includes the embodiment of the tissue engaging assembly of FIGS. 21A and 21B with the end effector assembly in a first undeployed position.
Figure 26B:
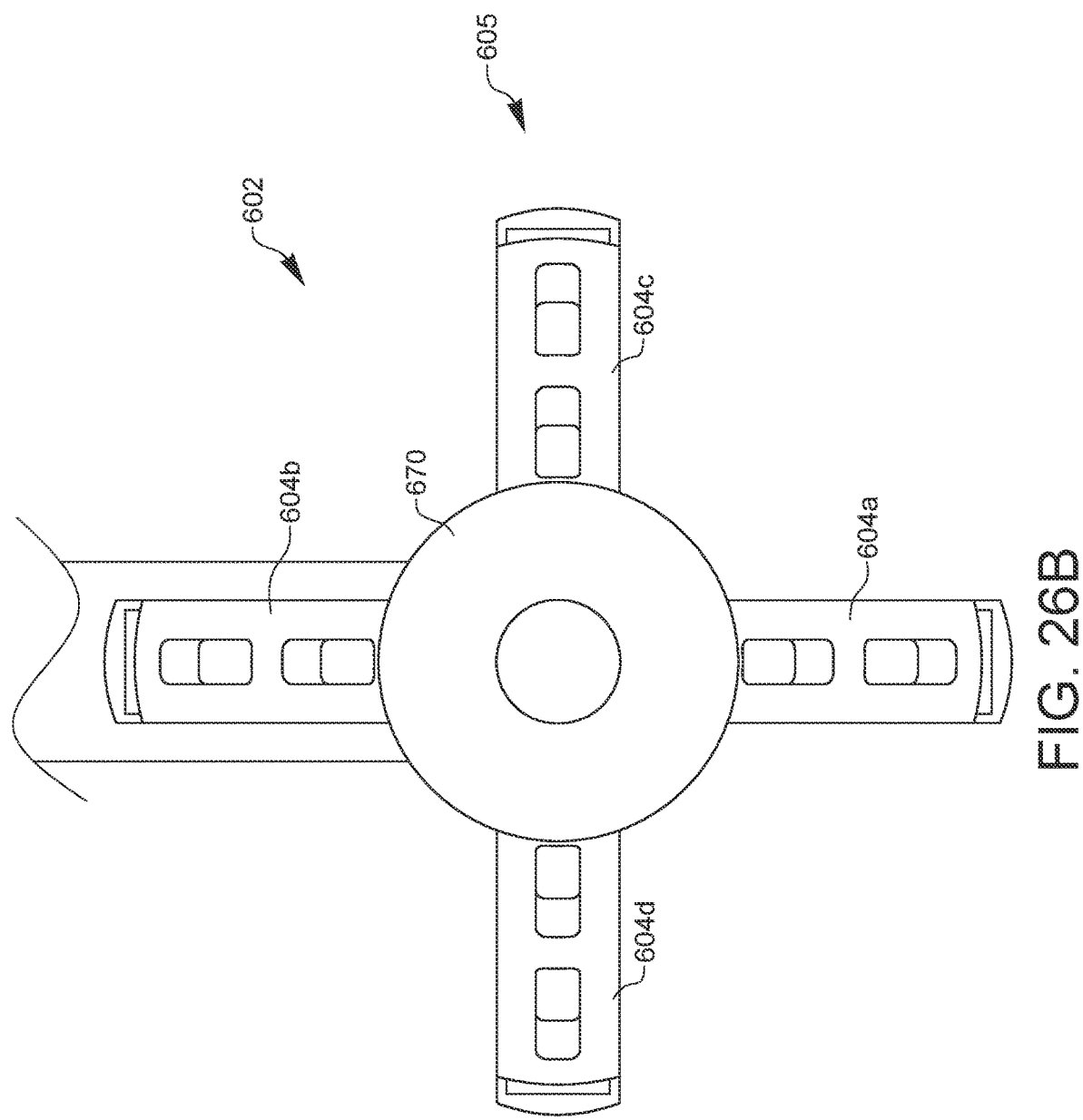

Turning to 21A to 24B, the tissue engaging assembly 600 may include two, three, four, or more tissue engaging arms 604. For example, the tissue engaging assembly 600 may include four tissue engaging arms 604, which includes a first tissue engaging arm 604a, a second tissue engaging arm 604b, a third tissue engaging arm 604c, and a fourth tissue engaging arm 604d. FIGS. 21A to 22C illustrates the pre-assembled configuration of the tissue engaging assembly 600, such as the configuration of the tissue engaging assembly 600 after injection molding and before assembly or integration into the end effector assembly 602 as illustrated in FIGS. 25 to 27. With reference to FIG. 22A, the first tissue engaging arm 604a may be elongated and may extend from a first end 606a to a second end 608a along a first arm axis 610a that may be parallel to (or aligned with) the X-axis of the reference coordinate system of FIG. 22A, and the first end 606a may be coupled to a first portion 611a of a hub portion 611. The first tissue engaging arm 604a may include two or more arm segments, and in some embodiments, the first tissue engaging arm 604a may include a first arm segment 612a, a second arm segment 614a, and a third arm segment 616a.

Referring to FIG. 24A, the first arm segment 612a of the first tissue engaging arm 604a may extend from a first end 618a to a second end 620a along the first arm axis 610a. The first end 618a of the first arm segment 612a may be adjacent to (or may correspond to) the first end 606a of the first tissue engaging arm 604a, and the first end 618a may be coupled to (and be adjacent to and offset from) the first portion 611a of the hub portion 611. The first end 618a of the first arm segment 612a may be coupled to the first portion 611a of the hub portion 611 in any suitable manner, such as with a first hinge 622a. The first hinge 622a may be a living hinge that may extend between the first end 618a of the first arm segment 612a and the first portion 611a of the hub portion 611.

The first arm segment 612a may have any cross-sectional shape or combination of shapes (when viewed along the first arm axis 610a) from the first end 618a to the second end 620a. For example, as illustrated in FIG. 24B, the first arm segment 612a may have a constant or substantially constant cross-sectional shape (when viewed along the first arm axis 610a) from the first end 618a to the second end 620a, and the cross-sectional shape of first arm segment 612a may have a polygonal shape. The cross-sectional shape of the first arm segment 612a may be partially defined by a pair of opposed lateral edges 615a, 617a that may be parallel (or generally parallel) and extend along (or generally along) the Z-axis of the reference coordinate system of FIGS. 22A and 24B. The cross-sectional shape of the first arm segment 612a may also be partially defined by a pair of inner lateral edges 619a, 621a that each extends from an end of corresponding one of the pair of opposed lateral edges 615a, 617a, and the pair of inner lateral edges 619a, 621a converge along the Z-axis to form a V-shape.

The second arm segment 614a of the first tissue engaging arm 604a may extend from a first end 625a to a second end 626a along the first arm axis 610a, and the first end 625a may be adjacent to (and offset from) the second end 620a of the first arm segment 612a. The first end 625a of the second arm segment 614a may be coupled to the second end 620a of the first arm segment 612a in any suitable manner, such as with a second hinge 627a. The second hinge 627a may be a living hinge that may extend between the first end 625a of the second arm segment 614a and the second end 620a of the first arm segment 612a. The cross-sectional shape of the second arm segment 614a may be identical or substantially identical to the cross-sectional shape of the first arm segment 612a.

The third arm segment 616a may extend from a first end 628a to a second end 629a along the first arm axis 610a, and the first end 628a may be adjacent to (and offset from) the second end 626a of the second arm segment 614a. The first end 628a of the third arm segment 616a may be coupled to a second end 626a of the second arm segment 614a in any suitable manner, such as with a third hinge 630a. The third hinge 630a may be a living hinge that may extend between the first end 628a of the third arm segment 616a and the second end 626a of the second arm segment 614a. The second end 629a of the third arm segment 616a may be coupled to a portion of the first end cap segment 632a in any suitable manner, such as with a fourth hinge 633a. The fourth hinge 633a may be a living hinge that may extend between the second end 629a of the third arm segment 616a and the portion of the first end cap segment 632a. The cross-sectional shape of the second arm segment 614a may be identical or substantially identical to the cross-sectional shape of the first arm segment 612a and/or the second arm segment 614a.

When the end effector assembly 602 is displaced from the first undeployed position 603 (illustrated in FIG. 25) to the second deployed position 605 (illustrated in FIGS. 26A to 26C) in a manner that will be described in more detail below, a first mating feature 632a of the first arm segment 612a (or one or more portions of the first mating feature 632a of the first arm segment 612a) may engage a corresponding first mating feature 634a of the second arm segment 614a (or a corresponding one or more portions of the first mating feature 634a of the second arm segment 614a) to maintain the first arm segment 612a and the second arm segment 614a in a desired position when the end effector assembly 602 is in the second deployed position 605. For example, as illustrated in FIG. 23, the first mating feature 632a of the first arm segment 612a may include a first notch 636a that may be configured to receive a first protrusion 638a of the first mating feature 634a of the second arm segment 614a. A forward contact surface 640a may define a portion of the first protrusion 638a, and the forward contact surface 640a may be configured to contact an oblique contact surface 642a that defines a portion of the first notch 636a when the end effector assembly 602 is displaced to the second deployed position 605.

The forward contact surface 640a of the first protrusion 638a may be planar and may be normal or substantially normal to the first arm axis 610a when the end effector assembly 602 is in the first undeployed position 603. The oblique contact surface 642a of the first notch 636a may be planar and may be disposed at an oblique angle relative to the first arm axis 610a when the end effector assembly 602 is in the first undeployed position 603. Accordingly, when the end effector assembly 602 is displaced to the second deployed position 605 such that the first arm segment 612a bends, rotates, or pivots relative to the second arm segment 614a (and/or vice versa) about the second hinge 627a, the planar surface of the forward contact surface 640a of the first protrusion 638a comes into contact with the planar oblique contact surface 642a of the first notch 636a to prevent further bending of the first arm segment 612a and the second arm segment 614a about the second hinge 627a.

The first mating feature 632a of the first arm segment 612a may also include a pair of end surfaces 644a that may also partially define the first notch 636a and the second end 620a of the first arm segment 612a. Further, the first mating feature 634a of the second arm segment 614a may include a pair of lateral oblique contact surfaces 646a that may also partially define the first protrusion 638a and extend from the first end 625a (and towards the second end 626a) of the second arm segment 614a. In some embodiments, the pair of lateral oblique contact surfaces 646a may be symmetrically disposed about the first protrusion 638a such that a first of the pair of lateral oblique contact surfaces 646a may be on a first lateral side of the first protrusion 638a and a second of the pair of lateral oblique contact surfaces 646a may be on a second lateral side of the first protrusion 638a.

The pair of end surfaces 644a of the first mating feature 632a of the first arm segment 612a may be planar and may be normal or substantially normal to the first arm axis 610a when the end effector assembly 602 is in the first undeployed position 603. The lateral oblique contact surface 646a of the first mating feature 634a of the second arm segment 614a may be planar and may be disposed at an oblique angle relative to the first arm axis 610a when the end effector assembly 602 is in the first undeployed position 603. Accordingly, when the end effector assembly 602 is displaced to the second deployed position 605 such that the first arm segment 612a bends, rotates, or pivots relative to the second arm segment 614a (and/or vice versa) about the second hinge 627a, the planar pair of end surfaces 644a comes into contact with the planar lateral oblique contact surfaces 646a to prevent further bending of the first arm segment 612a and the second arm segment 614a about the second hinge 627a. In some embodiments, the planar pair of end surfaces 644a comes into contact with the planar lateral oblique contact surfaces 646a at the same position as the forward contact surface 640a of the first protrusion 638a comes into contact with the planar oblique contact surface 642a of the first notch 636a to provide maximum resistance against further bending of the first arm segment 612a and the second arm segment 614a about the second hinge 627a when the end effector assembly 602 is displaced into the second deployed position 605.

In addition, when the end effector assembly 602 is displaced from the first undeployed position 603 (illustrated in FIG. 25) to the second deployed position 605 (illustrated in FIGS. 26A to 26C), a second mating feature 648a of the second arm segment 614a (or one or more portions of the second mating feature 648a of the second arm segment 614a) may engage a corresponding first mating feature 650a of the third arm segment 616a (or a corresponding one or more portions of the first mating feature 650a of the third arm segment 616a) to maintain the third arm segment 616a and the second arm segment 614a in a desired position when the end effector assembly 602 is in the second deployed position 605. For example, as illustrated in FIG. 23, the first mating feature 650a of the third arm segment 616a may include a first notch 652a that may be configured to receive a second protrusion 654a of the second mating feature 648a of the second arm segment 614a. A forward contact surface 656a may define a portion of the second protrusion 654a, and the forward contact surface 656a may be configured to contact an oblique contact surface 658a that defines a portion of the first notch 652a of the first mating feature 650a of the third arm segment 616a when the end effector assembly 602 is displaced to the second deployed position 605.

The forward contact surface 656a of the second protrusion 654a may be planar and may be normal or substantially normal to the first arm axis 610a when the end effector assembly 602 is in the first undeployed position 603. The oblique contact surface 658a of the first notch 652a of the first mating feature 650a of the third arm segment 616a may be planar and may be disposed at an oblique angle relative to the first arm axis 610a when the end effector assembly 602 is in the first undeployed position 603. Accordingly, when the end effector assembly 602 is displaced to the second deployed position 605 such that the third arm segment 616a bends, rotates, or pivots relative to the second arm segment 614a (and/or vice versa) about the third hinge 630a, the planar surface of the forward contact surface 656a of the second protrusion 654a comes into contact with the oblique contact surface 658a of the first notch 652a of the first mating feature 650a of the third arm segment 616a to prevent further bending of the third arm segment 616a and the second arm segment 614a about the third hinge 630a.

The first mating feature 650a of the third arm segment 616a may also include a pair of end surfaces 660a that may also partially define the first notch 652a and the first end 628a of the third arm segment 616a. Further, the second mating feature 648a of the second arm segment 614a may include a pair of lateral oblique contact surfaces 662a that may also partially define the second protrusion 654a and extend from the second end 626a (and towards the first end 625a) of the second arm segment 614a. In some embodiments, the pair of lateral oblique contact surfaces 662a may be symmetrically disposed about the second protrusion 654a such that a first of the pair of lateral oblique contact surfaces 662a may be on a first lateral side of the second protrusion 654a and a second of the pair of lateral oblique contact surfaces 662a may be on a second lateral side of the second protrusion 654a.

The pair of end surfaces 660a of the first mating feature 650a of the third arm segment 616a may be planar and may be normal or substantially normal to the first arm axis 610a when the end effector assembly 602 is in the first undeployed position 603. The lateral oblique contact surface 662a of the second mating feature 648a of the second arm segment 614a may be planar and may be disposed at an oblique angle relative to the first arm axis 610a when the end effector assembly 602 is in the first undeployed position 603. Accordingly, when the end effector assembly 602 is displaced to the second deployed position 605 such that the third arm segment 616a bends, rotates, or pivots relative to the second arm segment 614a (and/or vice versa) about the third hinge 630a, the planar pair of end surfaces 660a comes into contact with the planar lateral oblique contact surfaces 662a to prevent further bending of the third arm segment 616a and the second arm segment 614a about the third hinge 630a. In some embodiments, the planar pair of end surfaces 660a comes into contact with the planar lateral oblique contact surfaces 662a at the same position as the forward contact surface 656a of the second protrusion 654a comes into contact with the planar oblique contact surface 658a of the first notch 652a to provide maximum resistance against further bending of the third arm segment 616a and the second arm segment 614a about the third hinge 630a when the end effector assembly 602 is displaced into the second deployed position 605.

Figure 21B:
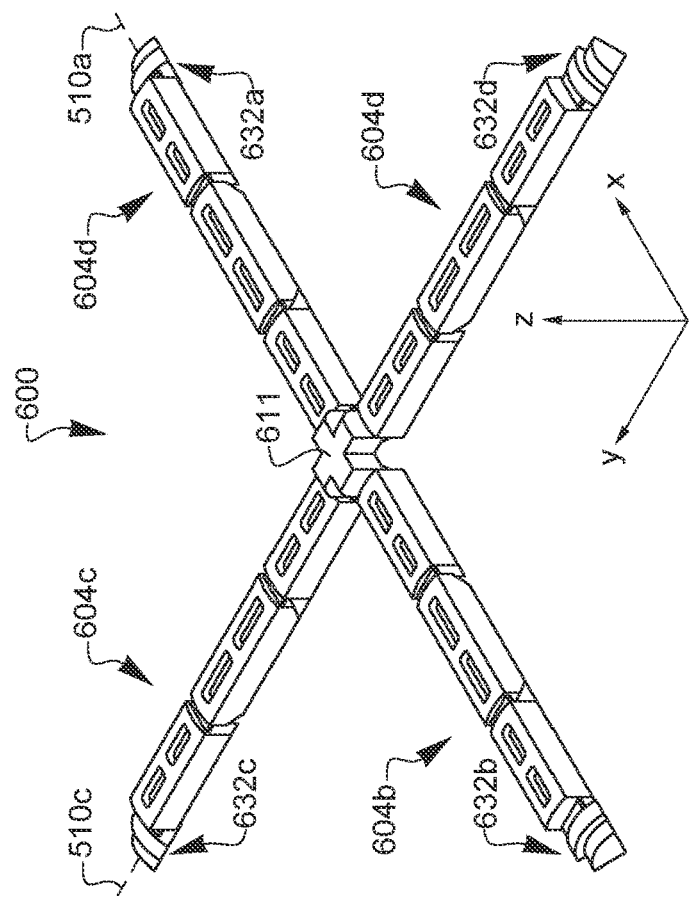
FIGS. 21A and 21B are a bottom perspective view and a top perspective view, respectively, of an embodiment of a tissue engaging assembly prior to assembly within an end effector assembly.
Figure 21A:
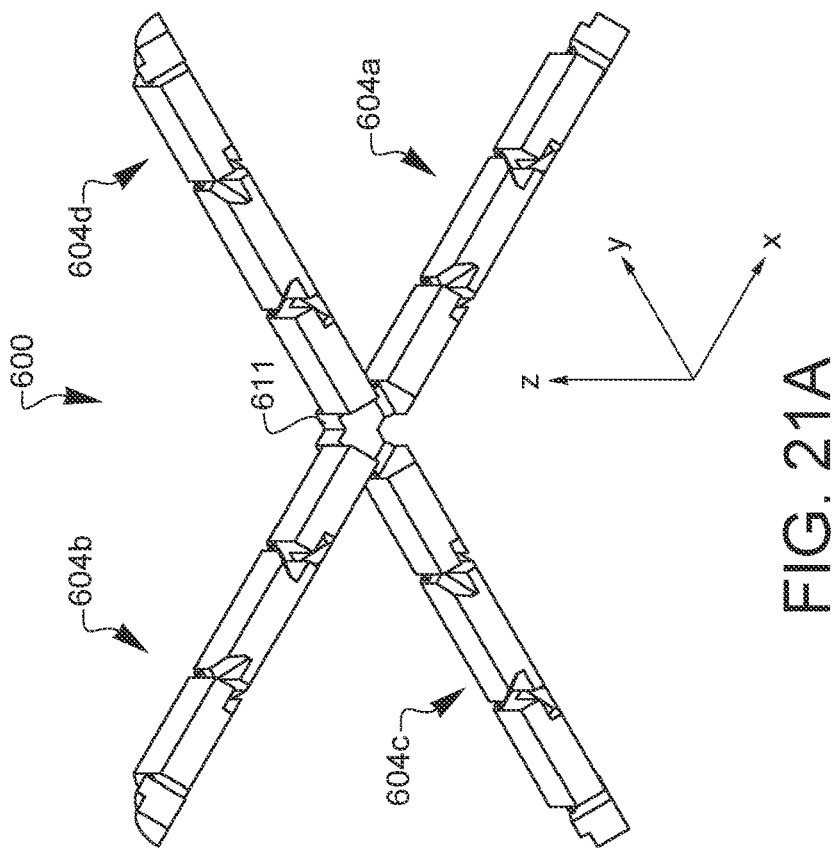
Figure 22A:
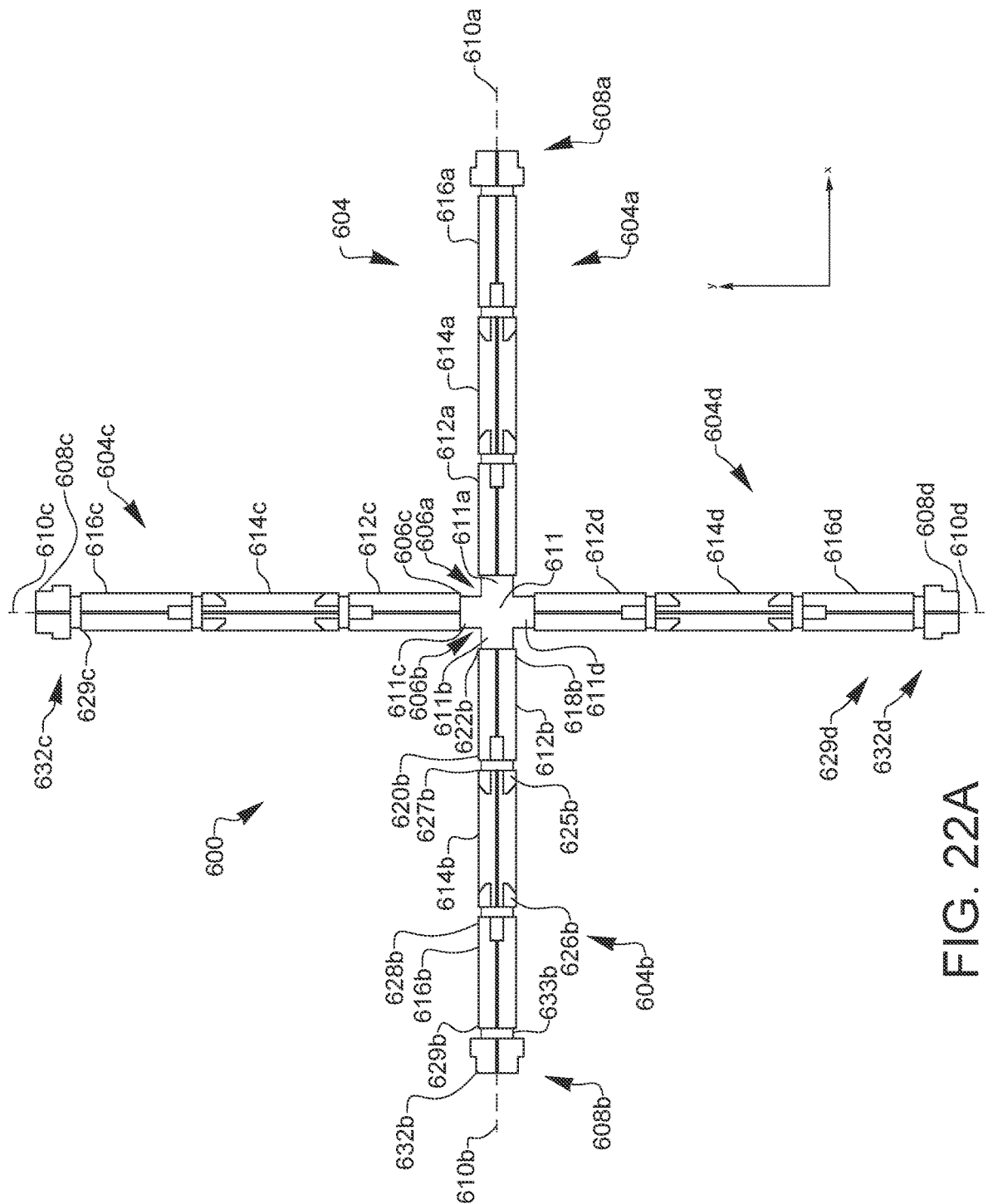

Referring to FIGS. 21A to 22A, the tissue engaging assembly 600 may include the second tissue engaging arm 604b that may be identical to the first tissue engaging arm 604a, and the second tissue engaging arm 604b may be arranged symmetrical to (i.e., a may be a mirror image of) the first tissue engaging arm 604a about a plane that extends through a third arm axis 210c and is parallel to the Y-Z plane of the reference coordinate system of FIGS. 21B and 22A. Accordingly, features of the second tissue engaging arm 604b that correspond to features of the first tissue engaging arm 604a are indicated by reference numbers of the first tissue engaging arm 604a, but are designated using a "b" suffix instead of the "a" suffix used with the first tissue engaging arm 604a.

In particular, and as illustrated in FIG. 22A, the second tissue engaging arm 604b may be elongated and may extend from a first end 606b to a second end 608a along a second arm axis 610b that may be parallel to (or aligned with) the X-axis of the reference coordinate system of FIG. 22A, and the second arm axis 610b may be aligned with the first arm axis 610a. The first end 606a may be coupled to a second portion 211b of the hub portion 611. The second tissue engaging arm 604b may include two or more arm segments, and the second tissue engaging arm 604b may include a first arm segment 612b, a second arm segment 614b, and a third arm segment 616b.

Referring to FIG. 22A, a first end 618b of the first arm segment 612b may be coupled to the second portion 611b of the hub portion 611 with a first hinge 622b, which may be a living hinge. A first end 625b of the second arm segment 614b may be coupled to a second end 620b of the first arm segment 612b with a second hinge 627b, which may be a living hinge. A first end 628b of the third arm segment 616b may be coupled to a second end 626*b* of the second arm segment 614*b* with a third hinge 630*b*, which may be a living hinge. A second end 629*b* of the third arm segment 616*b* may be coupled to a portion of a second end cap segment 632*b* with a fourth hinge 633*b*, which may be a living hinge. The cross-sectional shape of each of the first arm segment 612*b*, the second arm segment 614*b*, and the third arm segment 616*b* of the second tissue engaging arm 604*b* may correspond to the cross-sectional shape of each of the first arm segment 612*a*, the second arm segment 614*a*, and the third arm segment 616*a* of the first tissue engaging arm 604*a*, respectively.

Referring to FIGS. 21A to 22A, the tissue engaging assembly 600 may include the third tissue engaging arm 604*c* and the fourth tissue engaging arm 604*d*, which may be identical to the first tissue engaging arm 604*a* and the second tissue engaging arm 604*b*, respectively. Accordingly, features of the third tissue engaging arm 604*c* that correspond to features of the first tissue engaging arm 604*a* are indicated by reference numbers of the first tissue engaging arm 604*a*, but are designated using a "c" suffix instead of the "a" suffix used with the first tissue engaging arm 604*a*. Further, features of the fourth tissue engaging arm 604*d* that correspond to features of the first tissue engaging arm 604*a* are indicated by reference numbers of the first tissue engaging arm 604*a*, but are designated using a "d" suffix instead of the "a" suffix used with the first tissue engaging arm 604*a*.

The third tissue engaging arm 604*c* and the fourth tissue engaging arm 604*d* may be arranged at an angle relative to the first tissue engaging arm 604*a* and the second tissue engaging arm 604*b*. For example, the third tissue engaging arm 604*c* may be elongated and may extend from a first end 606*c* to a second end 608*c* along a third arm axis 610*c*, and the fourth tissue engaging arm 604*d* may be elongated and may extend from a first end 606*d* to a second end 608*d* along a fourth arm axis 610*d* that may be aligned with the third arm axis 610*c*. The third arm axis 610*c* (and the fourth arm axis 610*d*) may be arranged at an angle (e.g., a right angle) with the first arm axis 610*a* (and the second arm axis 610*b*) such that the third arm axis 610*c* and the fourth arm axis 610*d* are each parallel to (or aligned with) the Y-axis of the reference coordinate system of FIG. 22A, as illustrated in FIG. 22A.

In particular, and as illustrated in FIG. 22A, the third tissue engaging arm 604*c* may be elongated and may extend from a first end 606*c* to a second end 608*c* along the third arm axis 610*c*. The first end 606*c* may be coupled to a third portion 611*c* of the hub portion 611. The third tissue engaging arm 604*c* may include two or more arm segments, and the third tissue engaging arm 604*c* may include a first arm segment 612*c*, a second arm segment 614*c*, and a third arm segment 616*c*. Each of the first arm segment 612*c*, the second arm segment 614*c*, and the third arm segment 616*c* may be identical (or substantially identical) to the first arm segment 612*a*, the second arm segment 614*a*, and the third arm segment 616*a*, respectively, of the first tissue engaging arm 604*a* that was previously described. A second end 629*c* of the third arm segment 616*c* may be coupled to a portion of a third end cap segment 632*c*, as previously described.

Further, as illustrated in FIG. 22A, the fourth tissue engaging arm 604*d* may be elongated and may extend from a first end 606*d* to a second end 608*d* along the fourth arm axis 610*d*. The first end 606*d* may be coupled to a fourth portion 211*d* of the hub portion 611. The fourth tissue engaging arm 604*d* may include two or more arm segments, and the fourth tissue engaging arm 604*d* may include a first arm segment 612*d*, a second arm segment 614*d*, and a third arm segment 616*d*. Each of the first arm segment 612*d*, the second arm segment 614*d*, and the third arm segment 616*d* may be identical (or substantially identical) to the first arm segment 612*b*, the second arm segment 614*b*, and the third arm segment 616*b*, respectively, of the second tissue engaging arm 604*b* that was previously described. A second end 629*d* of the third arm segment 616*d* may be coupled to a portion of a fourth end cap segment 632*d*, as previously described.

As illustrated in FIG. 25, the end effector assembly 602 may include a housing 664, and the tissue engaging assembly 600 may be disposed within (or at least partially within) and/or may be coupled to a portion of the housing 664. The housing 664 may be similar to the housing 150 of the embodiment of the end effector 48 previously described (with reference to FIGS. 6, 8, and 10A, for example), and the housing 664 may extend from a proximal end 667 to a distal end 668 along an end effector axis 665. Similar to the two windows 154*a*, 154*b* disclosed with reference to the housing 150 (illustrated in FIGS. 6 and 7), the housing 664 of the current embodiment of the end effector assembly 602 may have two or more windows 666. In particular, the housing 664 may have four windows (e.g., a first window 666*a*, a second window 666*b*, a third window 666*c*, and a fourth window 666*d*, and each window 666 may be associated (and operatively aligned) with a corresponding one of the first tissue engaging arm 604*a*, the second tissue engaging arm 604*b*, the third tissue engaging arm 604*b*, and the fourth tissue engaging arm 604*d*, respectively. Each of the first window 666*a*, the second window 666*b*, the third window 666*c*, and the fourth window 666*d* may be arrayed in any configuration on the housing 664. For example, each of the first window 666*a*, the second window 666*b*, the third window 666*c*, and the fourth window 666*d* may be disposed at even intervals about the effector axis 665, such as 90 degree intervals, as illustrated in FIG. 26B. Any or all of the first window 666*a*, the second window 666*b*, the third window 666*c*, and the fourth window 666*d* may be elongated and may extend from a proximal end to a distal end along an axis that is parallel to or substantially parallel to the end effector axis 665. One or more interior surfaces of the housing 664 may define or partially define a housing interior 676 (illustrated in FIG. 26A), and each of the two or more windows 666 may extend from an exterior surface defining the housing 664 towards the end effector axis 665 such that each of the two or more windows 666 opens to the housing interior 676.

In some embodiments, the hub portion 611 of the tissue engaging assembly 600 may be disposed in (or within) the housing interior 676 of the housing 664 at or adjacent to the distal end 668, and the hub portion 611 may be coupled (or fixedly coupled) to the portion of the housing 664 such that the hub portion 611 remains stationary relative to the housing 664 when the end effector assembly 602 is displaced from the first undeployed position 603 (illustrated in FIG. 25) to the second deployed position 605 (illustrated in FIGS. 26A to 26C) and vice versa. In some embodiments, the hub portion 611 may be coupled to a portion of an end cap 670 coupled to the distal end 668 of the housing 664, as best illustrated in FIG. 27 showing the end effector assembly 602 with the housing 664 omitted for clarity.

As illustrated in FIG. 26A, the end effector assembly 602 may also include a plunger 669 that may be similar or identical to the plunger 30 of the end effector 48 previously described, and the plunger 669 may be directly or indirectly coupled to one of more of the torque links 58 (see FIG. 7) and/or to the torque member 202 (see FIG. 11) that were previously described. The plunger 669 may be disposed at least partially in the housing 664 (i.e., within the housing interior 676) at or adjacent to the distal end 668, and the plunger 669 may be longitudinally displaceable relative to the housing 664 (i.e., displaceable along the end effector axis 665) in the same manner as the plunger 30 previously described. All or a portion of each of the first end cap segment 632a of the first tissue engaging arm 604a, the second end cap segment 632b of the second tissue engaging arm 604b, the third end cap segment 632c of the third tissue engaging arm 604c, and the fourth end cap segment 632d of the fourth tissue engaging arm 604b may be secured to (or within, or partially within) a portion of the plunger 669 to couple the plunger 669 to the tissue engaging assembly 600. In some embodiments, each of the first end cap segment 632a of the first tissue engaging arm 604a, the second end cap segment 632b of the second tissue engaging arm 604b, the third end cap segment 632c of the third tissue engaging arm 604c, and the fourth end cap segment 632d of the fourth tissue engaging arm 604b may form a pie-shaped wedge (illustrated in FIG. 21B) that cooperate to form a disk-shape when assembled, and this disk-shape may be received into a complementary recess formed in the plunger 669. As such when the plunger 669 is at a first position, such as a first proximal position (illustrated for plunger 30 in FIG. 6), the end effector assembly 602 is in the first undeployed position 603 illustrated in FIG. 25. In such a position, each of the first arm axis 610a, the second arm axis 610b, third arm axis 610c, and fourth arm axis 610a are parallel or substantially parallel to the end effector axis 665, and all or a portion of each of the first arm segment 612a, the second arm segment 614a, and the third arm segment 616a may be disposed within the interior portion 676 of the housing 664 (or within an aperture in the housing 664 forming the first window 666a).

Figure 26C:
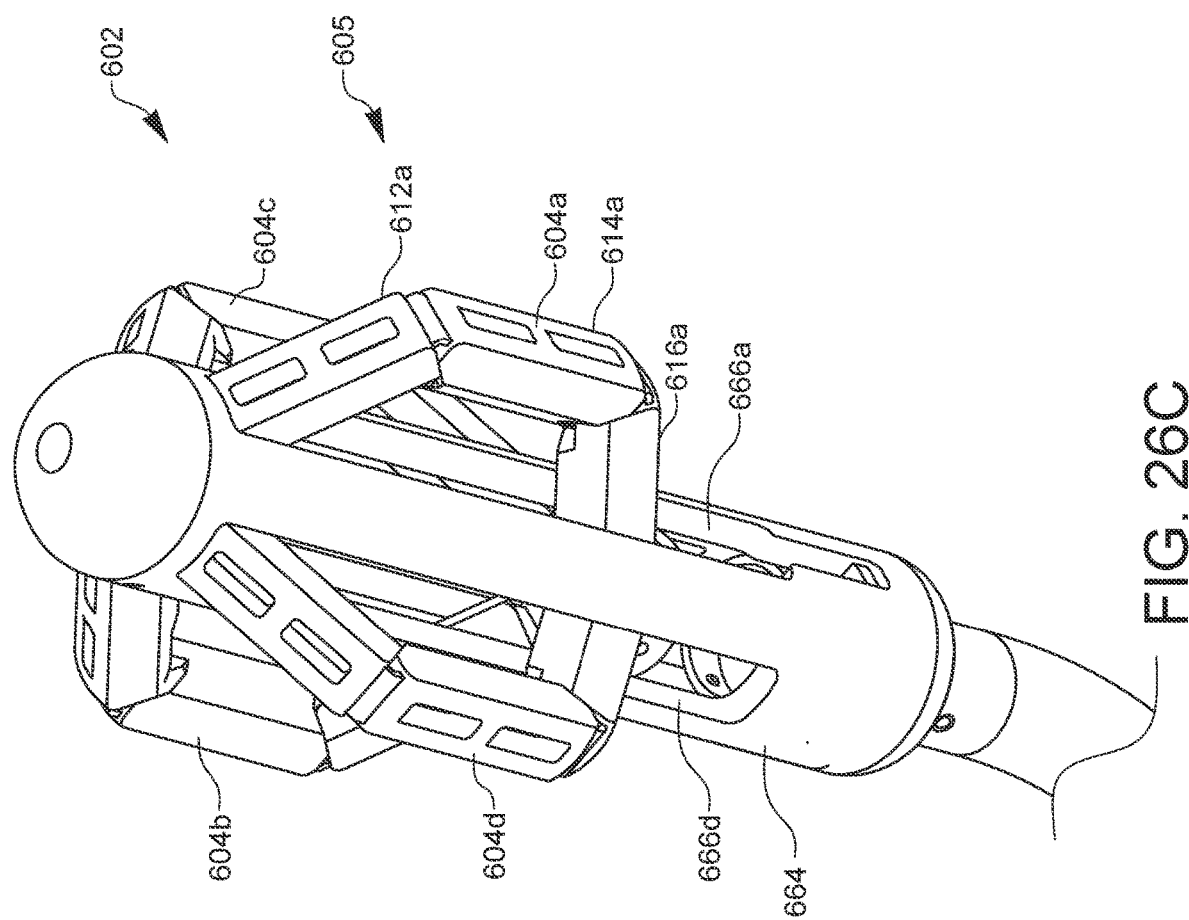
Figure 27:
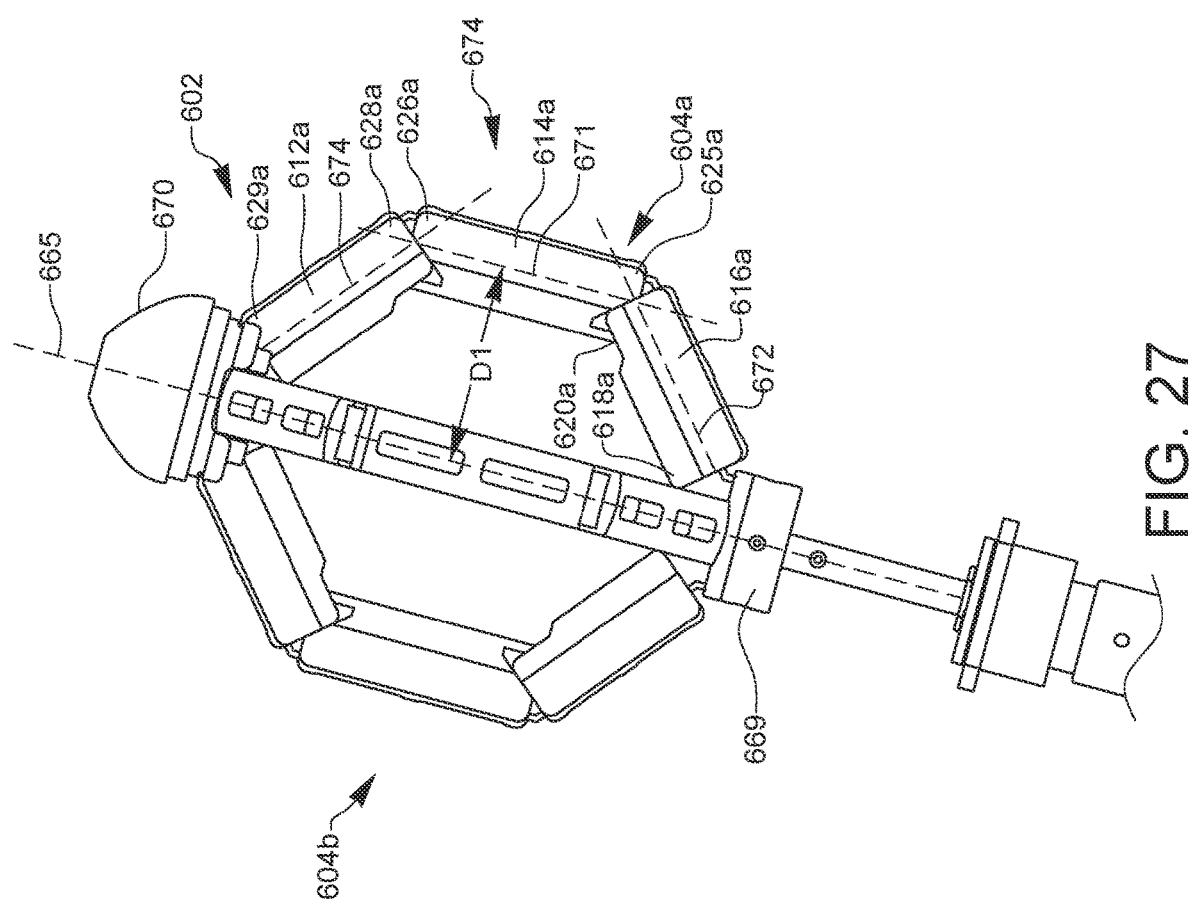
FIG. 27 is a perspective view of the embodiment of the end effector assembly of FIG. 25 in the second deployed position with a housing of the end effector assembly removed for clarity.

When the plunger 669 displaces distally (in the manner previously described in relation to plunger 30) along the end effector axis 665 from this first proximal position to a second position, such as a second distal position (illustrated in FIG. 27 showing the end effector assembly 602 with the housing 664 omitted for clarity), the end effector assembly 602 transitions or displaces to the second deployed position 605 (illustrated in FIGS. 26A to 26C). In particular, with reference to FIGS. 21B and 27, the hub portion 611 of the tissue engaging assembly 600 is secured (and/or stationary) at the portion of the housing 664 that is at or adjacent to the distal end 668, and with the end cap segments 632a-632d of the tissue engaging arms 604a-604d configured to displace distally with the plunger 669, the tissue engaging arms 604a-604d change in shape from the straight configuration of FIG. 25 to the deployed configuration of FIGS. 26A to 26C. In this deployed configuration, with respect to the first tissue engaging arm 604a, the first mating feature 632a of the first arm segment 612a may engage a corresponding first mating feature 634a of the second arm segment 614a to maintain the first arm segment 612a and the second arm segment 614a in the desired position when the end effector assembly 602 is in the second deployed position 605, as previously described. In addition, in the second deployed position 605, the second mating feature 648a of the second arm segment 614a (or one or more portions of the second mating feature 648a of the second arm segment 614a) may engage a corresponding first mating feature 650a of the third arm segment 616a (or a corresponding one or more portions of the first mating feature 650a of the third arm segment 616a) to maintain the third arm segment 616a and the second arm segment 614a in a desired position when the end effector assembly 602 is in the second deployed position 605, also as previously described.

So configured, a second segment axis 671 that extends through the second arm segment 614a from the first end 625a to the second end 626a along the first arm axis 610a is parallel to the end effector axis 665 and offset from the end effector axis 665 by a first distance D1, as illustrated in FIG. 27. Further, a first segment axis 672 that extends through the first arm segment 612a from the first end 618a to the second end 620a is oblique relative to the end effector axis 665, as illustrated in FIG. 27. In some embodiments, the first segment axis 672 may form an angle between 20° and 70° (such as between 35° and 55°) with the end effector axis 665. In addition, a third segment axis 674 that extends through the third arm segment 616a from the first end 628a to the second end 629a is oblique relative to the end effector axis 665, as illustrated in FIG. 27. In some embodiments, the third segment axis 674 may form an angle between 20° and 70° (such as between 35° and 55°) with the end effector axis 665, and this angle may be equal (but oppositely disposed) to the angle formed by the first segment axis 672 and the end effector axis 665, the third segment axis 674 may be a mirror image of the first segment axis 672 about an axis of symmetry that is normal to the end effector axis 665. The first distance D1 separating the second segment axis 671 from the end effector axis 665 when the end effector assembly 602 is the second deployed position 605 is greater than a second distance D2 (illustrated in FIG. 25, in which the view of the first tissue engaging arm 604a is blocked by the housing 664) that separates the second segment axis 671 from the end effector axis 665 when the end effector assembly 602 is the first undeployed position 603. In this the first undeployed position 603 illustrated in FIG. 25, the second segment axis 671 may be parallel to the end effector axis 665. Further, in this first undeployed position 603, the first segment axis 672, the second segment axis 671, and the third segment axis 674 may all be coaxially aligned and may each be parallel to or substantially parallel to the end effector axis 665.

Turning to FIG. 26C, in the second deployed position 605, the second arm segment 614a may be completely external to the housing 664, while a portion of the first arm segment 612a may extend through the first window 666a such that the first end 618a (see FIG. 24A) of the first arm segment 612a is disposed within the housing interior 676 of the housing 664 (or within the aperture in the housing 664 forming the first window 666a) and the second end 620a of the first arm segment 612a is disposed external to the housing 664. Alternatively, in some embodiments, all or a portion of the first hinge 622a (see FIG. 24A) may be disposed within the housing interior 676 of the housing 664, while the first end 618a of the first arm segment 612a may be disposed exterior to the housing 664 but adjacent (e.g., immediately adjacent to) the aperture in the housing 664 forming the first window 666a. Similarly, in the second deployed position 605, a portion of the third arm segment 616a may extend through the first window 666a such that the second end 629a (see FIG. 24A) of the third arm segment 616a is disposed within the housing interior 676 of the housing 664 (or within an aperture in the housing 664 forming the first window 666a) and the first end 628a (see FIG. 24A) of the third arm segment 616a is disposed external to the housing 664. Alternatively, in some embodiments, all or a portion of the fourth hinge 633a (see FIG. 24A) may be disposed within the housing interior 676 of the housing 664, while the second end 629a of the third arm segment 616a may be disposed exterior to the housing 664 but adjacent (e.g., immediately adjacent to) the aperture in the housing 664 forming the first window 666a.

Any or all of the second tissue engaging arm 604b, the third tissue engaging arm 604b, and the fourth tissue engaging arm 604d may each displace or transition identically to the first tissue engaging arm 604a when the end effector assembly 602 is displaced from the first undeployed position 603 to the second deployed position 605 and vice versa, as illustrated in FIGS. 25 to 27. Accordingly, the first tissue engaging arm 604a, the second tissue engaging arm 604b, the third tissue engaging arm 604b, and the fourth tissue engaging arm 604d may be disposed physically offset from each other but otherwise in an identical manner in each of the first undeployed position 603 and the second deployed position 605 and any point in between.

The embodiment of the end effector assembly 602 may be coupled to the handle portion 12 of the tissue manipulation device 10 previously described. However, with reference to FIGS. 28A to 28G, the embodiment of the end effector assembly 602 may be coupled to an embodiment of a tissue manipulation device 700 that may have a body portion 702 that may include a grip portion 703 that is configured to be grasped by a single hand of a user during the procedure. In such an embodiment, as illustrated in the cross-sectional view of FIG. 29B, a portion of the shaft portion 40 at or adjacent to (or distal to) the proximal end 42 of the shaft portion 40 may be coupled to a first portion 704 of the body portion 702. In addition, an adjustment wheel 710 may be rotatably coupled to a second portion 705 of the body portion 702. The adjustment wheel 710 may rotate relative to the second portion 705 of the body portion 702 about a wheel axis 709 that may be parallel to the X-axis of the reference coordinate system of FIG. 29B. The adjustment wheel 710 may be similar in form and function to the adjustment wheel 122 previously described, and the adjustment wheel 710 may be coupled to the end effector assembly 602 to rotate the end effector assembly 602 about the end effector axis 665 (see FIG. 28A) relative to the distal end 44 of the shaft portion 40.

To turn the adjustment wheel 710, the adjustment wheel 710 may be displaced distally (against the proximally-directed bias force provided by spring 712) by the user (not shown) from a locked position (illustrated in FIGS. 30A and 30B) to an unlocked position (illustrated in FIGS. 31A and 31B) to unlock the adjustment wheel 710 and allow the adjustment wheel 710 to rotate about the wheel axis 709. Advantageously, the adjustment wheel 710 may be displaced distally when the user is gripping the grip portion 703 and uses a finger (e.g., a thumb) of the hand gripping the grip portion 703 to unlock and rotate the adjustment wheel 710. When the adjustment wheel 710 has been rotated to a desired position, the user may release the adjustment wheel 710 which may then be displaced proximally by the spring 712 to the locked position in which the adjustment wheel 710 is unable to rotate.

Figures 30A, 30B:
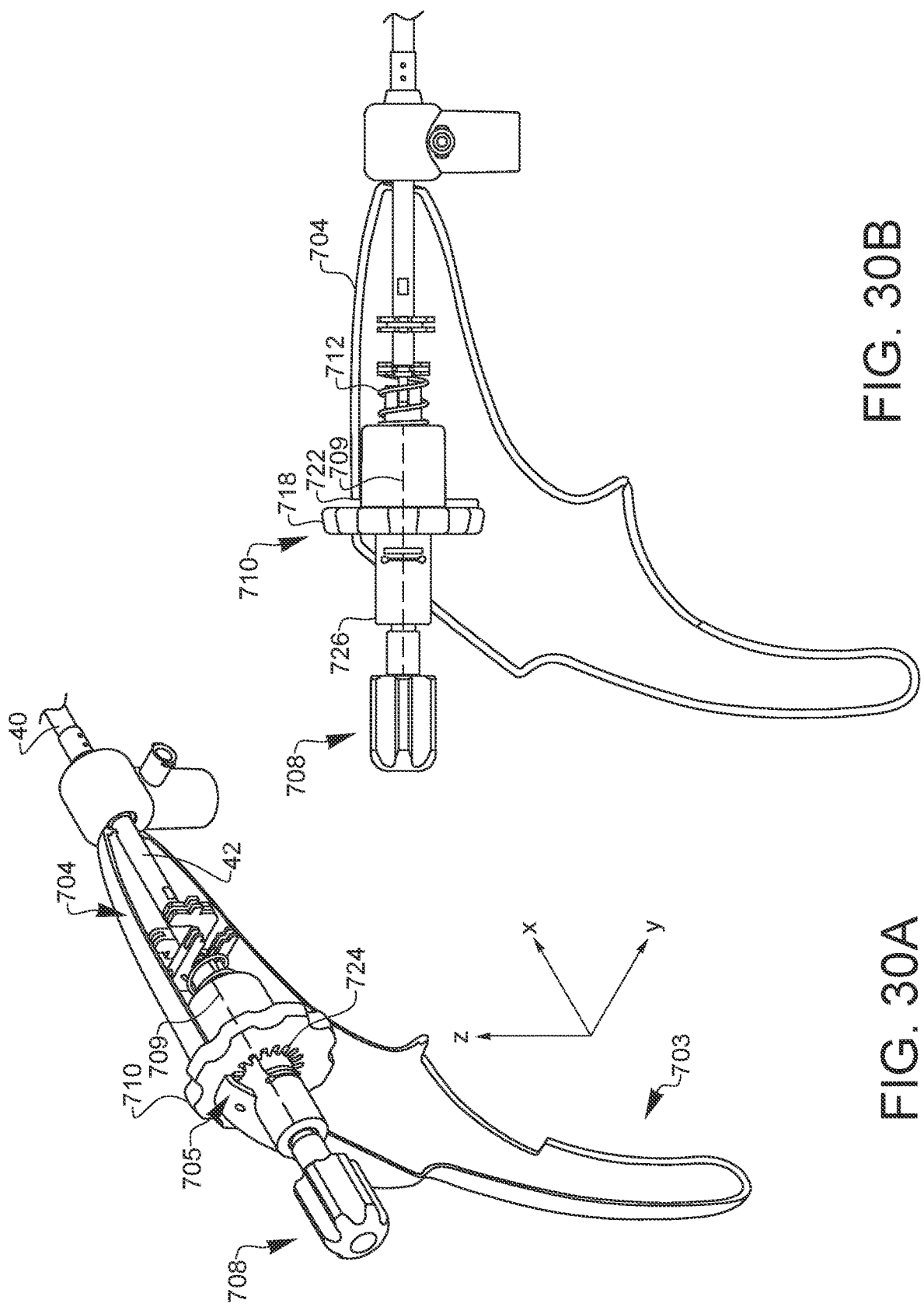
FIGS. 30A and 30B are a perspective view and a side view, respectively, of the tissue engaging assembly with a portion of the body portion removed for clarity and with an adjustment wheel in a locked position.
Figures 31A, 31B:
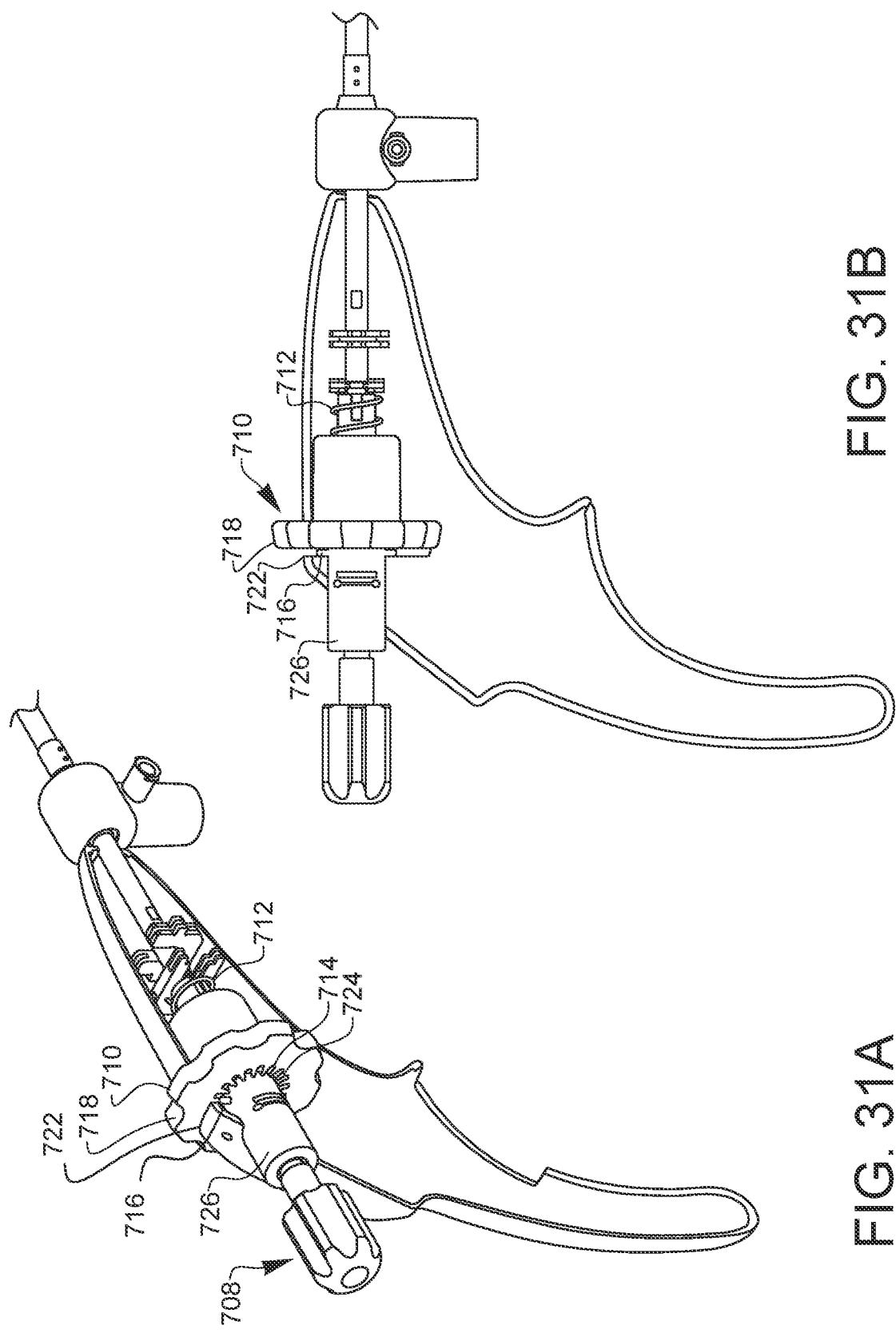
FIGS. 31A and 31B are a perspective view and a side view, respectively, of the tissue engaging assembly of FIGS. 30A and 30B with the adjustment wheel in an unlocked position.

With reference to FIG. 31A, the adjustment wheel 710 may include an engagement portion 718 that may be circular or substantially circular in cross-sectional shape, and the engagement portion 718 may have the shape of a disk. A portion of the engagement portion 718 may extend out of a housing slot 722 formed in the housing portion 704. A central aperture 724 be formed through the engagement portion 718, and a plurality of locking slots 714 may extend radially along an inner edge forming the central aperture 724. A post 716 that is adapted to be received into any one of the plurality of locking slots 714 may be secured to a cylindrical hub 726. The cylindrical hub 726 may be fixed relative to the housing portion 704 such that when the post 716 is received into any one of the plurality of locking slots 714, the adjustment wheel 710 is in the locked position and thus prevented from rotating relative to the cylindrical hub 726, as illustrated in FIGS. 30A and 30B. However, when the adjustment wheel 710 is displaced distally (against the proximally-directed bias force provided by spring 712) by the user from the locked position to the unlocked position (illustrated in FIGS. 31A and 31B), the engagement portion 718 displaces distally relative to the post 716 (and the cylindrical hub 726) until the post 716 is no longer disposed in any one of the plurality of locking slots 714. So positioned, the adjustment wheel 710 may be rotated freely about the wheel axis 709 by a user until the user ceases to force the adjustment wheel 710 in a distal direction, at which time the spring 712 displaces the adjustment wheel 710 proximally such that one of the plurality of locking slots 714 that is aligned with the post 716 receives the post 716 to lock the adjustment wheel 710 into the locked position of FIGS. 30A and 30B.

Figure 29A:
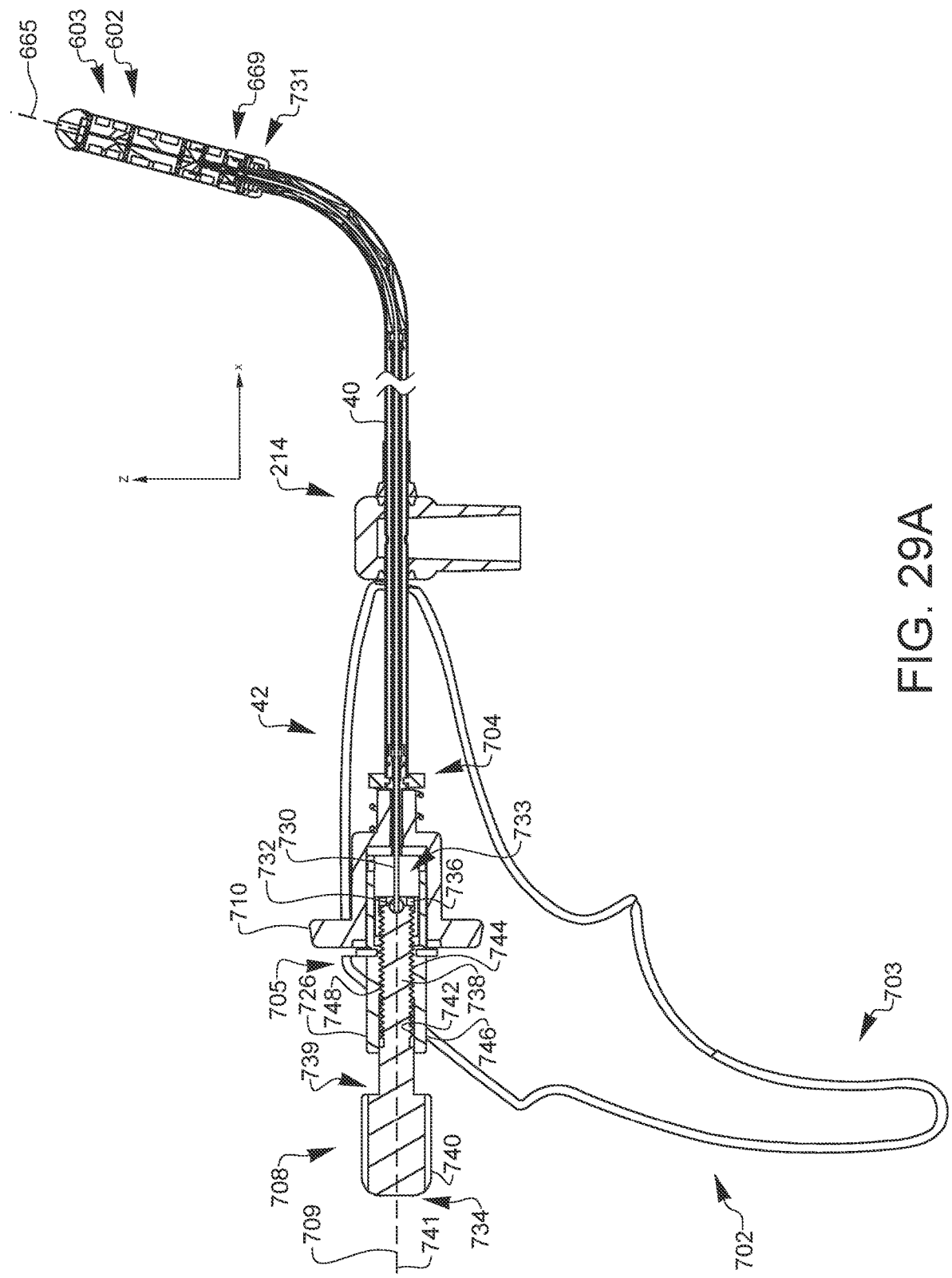
FIG. 29A is a cross-sectional view of the embodiment of the tissue engaging assembly taken along section line 29A-29A in FIG. 28B.

With reference to FIG. 29A, the tissue manipulation device 700 may also have an adjustment member 708 that may be similar in form and identical in function to the adjustment member 22, and the adjustment member 708 may be coupled to the end effector assembly 602 to transition the end effector assembly 602 between the first undeployed position 603 (illustrated in FIG. 25) and the second deployed position 605 (illustrated in FIGS. 26A to 26C). In particular, the adjustment member 708 may be elongated and extend along a longitudinal axis 741 from a proximal end 734 to a distal end 736, and the longitudinal axis 741 may be coaxially aligned with the wheel axis 709. An insertion portion 738 may extend from the distal end 736 to an intermediary point 739, and an input portion 740 may extend proximally from the insertion portion 738 from the intermediary point 739 to the proximal end 734 of the adjustment member 708. The insertion portion 738 may be at least partially received in a central bore 742 of the cylindrical hub 726, and a threaded portion 744 of an outer surface 746 of the insertion portion 738 may threadedly engage a threaded portion 748 of the central bore 742 of cylindrical hub 726.

Figure 29B:
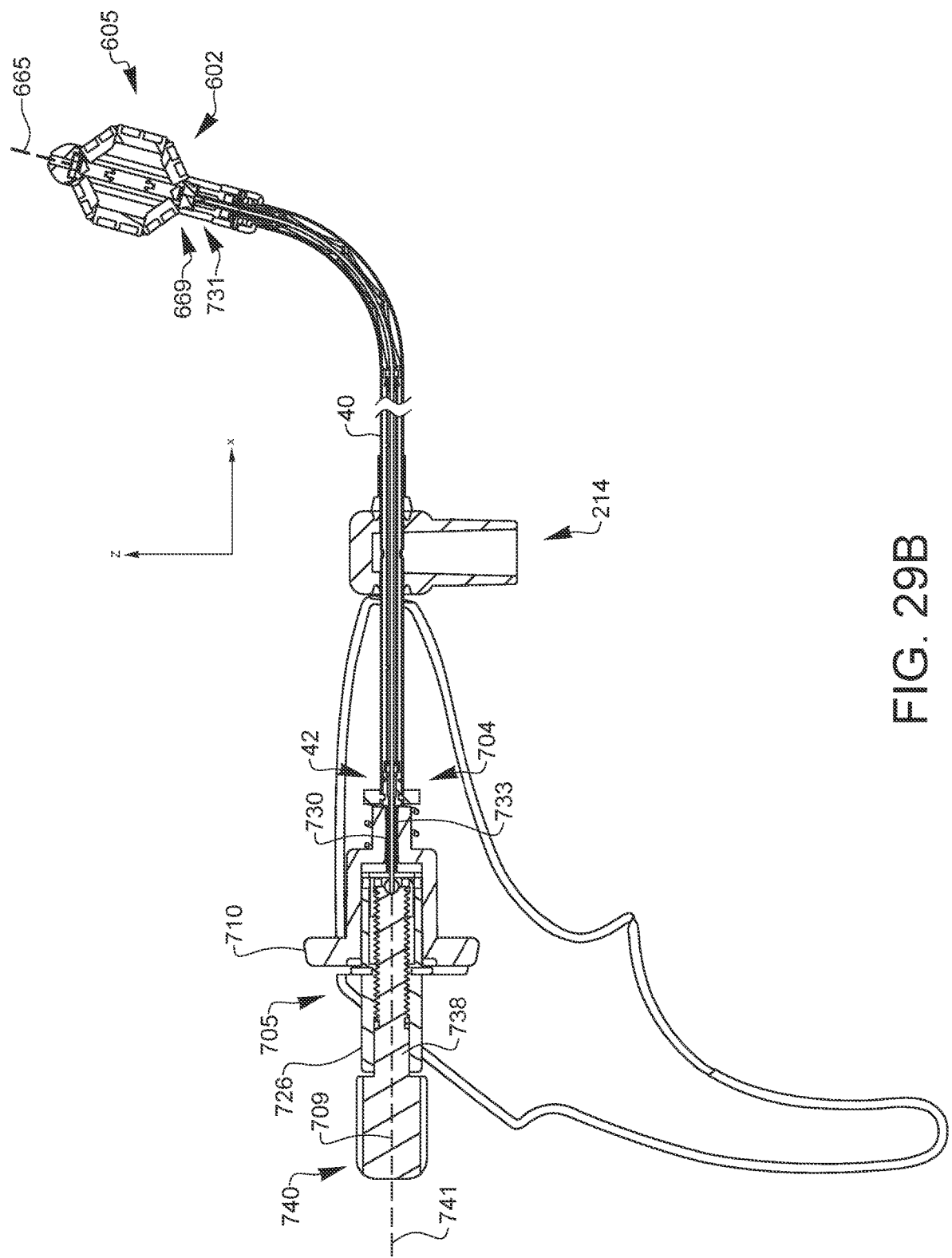
FIG. 29B is a cross-sectional view of the embodiment of the tissue engaging assembly taken along section line 29B-29B in FIG. 28B with the end effector assembly in the second deployed position.

The adjustment member 708 may be coupled to the end effector assembly 602 by an elongated coupling portion 733 such that displacing the adjustment member 708 displaces the coupling portion 733 and transitions the end effector assembly 602 between the first undeployed position 603 (illustrated in FIG. 29A) and the second deployed position 605 (illustrated in FIG. 29B). The coupling portion 733 may include a wire 732 that may be similar or identical to the wire 52 previously discussed. That is, a proximal end 730 of the wire 732 may be secured to a portion of the adjustment member 708, such as a portion at or adjacent to the distal end 736 of the adjustment member 708, and a distal end 731 of the wire 732 may be secured to the end effector assembly 602 in any suitable manner, and may be secured to the plunger 669 in the same manner as the distal end 56 of the wire 52 is coupled to the end effector 48 (as illustrated in FIG. 3). Accordingly, when a user rotates the input portion 740 (relative to the cylindrical hub 726 and the body portion 702) about the longitudinal axis 741 in a first rotational direction, the adjustment member 708 displaces distally along the longitudinal axis 741 from a first adjustment member position (illustrated in FIG. 29A) to a second adjustment member position (illustrated in FIG. 29B), thereby distally displacing the distal end 731 of the wire 732 to transition the end effector assembly 602 from the first undeployed position 603 (illustrated in FIG. 29A) to the second deployed position 605 (illustrated in FIG. 29B). Correspondingly, when the user rotates the input portion 740 (relative to the relative to the cylindrical hub 726 and the body portion 702) about the longitudinal axis 741 in a second rotational direction, the adjustment member 708 displaces proximally along the longitudinal axis 741 from the second adjustment member position (illustrated in FIG. 29B) to the first adjustment member position (illustrated in FIG. 29A), thereby proximally displacing the distal end 731 of the wire 732 to transition the end effector assembly 602 from the second deployed position 605 (illustrated in FIGS. 29B) to the first undeployed position 603 (illustrated in FIG. 29A). Further, the when the user rotates the input portion 740 about the longitudinal axis 741 such that the adjustment member 708 displaces between the second adjustment member position and the first adjustment member position, the end effector assembly 602 may be transitioned to a semi-deployed position between the first undeployed position 603 and the second deployed position 605.

Figure 28A:
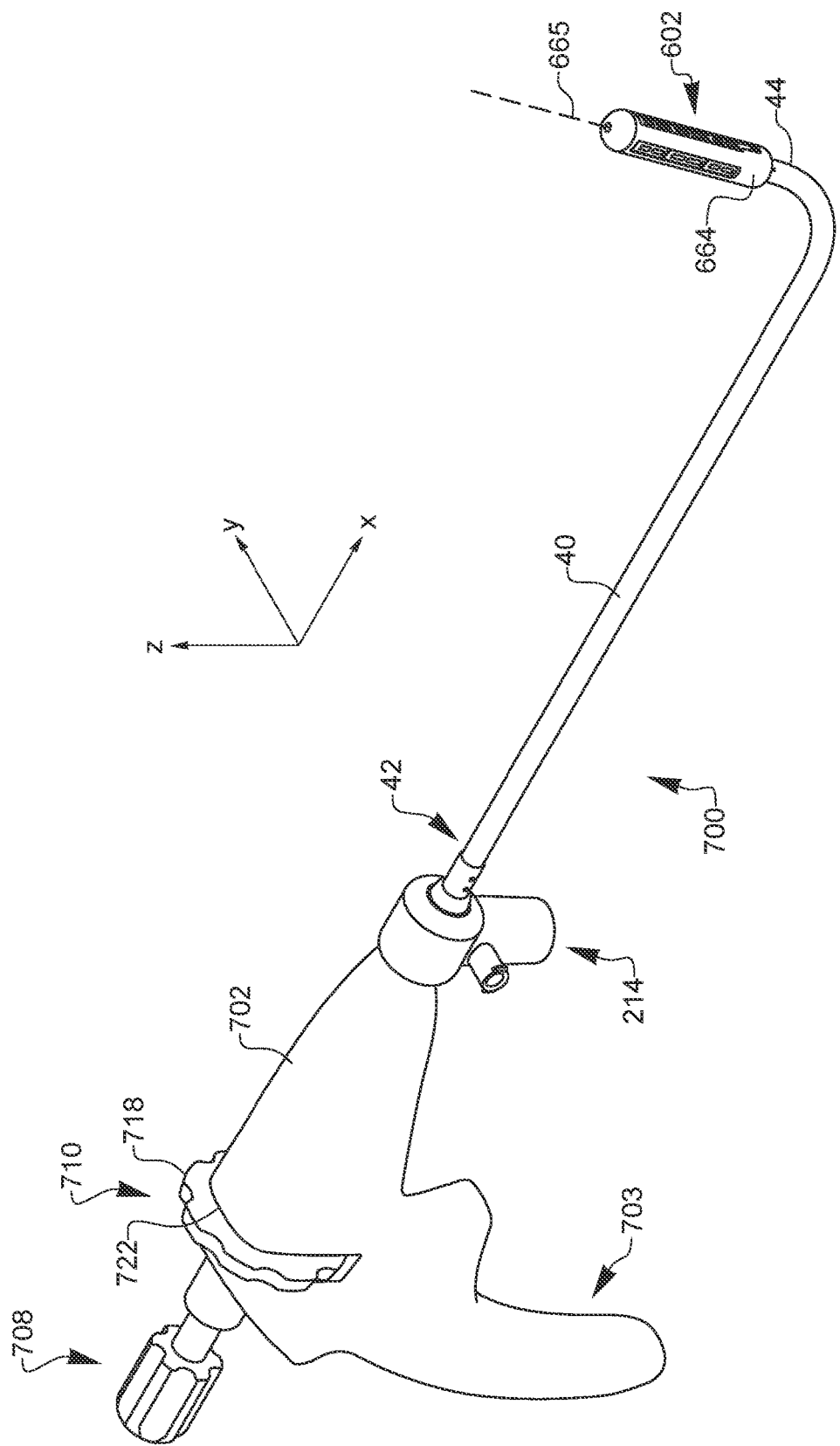
Figure 28D:
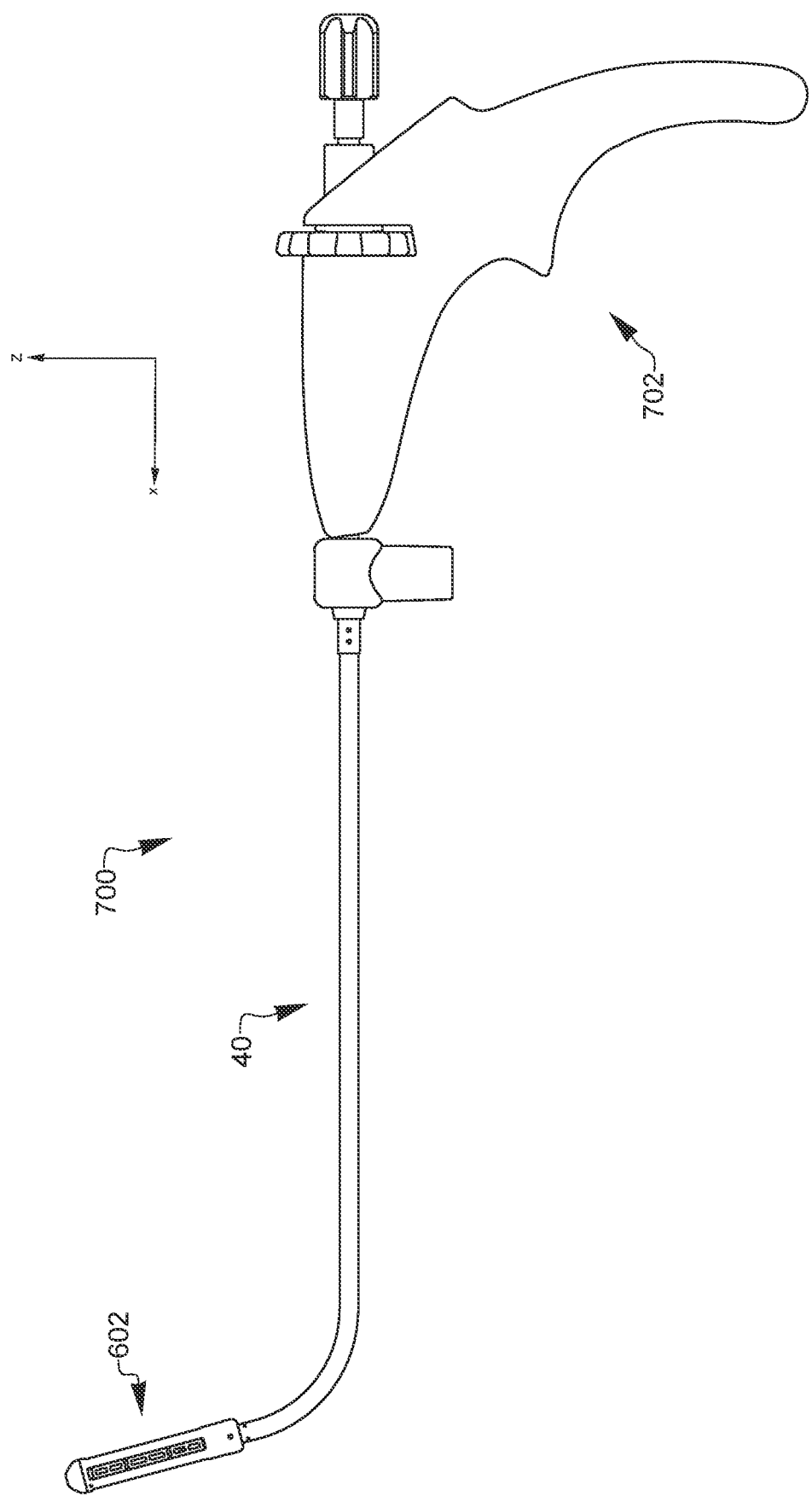
Figure 28E:
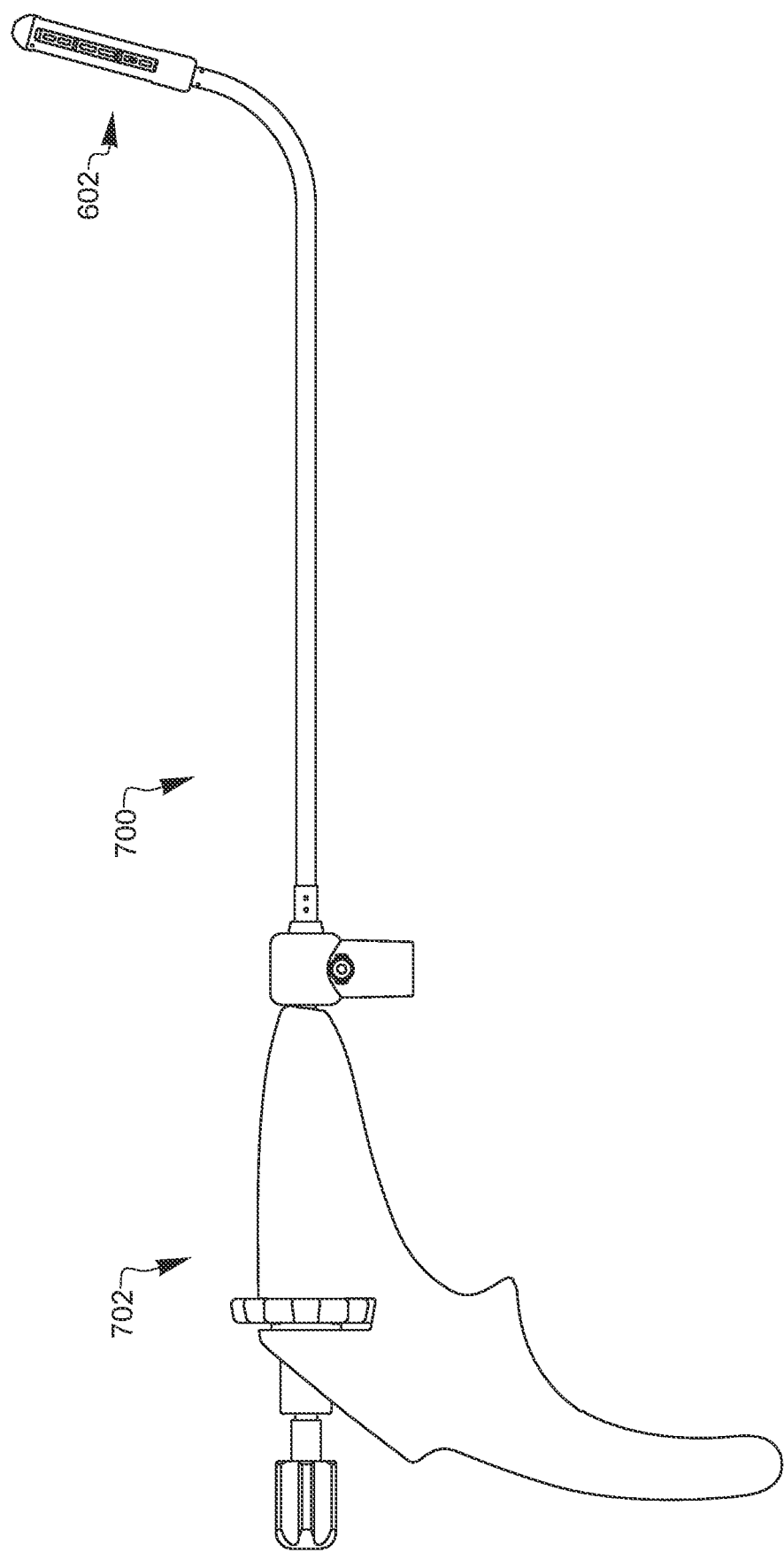
Figure 28G:
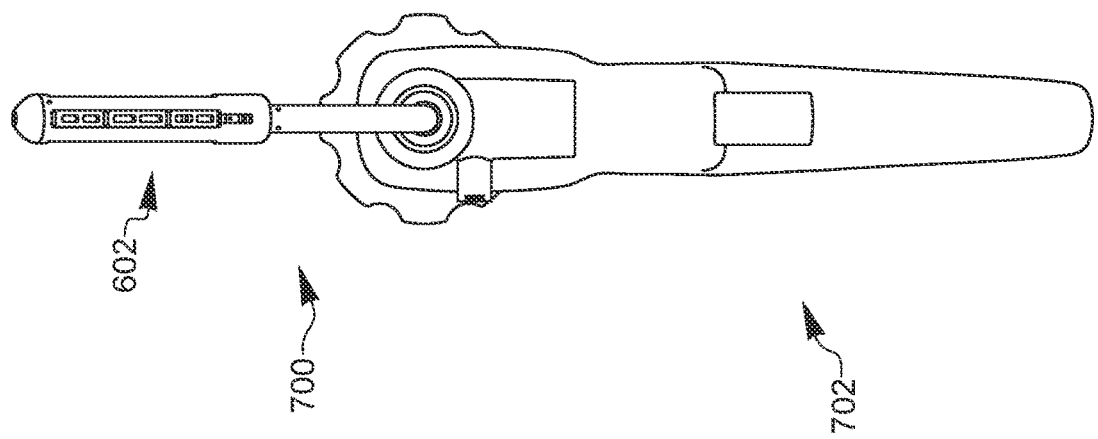
Figure 28F:
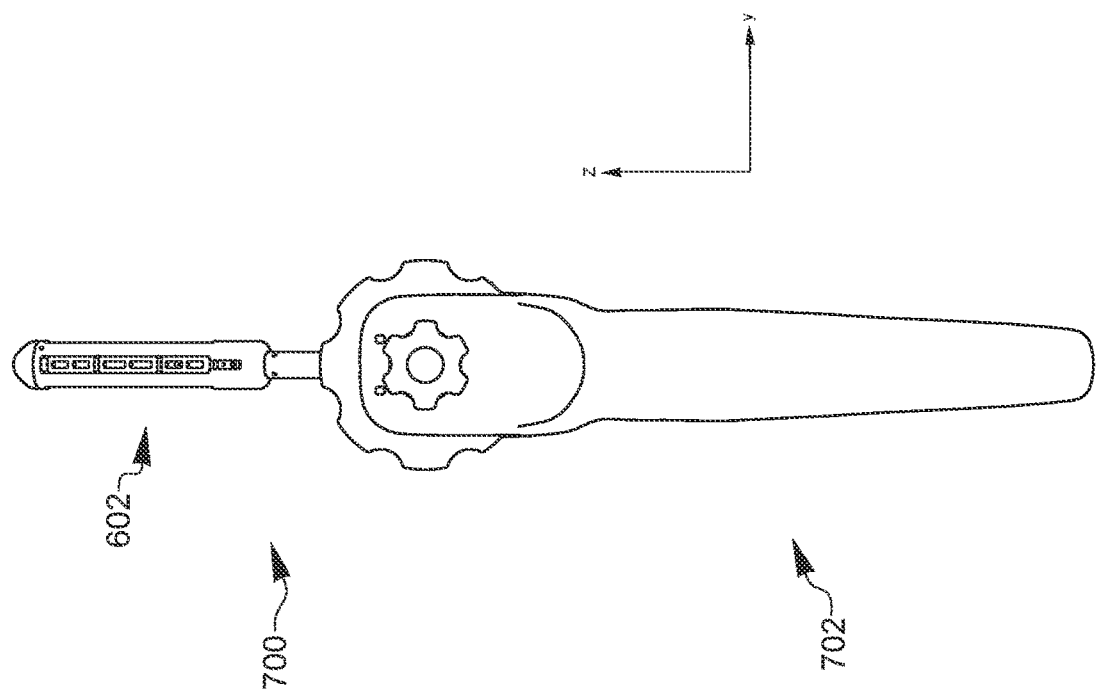

Referring again to FIG. 1, the tissue manipulation device 10, 700 may include a port 214 configured to deliver fluids to a treatment area. For example, the port 214 may extend from a portion of the housing portion 12, such as a portion of the distal support portion 112 of the wheel housing portion 108. In other embodiments, the port 214 may be coupled to a portion of the shaft portion 40, as illustrated in FIGS. 28A and 29A. As illustrated in FIG. 3, the port 214 may be cylindrical and may extend from an inner end 216 to an outer end 218 along an axis that may be transverse to the longitudinal axis 14. The inner end 216 may be in communication with a chamber 219 within the distal support portion 112 and adjacent to the proximal end 42 of the shaft portion 40. One or more seals may be disposed on the wheel hub 170 to prevent fluid in the chamber 219 from moving proximally. The shaft portion 40 may include a plurality of apertures 220 that may be at least partially disposed on the curved portion 142 of the shaft portion 40. Each of the plurality of apertures 220 extends from the exterior surface 145 of the shaft portion 40 to the shaft interior portion 146. One or more seals may be disposed distal to the plurality of apertures 220 to prevent fluid from moving distal to the one or more seals. As such, when a fluid is introduced into the outer end 218 of the port 214, the fluid travels through the port 214 and into the chamber 219, where the fluid enters the shaft interior portion 146 and travels distally towards the plurality of apertures 220, where the fluid exits each of the plurality of apertures 220. One having ordinary skill in the art would recognize that the fluid would flow in any gaps or passages associated with components disposed within the shaft interior portion 146. For example, one having ordinary skill in the art would recognize that the fluid would flow through the link bores 286 of the torque links 58 or through gaps between the torque links 58 and portions of the one or more interior surfaces 147 defining the shaft interior portion 146. The outer end 218 of the port 214 may be configured to connect to a source of fluid, and may have a luer fitting, for example. The fluid may be a liquid or gas that may be delivered to a treatment area of a patient that is at or adjacent to at least one of the plurality of apertures 220. In operation, fluid may also be removed from the treatment area by entering any of the plurality of apertures 220 and exiting the outer end 218 of the port 214.

The tissue manipulation device 10 may be fabricated using any suitable material or combination of materials, such as materials that allow for the cleaning and sterilization of all or parts of the tissue manipulation device 10 (e.g., a plastic material or stainless steel). For example, all or portions of the handle portion 12, the shaft portion 12, and the end effector 48 may all be composed or made from stainless steel or plastic.

In operation, the tissue manipulation device 10, 700 may be used in a prostatectomy procedure. In particular, the tissue manipulation device 10, 700 may be inserted transurethral by an operator, e.g., surgeon, into the penis of a patient, and the curved portion 142 of the shaft portion 40 allows the shaft portion 40 to travel along the patient's urethra and past the bony diaphragm structure of the pelvis until the distal end 152, 668 of the housing 150, 664 of the end effector 48, 602 is located in the patient's prostate. Once in the prostate, the adjustment member 22, 708 may be rotated by the surgeon to drive the tissue engaging members 20 (or the tissue engaging arms 604) to extend into the prostate. Barbs 38 and 46 on the tissue engaging members facilitate gripping of the prostate. Although the tissue engaging members 20 (or the tissue engaging arms 604) are shown fully extended, in FIG. 8, they may be extended to any desired degree by the surgeon between the undeployed position and full extension. The prostate's position can then be manipulated as needed to facilitate prostatectomy. The positioning of the prostate is provided under control of the surgeon, such as, raised or lowered by adjusting the tilt angle of the shaft portion 40 with respect to the patient's body, pulled or pushed by changing the extent of the shaft portion 40 passing through the urethra (i.e., slightly pushing or pulling the handle potion 12 or grip portion 703), and, advantageously, bi-directionally rotated using the adjustment wheel 122, 710. In this manner, the surgeon can position the prostate to expose and apply tension to the tissue at the anterior side of the prostate, and thereby locate the area or zone of dissection and proceed to mobilize (or cut the surrounding tissue of) the prostate at its anterior side. The prostate's position may then be further manipulated with the tissue manipulation device 10, 700 to facilitate exposing and placing under tension the area or zone of dissection and proceed to mobilize the tissue (or cut the surrounding tissue) along the posterior side and both lateral sides of the prostate. Once the prostate has been dissected, turning the adjustment member 22, 708 may retract the tissue engaging members 20 (or the tissue engaging arms 604). The prostate can then be removed from the patient and the urethra sutured to the bladder.

The tissue manipulation device 10, 700 thus provides a surgical instrument, which is useful in either open surgery or a laparoscopic prostatectomy, but may also be used in other surgical procedures to manipulate tissue structures other than the prostate via a natural or surgical opening or channel in the body of a patient. The control of the prostate's position enabled by the multiple degrees of rotational freedom of the tissue manipulation device 10 allows for precise dissection thereby minimizing the risk of damage to the neurovascular bundles and other tissue about the prostate.

Figure 14B:
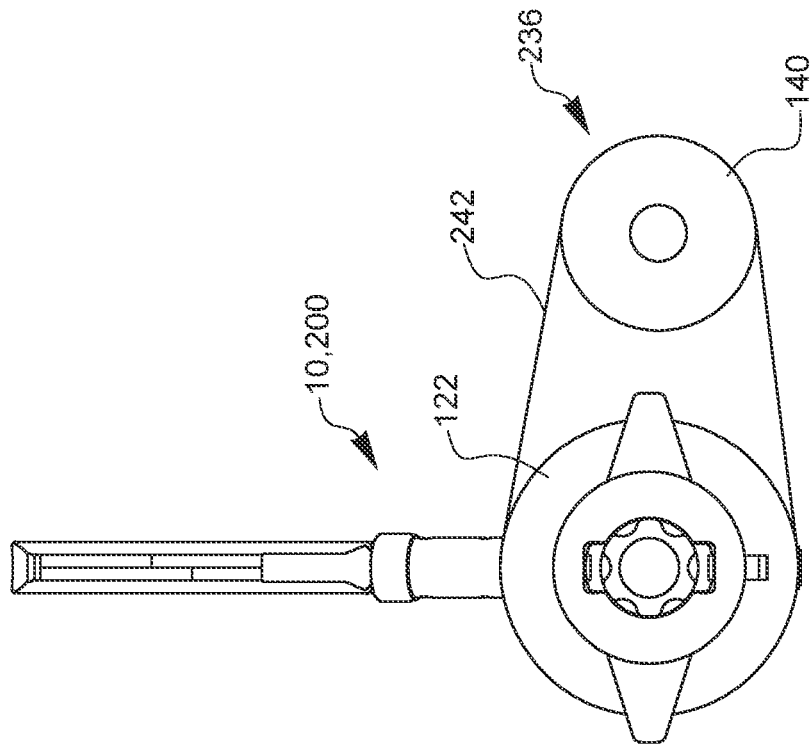
FIG. 14B is a rear view of an embodiment of the tissue manipulation device coupled to an embodiment of a first robotic interface.
Figure 14A:
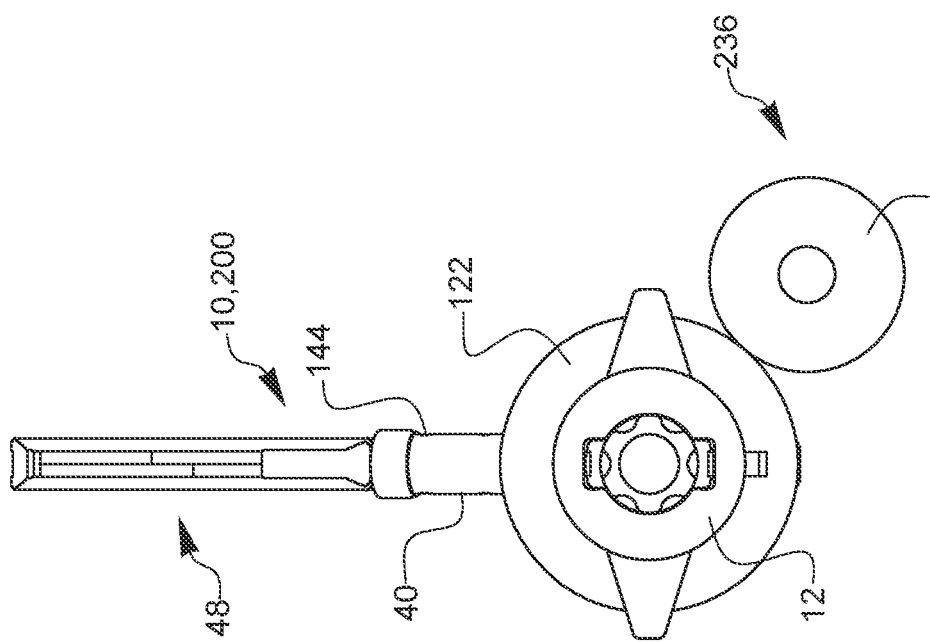
FIG. 14A is a rear view of an embodiment of the tissue manipulation device coupled to an embodiment of a first robotic interface.
Figure 14C:
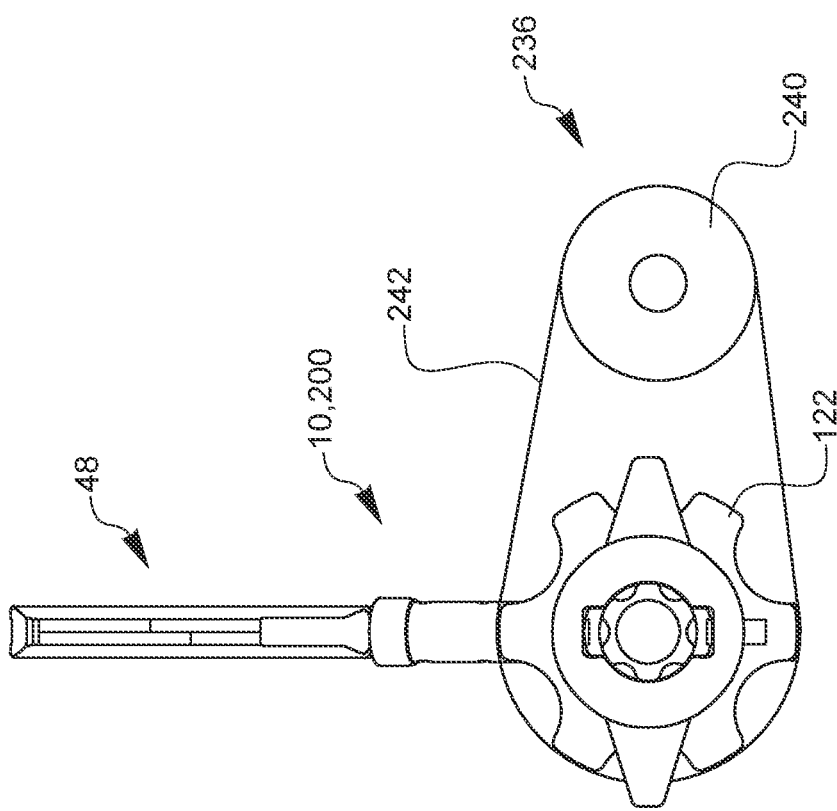
FIG. 14C is a rear view of an embodiment of the tissue manipulation device coupled to an embodiment of a first robotic interface.

In some embodiments, the tissue manipulation device 10 may be configured for use in a robotic surgical procedure. For example, a robot (not shown) with a dynamic member, such as an arm, my interface with an embodiment of the tissue manipulation device 10 to position the tissue manipulation device 10 during the procedure. The robot, via a first robotic interface 236 (an embodiment of which is illustrated in FIG. 14A) be directly or indirectly coupled to the tissue manipulation device 10 to rotate the adjustment wheel 122 (or an equivalent mechanism or gear) to rotate the end effector 48 about the end effector axis 153 relative to the distal end 44 of the shaft portion 40 to precisely position the end effector 48 during a procedure. The first robotic interface 236 may be any mechanism, assembly, or device that may interact or interface with the tissue manipulation device 10 to cause the adjustment wheel 122 (or any portion of the rotational assembly coupled to the adjustment wheel 122) to rotate. For example, in the embodiment of FIG. 14A, the first robotic interface 236 may be a gear 238 that interfaces with the adjustment wheel 122 (or an equivalent gear that acts as the adjustment wheel 122) to rotate the adjustment wheel 122. Instead of a single gear 238, the first robotic interface 236 may include any number or combination of gears to turn the adjustment wheel 122 to a desired position. In other embodiments, such as that of FIG. 14C, the first robotic interface 236 may be a drive pulley 240 with a belt 242 that is coupled the adjustment wheel 122 to rotate the adjustment wheel 122. In the embodiment of FIG. 14B, the drive pulley 240 and belt 242 may be coupled to a pulley equivalent to the adjustment wheel 122 to rotate the adjustment wheel 122.

Figure 15A:
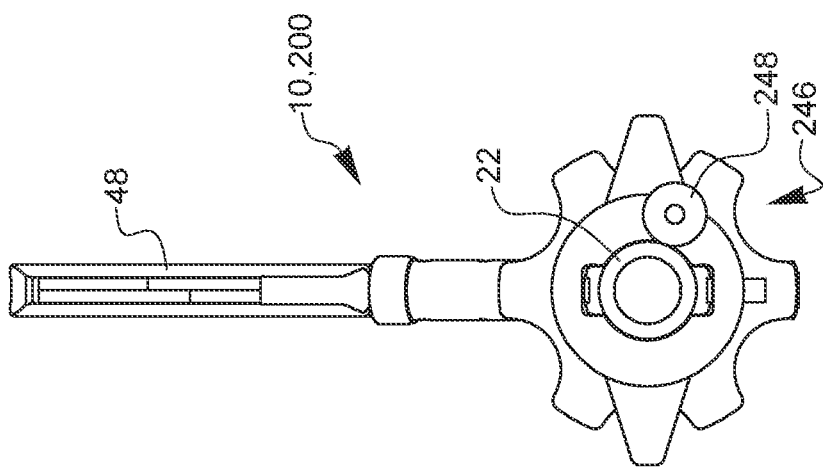
FIG. 15A is a rear view of an embodiment of the tissue manipulation device coupled to an embodiment of a second robotic interface.
Figure 15B:
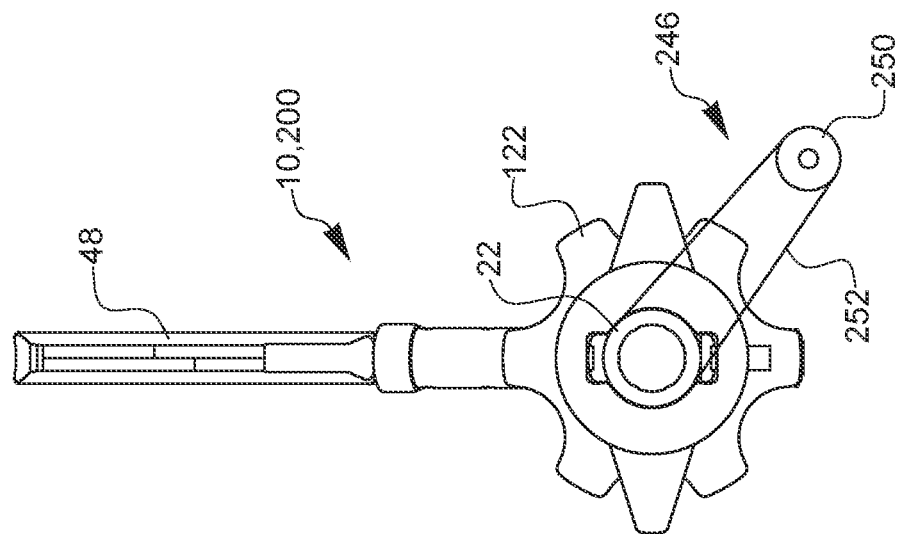
FIG. 15B is a rear view of an embodiment of the tissue manipulation device coupled to an embodiment of a second robotic interface.

In other embodiments, the robot, via a second robotic interface 246 (an embodiment of which is illustrated in FIG. 15A), may be directly or indirectly coupled to the tissue manipulation device 10 to displace the wire 52 such that the end effector 48 is displaced from the first undeployed position 49 (illustrated in FIGS. 1 and 6) to the second deployed position 51 (illustrated in FIG. 8). The second robotic interface 246 may be any mechanism, assembly, or device that may interact or interface with the tissue manipulation device 10 to cause (a) the adjustment member 22 (or any portion of the rotational assembly coupled to the adjustment member 22) to rotate and/or (b) the wire 52 to longitudinally displace. For example, in the embodiment of FIG. 15A, the second robotic interface 246 may be a gear 248 that interfaces with the adjustment member 22 (or an equivalent gear that acts as the adjustment member 22) to rotate the adjustment member 22. Instead of a single gear 248, the second robotic interface 246 may include any number or combination of gears to turn the adjustment member 22 to a desired position. In other embodiments, such as that of FIG. 15A, the second robotic interface 246 may be a drive pulley 250 with a belt 252 that is coupled the adjustment member 22 to rotate the adjustment member 22. In some embodiments, the robot will include both the first robotic interface 236 and the second robotic interface 246, or may include either the first robotic interface 236 or the second robotic interface 246. The tissue manipulation device 700 may be configured for use in such a robotic surgical procedure in a similar manner.

It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations, therefore, is not intended to limit the claims to any order, except as may be specified in the claims. Accordingly, the invention is limited only by the following claims and equivalents thereto.

What is claimed is:

1. A tissue manipulation device for minimally invasive surgery, comprising:
   a body portion;
   a shaft portion extending from a proximal end to a distal end along a shaft axis, wherein a portion of the shaft portion is coupled to a first portion of the body portion, and wherein the shaft portion includes one or more interior surfaces defining an interior portion;
   an adjustment member coupled to a second portion of the body portion, the adjustment member being displaceable relative to the second portion of the body portion from a first adjustment member position to a second adjustment member position;
   an elongated coupling portion, wherein a first portion of the coupling portion is coupled to a portion of the adjustment member, and wherein at least a portion of the coupling portion extends through the interior portion of the shaft portion; and
   an end effector assembly comprising;
      a housing extending from a proximal end to a distal end along an end effector axis, wherein the proximal end is coupled to the distal end of the shaft portion, wherein a first window extends along a first elongated portion of the housing from a proximal end to a distal end along an axis parallel to the end effector axis, and wherein a second window extends along a second elongated portion of the housing from a proximal end to a distal end along an axis parallel to the end effector axis, and wherein the housing defines a housing interior; and
      a tissue engaging assembly comprising:
         a first tissue engaging arm that includes a first arm segment, a second arm segment, and a third arm segment, the first arm segment of the first tissue engaging arm extending from a first end to a second end along a first arm segment axis, the second arm segment of the first tissue engaging arm extending from a first end to a second end along a second arm segment axis, and the third arm segment of the first tissue engaging arm extending from a first end to a second end along a third arm segment axis, wherein the first end of the first arm segment of the first tissue engaging arm is pivotably coupled to a portion of the housing at or adjacent to the distal end of the housing;
         a second tissue engaging arm that includes a first arm segment, a second arm segment, and a third arm segment, the first arm segment of the second tissue engaging arm extending from a first end to a second end along a first arm segment axis, the second arm segment of the second tissue engaging arm extending from a first end to a second end along a second arm segment axis, and the third arm segment of the second tissue engaging arm extending from a first end to a second end along a third arm segment axis, wherein the first end of the first arm segment of the second tissue engaging arm is pivotably coupled to the portion of the housing at or adjacent to the distal end of the housing; and
         a plunger coupled to a second portion of the coupling portion, wherein the second end of the third arm segment of the first tissue engaging arm is coupled to a first portion of the plunger, and the second end of the third arm segment of the second tissue engaging arm is coupled to a second portion of the plunger, the plunger being disposed within the housing interior when the adjustment member is in the second adjustment member position, and the plunger being displaceable along the end effector axis when the adjustment member is displaced between the first adjustment member position and the second adjustment member position, wherein when the adjustment member is in the first adjustment member position, the end effector assembly is in a first undeployed position, in which:

the second arm segment axis of the first tissue engaging arm is parallel to and offset from the end effector axis by a first distance; and the second arm segment axis of the second tissue engaging arm is parallel to and offset from the end effector axis by a second distance, and when the adjustment member is in the second adjustment member position, the end effector assembly is in a second deployed position, in which:

the second arm segment axis of the first tissue engaging arm is parallel to and offset from the end effector axis by a third distance that is greater than the first distance;

the second arm segment axis of the second tissue engaging arm is parallel to and offset from the end effector axis by a fourth distance that is greater than the second distance;

a portion of the first arm segment of the first tissue engaging arm and a portion of the third arm segment of the first tissue engaging arm each extends through a corresponding portion of the first window of the housing; and a portion of the first arm segment of the second tissue engaging arm and a portion of the third arm segment of the second tissue engaging arm each extends through a corresponding portion of the second window of the housing.

2. The tissue manipulation device of claim 1, wherein the first distance is equal to the second distance, and the third distance is equal to the fourth distance.

3. The tissue manipulation device of claim 2, wherein a portion of the shaft axis is non-linear.

4. The tissue manipulation device of claim 3, wherein the portion of the shaft axis has an arcuate shape.

5. The tissue manipulation device of claim 4, wherein the portion of the shaft axis extends from a first point that is disposed between the proximal end of the shaft portion and the distal end of the shaft portion to a second point that is at or adjacent to the distal end of the shaft portion.

6. The tissue manipulation device of claim 1, wherein when the end effector assembly is in the first undeployed position:

the first arm segment axis of the first arm segment of the first tissue engaging arm, the second arm segment axis of the second arm segment of the first tissue engaging arm, and the third arm segment axis of the third arm segment of the first tissue engaging arm are each coaxially aligned and parallel to the end effector axis; and the first arm segment axis of the first arm segment of the second tissue engaging arm, the second arm segment axis of the second arm segment of the second tissue engaging arm, and the third arm segment axis of the third arm segment of the second tissue engaging arm are each coaxially aligned and parallel to the end effector axis.

7. The tissue manipulation device of claim 6, wherein when the end effector assembly is in the second deployed position:

the first arm segment axis of the first arm segment of the first tissue engaging arm forms a first oblique angle with the end effector axis;

the third arm segment axis of the third arm segment of the first tissue engaging arm forms a second oblique angle with the end effector axis, and the first arm segment axis of the first arm segment of the second tissue engaging arm forms a third oblique angle with the end effector axis; and the third arm segment axis of the third arm segment of the second tissue engaging arm forms a fourth oblique angle with the end effector axis.

8. The tissue manipulation device of claim 7, wherein the first oblique angle, the second oblique angle, the third oblique angle, and the fourth obtuse angle are substantially equal.

9. The tissue manipulation device of claim 7, wherein each of the first oblique angle, the second oblique angle, the third oblique angle, and the fourth obtuse angle is between 35° and 55°.

10. The tissue manipulation device of claim 1, wherein when the end effector assembly is in the second deployed position:

the first end of the first arm segment of the first tissue engaging arm is disposed in the housing interior;

the second end of the third arm segment of the first tissue engaging arm is disposed in the housing interior;

the first end of the first arm segment of the second tissue engaging arm is disposed in the housing interior; and the second end of the third arm segment of the second tissue engaging arm is disposed in the housing interior.

11. The tissue manipulation device of claim 1, wherein the second end of the third arm segment of the first tissue engaging arm is pivotably coupled to the first portion of the plunger, and the second end of the third arm segment of the second tissue engaging arm is pivotably coupled to the second portion of the plunger.

12. The tissue manipulation device of claim 1, wherein the first end of the first arm segment of the first tissue engaging arm is pivotably coupled to a first portion of a hub that is secured to the portion of the housing at or adjacent to the distal end of the housing, and the first end of the first arm segment of the second tissue engaging arm is pivotably coupled to a second portion of the hub.

13. The tissue manipulation device of claim 12, wherein:

the second end of the first arm segment of the first tissue engaging arm is pivotably coupled to the first end of the second arm segment of the first tissue engaging arm by a first living hinge;

the second end of the second arm segment of the first tissue engaging arm is pivotably coupled to the first end of the third arm segment of the first tissue engaging arm by a second living hinge;

the first end of the first arm segment of the first tissue engaging arm is pivotably coupled to the first portion of the hub by a third living hinge;

the second end of the first arm segment of the second tissue engaging arm is pivotably coupled to the first end of the second arm segment of the second tissue engaging arm by a fourth living hinge;

the second end of the second arm segment of the second tissue engaging arm is pivotably coupled to the first end of the third arm segment of the second tissue engaging arm by a fifth living hinge; and the first end of the first arm segment of the second tissue engaging arm is pivotably coupled to the second portion of the hub by a sixth living hinge.

14. The tissue manipulation device of claim 1, wherein the proximal end of the housing is rotatably coupled to the distal end of the shaft portion such that the housing and the tissue engaging assembly of the end effector assembly rotates about the end effector axis relative to the distal end of the shaft portion.

15. The tissue manipulation device of claim 14, further comprising an adjustment wheel coupled to the proximal end of the housing and to a third portion of the body portion such that the adjustment wheel is configured to rotate about a wheel axis relative to the body portion, the adjustment wheel being linearly displaceable along the wheel axis from a locked position, in which rotation of the adjustment wheel about the wheel axis is prevented, to an unlocked position, in which rotation of the adjustment wheel about the wheel axis rotates the housing about the end effector axis relative to the distal and of the shaft portion.

16. The tissue manipulation device of claim 15, further comprising a post fixed relative to the housing, and the adjustment wheel further comprising a plurality of locking slots, wherein in the locked position, the post is disposed within a corresponding one of the plurality of locking slots to prevent rotation of the adjustment wheel about the wheel axis, and in the unlocked position, the post is disposed remote from each of the plurality of locking slots to allow rotation of the adjustment wheel about the wheel axis.

17. The tissue manipulation device of claim 1, wherein the plunger is disposed within the housing interior when the adjustment member is in the first adjustment member position.

18. The tissue manipulation device of claim 1, wherein the portion of the shaft portion coupled to the first portion of the body portion is disposed at adjacent to the proximal end of the shaft portion.

19. The tissue manipulation device of claim 1, wherein the coupling portion is a wire, and wherein a proximal end of the wire is coupled to the portion of the adjustment member, and a distal end of the wire is coupled to the plunger.

20. The tissue manipulation device of claim 1, the housing of the end effector assembly further comprising:
   a third window extending along a third elongated portion of the housing from a proximal end to a distal end along an axis parallel to the end effector axis; and
   a fourth window extending along a fourth elongated portion of the housing from a proximal end to a distal end along an axis parallel to the end effector axis; and
the tissue engaging assembly further comprising:
   a third tissue engaging arm that includes a first arm segment, a second arm segment, and a third arm segment, the first arm segment of the third tissue engaging arm extending from a first end to a second end along a first arm segment axis, the second arm segment of the third tissue engaging arm extending from a first end to a second end along a second arm segment axis, and the third arm segment of the third tissue engaging arm extending from a first end to a second end along a third arm segment axis, wherein the first end of the first arm segment of the third tissue engaging arm is pivotably coupled to the portion of the housing at or adjacent to the distal end of the housing, and wherein the second end of the third arm segment of the third tissue engaging arm is coupled to a third portion of the plunger;
   a fourth tissue engaging arm that includes a first arm segment, a second arm segment, and a third arm segment, the first arm segment of the fourth tissue engaging arm extending from a first end to a second end along a first arm segment axis, the second arm segment of the fourth tissue engaging arm extending from a first end to a second end along a second arm segment axis, and the third arm segment of the fourth tissue engaging arm extending from a first end to a second end along a third arm segment axis, wherein the first end of the first arm segment of the fourth tissue engaging arm is pivotably coupled to the portion of the housing at or adjacent to the distal end of the housing, and wherein the second end of the third arm segment of the fourth tissue engaging arm is coupled to a fourth portion of the plunger,
wherein in the first undeployed position:
   the second arm segment axis of the third tissue engaging arm is parallel to and offset from the end effector axis by a fifth distance, and
   the second arm segment axis of the fourth tissue engaging arm is parallel to and offset from the end effector axis by a sixth distance, and
wherein in the second deployed position:
   the second arm segment axis of the third tissue engaging arm is parallel to and offset from the end effector axis by a seventh distance that is greater than the fifth distance,
   the second arm segment axis of the fourth tissue engaging arm is parallel to and offset from the end effector axis by an eighth distance that is greater than the sixth distance,
   a portion of the first arm segment of the third tissue engaging arm and a portion of the third arm segment of the third tissue engaging arm each extends through a corresponding portion of the third window of the housing, and
   a portion of the first arm segment of the fourth tissue engaging arm and a portion of the third arm segment of the fourth tissue engaging arm each extends through a corresponding portion of the fourth window of the housing.

* * * * *